US011911361B2

(12) United States Patent
Vangara et al.

(10) Patent No.: US 11,911,361 B2
(45) Date of Patent: *Feb. 27, 2024

(54) STABLE CANNABINOID FORMULATIONS

(71) Applicant: RADIUS PHARMACEUTICALS, INC., Waltham, MA (US)

(72) Inventors: Kiran Kumar Vangara, Phoenix, AZ (US); Huaguang Li, Chandler, AZ (US); Ningxin Yan, Chandler, AZ (US); Hung Q. Nguyen, Chandler, AZ (US); Venkat R. Goskonda, Phoenix, AZ (US)

(73) Assignee: RADIUS PHARMACEUTICALS, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/712,515

(22) Filed: Sep. 22, 2017

(65) Prior Publication Data
US 2018/0028489 A1 Feb. 1, 2018

Related U.S. Application Data

(63) Continuation-in-part of application No. 15/499,178, filed on Apr. 27, 2017, which is a continuation-in-part of application No. 15/253,010, filed on Aug. 31, 2016, which is a continuation-in-part of application No. 15/166,476, filed on May 27, 2016, which is a continuation-in-part of application No. 14/815,936, filed on Jul. 31, 2015, now Pat. No. 11,331,279, which is a continuation-in-part of application No. 14/724,351, filed on May 28, 2015, now Pat. No. 11,224,660.

(60) Provisional application No. 62/154,660, filed on Apr. 29, 2015, provisional application No. 62/004,495, filed on May 29, 2014.

(51) Int. Cl.
| | |
|---|---|
| A61K 31/352 | (2006.01) |
| A61K 9/00 | (2006.01) |
| A61K 31/05 | (2006.01) |
| A61K 47/44 | (2017.01) |
| A61K 47/10 | (2017.01) |
| A61K 47/22 | (2006.01) |
| A61K 31/355 | (2006.01) |
| A61K 9/08 | (2006.01) |
| A61P 25/08 | (2006.01) |
| A61K 47/14 | (2017.01) |
| A61P 25/28 | (2006.01) |
| A61K 47/26 | (2006.01) |
| A61K 31/365 | (2006.01) |

(52) U.S. Cl.
CPC .......... A61K 31/352 (2013.01); A61K 9/0095 (2013.01); A61K 9/08 (2013.01); A61K 31/05 (2013.01); A61K 31/355 (2013.01); A61K 31/365 (2013.01); A61K 47/10 (2013.01); A61K 47/14 (2013.01); A61K 47/22 (2013.01); A61K 47/26 (2013.01); A61K 47/44 (2013.01); A61P 25/08 (2018.01); A61P 25/28 (2018.01)

(58) Field of Classification Search
CPC ............................... A61K 31/05; A61P 25/28
See application file for complete search history.

(56) References Cited

U.S. PATENT DOCUMENTS

| | | | |
|---|---|---|---|
| 5,989,583 A | 11/1999 | Amselem | |
| 8,222,292 B2 | 7/2012 | Goskonda et al. | |
| 2003/0021752 A1 | 1/2003 | Whittle et al. | |
| 2004/0138293 A1 | 7/2004 | Werner et al. | |
| 2005/0266108 A1 | 12/2005 | Flockhart et al. | |
| 2006/0058293 A1 | 3/2006 | Weber et al. | |
| 2006/0160888 A1 | 7/2006 | Kottayil et al. | |
| 2006/0167283 A1* | 7/2006 | Flockhart | C07C 37/70 549/390 |
| 2006/0167823 A1 | 7/2006 | Flockhart et al. | |
| 2006/0257463 A1 | 11/2006 | Elsohly et al. | |
| 2007/0104741 A1 | 6/2007 | Murty et al. | |
| 2008/0159961 A1* | 7/2008 | Woolfe | A61K 9/0078 424/45 |
| 2009/0181080 A1 | 7/2009 | Kottayil et al. | |
| 2009/0306221 A1 | 12/2009 | Guy et al. | |
| 2010/0249045 A1 | 10/2010 | Babul | |
| 2010/0273895 A1 | 10/2010 | Stinchcomb et al. | |
| 2011/0092583 A1* | 4/2011 | Murty | A61K 9/107 514/454 |
| 2011/0262442 A1 | 10/2011 | Hamilton et al. | |
| 2011/0306660 A1 | 12/2011 | Goskonda et al. | |
| 2012/0172325 A1 | 7/2012 | Currie | |

(Continued)

FOREIGN PATENT DOCUMENTS

| | | |
|---|---|---|
| BG | 111494 A | 10/2013 |
| CN | 1420761 A | 5/2003 |

(Continued)

OTHER PUBLICATIONS

Holsen et al. "Neural Mechanisms Underlying Hyperphagia in Prader-Willi Syndrome". Obesity. 2006; 14(6):1028-1037. (Year: 2006).*
Scopinho et al. "Cannabidiol Inhibits the Hyperphagia Induced by Cannabinoid-1 or Serotonin-1A Receptor Agonists". Pharmacology, Biochemistry and Behavior. 2011; 98:268-272. (Year: 2011).*
Deiana et al. "Plasma and Brain Pharmacokinetic Profile of Cannabidiol (CBD), Cannabidivarine (CBDV) . . . in Rats and Mice Following Oral and Intraperitoneal Administration and CBD Action on Obsessive-Compulsive Behavior". Psychopharmacology. 2012; 219:859-873. (Year: 2012).*

(Continued)

Primary Examiner — Jeffrey S Lundgren
Assistant Examiner — Eric Tran
(74) Attorney, Agent, or Firm — Troutman Pepper Hamilton Sanders LLP

(57) ABSTRACT

The present invention is generally directed to substantially pure cannabidiol, stable cannabinoid pharmaceutical formulations, and methods of their use.

9 Claims, 11 Drawing Sheets

(56) References Cited

U.S. PATENT DOCUMENTS

| | | | |
|---|---|---|---|
| 2012/0202891 | A1 | 8/2012 | Stinchcomb et al. |
| 2013/0210821 | A1 | 8/2013 | Vath |
| 2013/0289019 | A1 | 10/2013 | Chau |
| 2013/0296415 | A1 | 11/2013 | Goskonda et al. |
| 2014/0100269 | A1 | 4/2014 | Goskonda et al. |
| 2015/0181924 | A1 | 7/2015 | Llamas |
| 2015/0290211 | A1 | 10/2015 | Bosse et al. |
| 2015/0342902 | A1 | 12/2015 | Vangara et al. |
| 2015/0343071 | A1 | 12/2015 | Vangara et al. |
| 2015/0359756 | A1 | 12/2015 | Guy et al. |
| 2016/0271252 | A1 | 9/2016 | Kumar et al. |
| 2016/0317468 | A1 | 11/2016 | Sankar et al. |
| 2016/0367496 | A1 | 12/2016 | Kumar et al. |

FOREIGN PATENT DOCUMENTS

| | | | |
|---|---|---|---|
| CN | 1652766 | | 8/2005 |
| CN | 1886117 | A | 12/2006 |
| CN | 101132781 | A | 2/2008 |
| CN | 102083430 | A | 6/2011 |
| DE | 102012105063 | | 12/2013 |
| JP | 2000507594 | A | 6/2000 |
| JP | 2001523221 | A | 11/2001 |
| JP | 2004529892 | A | 9/2004 |
| JP | 2008523078 | A | 7/2008 |
| JP | 2009514890 | A | 4/2009 |
| JP | 2009538893 | A | 11/2009 |
| JP | 2012525416 | A | 10/2012 |
| WO | 1997036577 | | 10/1997 |
| WO | 1998008490 | | 3/1998 |
| WO | 200113886 | | 3/2001 |
| WO | 2002064109 | | 8/2002 |
| WO | 2002072102 | | 9/2002 |
| WO | WO-2006063109 | A2 * | 6/2006 ........... A61K 9/4875 |
| WO | 2009147439 | | 12/2009 |
| WO | 2011001169 | A1 | 1/2011 |
| WO | 2012071389 | | 5/2012 |
| WO | 2012093255 | A1 | 7/2012 |
| WO | 2015198077 | | 12/2015 |
| WO | 2016191651 | | 12/2016 |

OTHER PUBLICATIONS

Sofia et al. "Comparative Effects of Various Naturally Occurring Cannabinoids on Food, Sucrose and Water Consumption by Rats". Pharmacology Biochemistry and Behavior. 1976; 4(5):591-599. (Year: 1976).*

Plasma and brain pharmacokinetic profile of cannabidiol (CBD), cannabidivarine (CBDC), Δ9-tetrahydrocannabivarin (THCV) and cannabigerol (CBG) in rats and mice following oral and intraperitoneal administration and CBD action on obsessive-compulsive behaviour Psychopharmacology (2012) 219:859-873 (Year: 2012).*

International Search Report and Written Opinion for corresponding PCT Application No. PCT/US2017/029843 dated Nov. 27, 2018.

Stott CG, et al., A phase I study to assess the effect of food on the single dose bioavailability of the THC/CBD promucosal spray, Eur J Clin Pharmacol. Apr. 2013;69(4):825-34. doi: 10.1007/s00228-012-1393-4. Epub Oct. 4, 2012.

Borges et al.; Understanding the Molecular Aspects of Tetrahydrocannabinol and Cannabidiol as Antioxidants, Molecules, pp. 12663-74; 2013.

Charman et al.; Physicochemical and Physiological Mechanisms for the Effects of Food on Drug Absorption: The Role of Lipids and pH. Journal of Pharmaceutical Sciences. 1997; 86(3):269-82.

Cunha et al.; Chronic administration of cannabidiol to healthy volunteers and epileptic patients, Pharmacology. 1980, 21(3), 175-85.

DE102012105063A1 translation, accessed from: https://patents.google.com/patent/DE102012105063A1/en?oq=DE102012105063A1, accessed on May 14, 2018, pp. 1-7.

Deiana et al.; Plasma and Brain Pharmacokinetic Profile of Cannabidiol (CBD), Cannabidivarine (CBDV) . . . in Rats and Mice Following Oral and Intraperitoneal Administration and CBD Action on Obsessive-Compulsive Behavior. Psychopharmacology. 2012; 219:859-73.

GUY,et al.; Journal of Cannabis Therapeutics. 2003; 3(4):79-120.

Holsen et al.; Neural Mechanisms Underlying Hyperphagia in Prader-Willi Syndrome. Obesity. 2006; 14(6):1028-37.

Mathias et al.; Food Effect in Humans: Predicting the Risk Through In Vitro Dissolution and In Vivo Pharmacokinetic Models. AAPS J. Jul. 2015; 17(4):988-98. Epub May 2, 2015.

Mitchell et al.; Vigabatrin for infantile spasms. Pediatr Neurol. Sep. 2002;27(3):161-4.

Morgan et al.; Cannabidiol reduces cigarette consumption in tobacco smokers: preliminary findings. Randomized Controlled Trial; Addict Behav. Sep. 2013;38(9):2433-6.

Pertwee; Cannabidiol as a Potential Medicine, in Cannabinoids as Therapeutics, R. Mechoulam, ed., Birkhauser Verlag, 2005.

Solowij et al.; A Protocol for the Delivery of Cannabidiol (CBD) and Combined CBD and Delta9-Tetrahydrocannabinol (THC) by Vaporisation. BMC Pharmacology and Toxicology. 2014; 15:58.

Zgair et al.; Dietary Fats and Pharmaceutical Lipid Excipients Increase Systemic Exposure to Orally Administered Cannabis and Cannabis-Based Medicines. Am J Transl Res, 2016; 8(8):3448-59.

Trembly et al.; (1990) Double-blind clinical study of cannabidiol as a secondary anticonvulsant, paper presented at Marijuana '90 Int. Conf. on Cannabis and Cannabinoids, Kolympari (Crete), July 8-11, cited according to: Consroe P. Sandyk R. Potential role of cannabinoid"i for therapy of neurological disorders, in Murphy L., Bartke A, eds. Marijuana/ Catrabinoids, Neurobiology and Neurophysiology, CRC Press, 1992, 459-524).

Specification for U.S. Appl. No. 62/004,495, filed May 29, 2014.

Specification for U.S. Appl. No. 62/154,660, filed Apr. 29, 2015.

International Search Report and Written Opinion for Application No. PCT/US2016/034565 dated Aug. 30, 2016.

International Preliminary Report on Patentability for Application No. PCT/US2015/032955 dated Dec. 8, 2016.

International Search Report and Written Opinion for Application No. PCT/US2017/052897 dated Dec. 5, 2017.

Supplementary European Search Report for European Application No. EP 15800669.2 mailed Dec. 15, 2017.

International Preliminary Report on Patentability for Application No. PCT/US2016/034565 dated Dec. 17, 2017.

Extended European Search Report for European Application No. 16800777.1 dated Oct. 30, 2018.

International Preliminary Report on Patentability for Application No. PCT/US2017/029843 dated Dec. 6, 2018.

First Office Action with English Translation for Japanese Application No. 2016-569911 dated Mar. 5, 2019.

First Mexican Office Action for MX Application No. MX/A/2016/015636 dated Apr. 10, 2019.

Official Notification for Israeli Application No. 249197 dated Apr. 30, 2019.

Office Action for Japanese Application No. 2016-569911 dated Jun. 4, 2019.

First Office Action with English Translation for Chinese Application No. 201580041466.9 dtaed Aug. 5, 2019.

Second Mexican Office Action for MX Application No. MX/A/2016/015636 dated Aug. 14, 2019.

Full Examination Report No. 1 for Australian Application No. 2015266897 dated Aug. 19, 2019.

First Examination Report for New Zealand Application No. 726746 dated Oct. 10, 2019.

International Preliminary Report on Patentability for Application No. PCT/US2017/052897 dated Nov. 7, 2019.

Extended European Search Report for European Application No. 17803241.3 dated Jan. 3, 2020.

Further Examination Report for New Zealand Application No. 726746 dated May 6, 2020.

Communication pursuant to Article 94(3) for European Application No. 16800777.1 received from the EPO: dated May 26, 2020.

First Office Action with English Translation for Japanese Application No. 2018-513742 dated Jun. 2, 2020.

(56) References Cited

OTHER PUBLICATIONS

Third Mexican Office Action for MX Application No. MX/A/2016/015636 dated Jul. 13, 2020.
Extended European Search Report for European Application No. 17907335.8 dated Aug. 26, 2020.
Third Office Action with English Translation for Chinese Application No. 201580041466.9 dated Aug. 31, 2020.
Fourth Mexican Office Action for MX Application No. MX/A/2016/015636 dated Dec. 3, 2020.
First Examination Report for Australian Application No. 2016267585 dated Dec. 4, 2020.
Fourth Office Action with English Translation for Chinese Application No. 201580041466.9 dated Jan. 28, 2021.
Brown MJ.; "MCT Oil 101—A Review of Medium-Chain Triglycerides". [Online]. Retrieved from the Internet: Dec. 1, 2016. <https://authoritynutrition.com/mct-oil-101 1>. pp. 1-9.
Chun et al.; Tocopherol and Tocotrienol Contents of Raw and Processed Fruits and Vegetables in the United States Diet. Journal of Food Composition and Analysis. 2006; 19:196-204.
Podd et al.; The Role of Ethanol and Acetaldehyde in Flower Senescence and Fruit Ripening—A Review. Plant Growth Regulation. 1998: 26:183-189.
International Search Report and Written Opinion for Application No. PCT/US2015/032955 dated Aug. 14, 2015.
Office Action for Canadian Application No. 2,950,424 dated Jun. 11, 2021.
Office Action with English Translation for Japanese Application No. 2019-558668 dated Jun. 29, 2021.
Office Action for Israeli Application No. 249197 dated Jul. 5, 2021.
Office Action dated Jul. 25, 2022 in connection with U.S. Appl. No. 15/499,178.
BG111494A English Translation; accessed from: https://patents.google.com/patent/BG111494A/en; accessed on Jul. 16, 2022, pp. 1-6 (Year: 2013).
Behl, C.R., et al., "Improved taste acceptability for an oral hyperalimentation dosage form" Am. J. Hosp. Pharm.; pp. Abstract; (Year: 1976).
Reexamination Report dated Jul. 29, 2022 in connection with Japanese Application No. 2019-558668.
History of Changes for Study: NCT02844933, Cannabidiol Oral Solution for the Treatment of Subjects With Prader-Willi Syndrome, Clinical Trials.gov archive [online], Mar. 31, 2017, [retrieved on Jul. 12, 2022], Retrieved from the Internet: <URL: https://clinicaltrials.gov/ct2/history/NCT02844933?A=9&B=9&C=merged#StudyPageTop>.
Fifth Office Action dated Jul. 30, 2021 in connection with Chinese Application No. 201580041466.9.
Second Examination Report dated Oct. 25, 2021 in connection with Australian Application No. 2016267585.
Non Final Office Action dated Nov. 2, 2021 in connection with U.S. Appl. No. 15/253,010.
Office Action dated Nov. 23, 2021 in connection with U.S. Appl. No. 15/499,178.
Third Examination Report dated Nov. 26, 2021 in connection with Australian Application No. 2016267585.
Office Action dated Dec. 2, 2021 in connection with Canadian Application No. 3,062,814.
Office Action dated Dec. 9, 2021 in connection with Canadian Application No. 3025702.
Office Action dated Jan. 14, 2022 in connection with Canadian Application No. 2950424.
Office Action dated Jan. 26, 2022 in connection with U.S. Appl. No. 15/166,467.
First Mexican Office Action for MX Application No. MX/A/2021/006035 dated Feb. 18, 2022.
Communication pursuant to Article 94(3) for European Application No. 17803241.3 received from the EPO; dated Mar. 29, 2023.
Anonymous: "Olige Cannabidiol-Losung 50mg/ml (NRF 22.10.)", DAC/NRF 2015/2, Jan. 1, 2015 (Jan. 1, 2015), pp. 1-5, XP093003951.

Office Action dated Apr. 11, 2023 in connection with U.S. Appl. No. 15/166,476.
Office Action dated Jul. 12, 2023 in connection with Chinese Application Patent: CN 201580041466.9.
Porter et al., "Report of a parent survey of cannabidiol-enriched cannabis use in pediatric treatment-resistant epilepsy" Epilepsy & Behavior, 29 (2013) 574-577.
Office Action dated May 23, 2023 in connection with U.S. Appl. No. 15/499,178.
Fisk, I.K., et al. "Gamma-irradiation as a method of microbiological control, and its impact on the oxidative labile lipid component of Cannabis sativa and Helianthus annus", Eur. Food Res. Tech., pp. 613-621 (Year: 2009).
Trofin, I.D., et al., "Long-term Storage and Cannabis Oil Stability", Revista de Chemie Bucharest, pp. 293-297 (Year: 2012).
Second Office Action dated Jun. 6, 2023 in connection with Application No. 763449.
NCT02091375, "Antiepileptic Efficacy Study of GWP42003-P in Children and Young Adults With Dravet Syndrome (GWPCARE1)". Mar. 19, 2014; 14 pages.
NCT02091206, "A Dose-ranging Pharmacokinetics and Safety Study of GWP42003-P in Children With Dravet Syndrome (GWPCARE1)". Mar. 19, 2014; 10 pages.
NCT02006628, "A Study of GWP 42003 as Adjunctive Therapy in the First Line Treatment of Schizophrenia or Related Psychotic Disorder". Dec. 13, 2013; 9 pages.
NCT02051387, "Cannabidiol as a Different Type of an Antipsychotic: Drug Delivery and Interaction Study (CBD-IS)". Jan. 31, 2014; 7 pages.
NCT02044809, "Cannabidiol: a Novel Intervention for Cannabis Use Problems?" Jan. 24, 2014; 6 pages.
NCT02083874, "Cannabidiol (CBD) for the Management of Cannabis Withdrawal: A Phase II Proof of Concept Study" Apr. 11, 2014; 6 pages.
Abu-Sawwa, et al., 'Epidiolex (Cannabidiol) Primer: Frequently Asked Questions for Patients and Caregivers', Journal of Pediatric Pharmacology and Therapeutics, vol. 25, No. 1, pp. 75-77. DOI: 10.5863/1551-6776-25.1.75.
Costa, B. et al., 'The non-psychoactive cannabis constituent cannabidiol is an orally effective therapeutic agent in rat chronic inflammatory and neuropathic pain', European Journal of Pharmacology, vol. 556, pp. 75-83. DOI: 10.1016/j.ejphar.2006.11.006.
Hilderbrand, 'Hemp & Cannabidiol: What is a Medicine?', Missouri Medicine, vol. 115, No. 4, pp. 306-309.
Nabissi, M. et al., 'Triggering of the TRPV2 channel by cannabidiol sensitizes glioblastoma cells to cytotoxic chemotherapeutic agents', Carcinogenesis, vol. 34, No. 1, pp. 48-57.
Ward, et al., 'Cannabidiol inhibits paclitaxel-induced neuropathic pain through 5-HT1A receptors without diminishing nervous system function or chemotherapy efficacy', British Journal of Pharmacology, vol. 171, No. 3, pp. 636-645. DOI: 10.1111/bph.12439.
World Health Organisation, "Cannabidiol (CBD) Critical Review Report", Expert Committee on Drug Dependence.
Zuardi A. W. "Cannabidiol: from an inactive cannabinoid to a drug with wide spectrum of action" Rev Bras Psiquiatr. 2008;30(3):271-80.
Devinsky, O. et al; "Cannabidiol: Pharmacology and potential therapeutic role in epilepsy and other neuropsychiatric disorders" Epilepsia. Jun. 2014; 55(6): 791-802. Published online May 22, 2014.
European Search Report dated Jan. 25, 2023 in connection with European Application No. 22197632.7.
Consroe P. et al., "Controlled clinical trial of cannabidiol in Huntington's disease", Pharmacology Biochemistry and Behavior, Elsevier, US, vol. 40, No. 3, Nov. 1, 1991, pp. 701-708.
Caterina Scuderi et al., "Cannabidiol in medicine: a review of its therapeutic potential in CNS disorders", Physiotherapy Research, vol. 23, No. 5, May 1, 2009, pp. 597-602.
Office Action dated Jun. 27, 2023 in connection with Japanese Patent Application No. 2022-089421.

\* cited by examiner

I.

STABLE CANNABINOID FORMULATIONS

PRIORITY

This application claims priority to U.S. patent application Ser. No. 15/499,178, filed Apr. 27, 2017, U.S. patent application Ser. No. 15/253,010, filed Aug. 31, 2016, U.S. patent application Ser. No. 15/166,476, filed May 27, 2016, U.S. patent application Ser. No. 14/815,936, filed Jul. 31, 2015, U.S. patent application Ser. No. 14/724,351, filed May 28, 2015 and U.S. Provisional Patent Application No. 62/004,495, filed May 29, 2014, and 62/154,660, filed Apr. 29, 2015. The entire contents of each application is incorporated herein by reference.

FIELD OF THE INVENTION

The present invention is generally directed to substantially pure cannabidiol, stable cannabinoid pharmaceutical formulations, and methods of their use.

BACKGROUND

Cannabinoids are chemicals that are produced by cannabis flowers. Cannabinoids imitate endogenous compounds in humans.

Cannabinoids include cannabinol, cannabidiol, dronabinol (delta-9-tetrahydrocannabinol), delta-8-tetrahydrocannabinol, 11-hydroxy-tetrahydrocannabinol, 11-hydroxy-delta9-tetrahydrocannabinol, levonantradol, delta-11-tetrahydrocannabinol, tetrahydrocannabivarin, amandamide, nabilone, and acids and analogs thereof. It is now possible to synthesize many cannabinoids in a laboratory thereby eliminating the need to grow cannabis for extraction of the compounds.

One cannabinoid, cannabidiol, (−)-trans-2-p-mentha-1,8-dien-3-yl-5-pentylresorcinol, is non-psychoactive and has shown promise in treating numerous diseases and disorders. Synthetic cannabidiol has the same structure as naturally occurring cannabidiol.

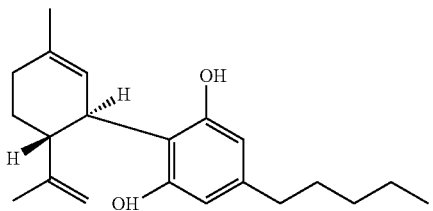 [SMILES: C=C(C)[C@@H]1CCC(C)=C[C@H]1c1c(O)cc(CCCCC)cc1O]

Commercially available cannabidiol is usually contaminated with delta 9-tetrahydrocannabinol. The presence of delta-9-tetrahydrocannabinol can be a concern because delta-9-tetrahydrocannabinol is regulated by the United States Drug Enforcement Administration as a Schedule I Drug. Having a higher Schedule number could result in easier access for patients to cannabidiol treatments. Further, delta-9-tetrahydrocannabinol is a hallucinogen and patients receiving cannabidiol wish to avoid this undesirable side effect of the delta-9-tetrahydrocannabinol contaminant. Therefore, there is a need for a substantially pure synthetically synthesized cannabidiol that does not contain delta-9-tetrahydrocannabinol.

Cannnabinoids, including cannabidiol, may be suitable for the treatment of diseases or disorders, or symptoms of diseases or disorders, such as Dravet Syndrome, Lennox Gastaut Syndrome, mycolonic seizures, juvenile mycolonic epilepsy, refractory epilepsy, schizophrenia, juvenile spasms, West syndrome, refractory infantile spasms, infantile spasms, tuberous sclerosis complex, brain tumors, neuropathic pain, cannabis use disorder, post-traumatic stress disorder, anxiety, early psychosis, Alzheimer's Disease, autism, and withdrawal from opioids, cocaine, heroin, amphetamines, and nicotine.

Accordingly, there is a need for new stable cannabinoid formulations. There is also a need for substantially pure cannabidiol.

SUMMARY OF THE INVENTION

In one aspect, the invention is directed to a method of treating Prader-Willi syndrome comprising administering an effective amount of an oral pharmaceutical formulation comprising:
cannabidiol;
a vehicle consisting of a lipid or selected from the group consisting of water, ethanol, glycerin, propylene glycol, polyethylene glycol 400 and a combination thereof.

In another aspect, the cannabidiol is greater than 98% pure.

In another aspect, the vehicle is a medium chain glyceride, preferably caprylic/capric triglyceride.

In another aspect, the vehicle is sesame oil.

In another aspect, the oral pharmaceutical formulations of the present invention further comprise an antioxidant or preservative selected from the group consisting of alpha-tocopherol, ascorbyl palmitate, methyl paraben, propyl paraben and a combination thereof.

In another aspect, the oral pharmaceutical formulations of the present invention comprise:
from about 8% to about 31% w/w cannabidiol; and
a vehicle consisting of from about 60% to about 90% w/w of a lipid or a combination of from about 40% to about 60% w/w ethanol, from about 1% to about 5% w/w polyethylene glycol, from about 5% to about 10% w/w propylene glycol and from about 20% to about 40% w/w water.

In another aspect, the oral pharmaceutical formulations of the present invention comprise cannabidiol at a concentration of about 10% w/w and caprylic/capric triglyceride at a concentration of about 89% w/w.

In another aspect, the oral pharmaceutical formulations of the present invention comprise cannabidiol at a concentration of about 31% w/w and caprylic/capric triglyceride at a concentration of about 68% w/w.

In another aspect, the oral pharmaceutical formulations of the present invention comprise cannabidiol is at a concentration of about 11% w/w and the vehicle is sesame oil at a concentration of about 80% w/w.

In another aspect, the oral pharmaceutical formulations of the present invention comprise cannabidiol at a concentration of about 8.8% w/w, and a combination of ethanol at a concentration of about 50% w/w, polyethylene glycol at a concentration of about 3% w/w, propylene glycol at a concentration of about 7.5% w/w and water at a concentration of about 30% w/w.

In another aspect, the effective amount of the oral pharmaceutical formulations of the present invention is from about 0.5 to about 100 milligrams per kilogram per day or from about 10 to about 40 milligrams per kilogram per day.

In another aspect, the invention is directed to a method of treating one or more symptoms of Prader-Willi syndrome comprising administering an effective amount of an oral pharmaceutical formulation comprising:
- cannabidiol;
- a vehicle consisting of a lipid or selected from the group consisting of water, ethanol, glycerin, propylene glycol, polyethylene glycol 400 and a combination thereof.

In a preferred aspect, the one or more symptoms of Prader-Willi syndrome is hyperphagia.

In another aspect, the invention is directed to a method of treating infantile spasms comprising administering to a patient in need thereof an effective amount of an oral pharmaceutical formulation comprising:
- cannabidiol; and
- a vehicle selected from the group consisting of a lipid, water, ethanol, glycerin, propylene glycol, polyethylene glycol 400 and a combination thereof.

In a preferred aspect, the patient is administered vigabatrin or adrenocorticotropic hormone prior to administration of the oral pharmaceutical formulation of the present invention.

In another aspect, the invention is directed to a method of treating childhood absence epilepsy comprising administering an effective amount of an oral pharmaceutical formulation comprising:
- substantially pure cannabidiol, preferably greater than 98% pure and or synthetic; and
- a vehicle selected from the group consisting of a lipid, water, ethanol, glycerin, propylene glycol, polyethylene glycol 400 and a combination thereof.

DETAILED DESCRIPTION

Figure 1:
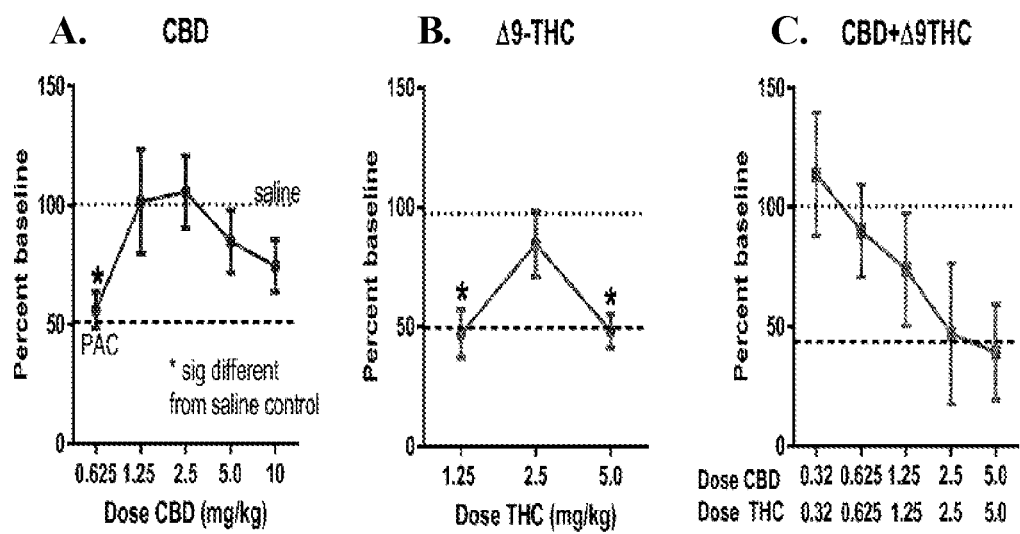
FIG. 1 shows the results from the study detailed in Example 7 and illustrates the advantages of administration of substantially pure, synthetically synthesized, cannabidiol formulations for treatment of neuropathic pain. Panel A. shows the results of CBD. Panel B. shows the results of Δ9-THC and Panel C. shows the results of CBD+Δ9THC.

As indicated above, Applicant created stable formulations with and without alcohol (see Examples 1 and 3). The formulations that do not contain alcohol are especially suitable for administration to children. Further, the alcohol-free formulations are especially suitable for patients in recovery from drug and alcohol addiction.

In addition, Applicant created stable lipid formulations (see Example 5). These formulations were also unexpectedly stable during storage (see Example 6).

Further, Applicant unexpectedly found that substantially pure cannabidiol formulations are especially suitable for treatment of neuropathic pain (see Examples 7-10 and FIGS. 1-6), epilepsy (see Examples 11-13), glioblastoma multiforme (see Examples 14 and 15 and FIGS. 7 and 8), treatment resistant seizure disorder (see Example 16) and Prader-Willi syndrome (see Example 19).

Alcohol-Free Formulations

In one embodiment, the present invention is directed to stable pharmaceutical formulation for oral administration comprising from about 0.1 to about 50% of a cannabinoid, from about 0.1 to about 40% of a polyethylene glycol, from about 0.1 to about 50% of propylene glycol, and from about 0.1 to about 20% of water, wherein the formulation does not contain alcohol and the formulation has a pH of from about 5 to about 8.

In a preferred embodiment, the formulations contain from about 1 to about 40% of a cannabinoid. In more preferred embodiments, the formulations contain from about 5 to about 35%, from about 20 to about 35% or from about 30 to 35% of a cannabinoid.

In yet another embodiment, the formulations contain a cannabinoid selected from group consisting of cannabinol, cannabidiol, dronabinol (delta-9-tetrahydrocannabinol), delta-8-tetrahydrocannabinol, 11-hydroxy-tetrahydrocannabinol, 11-hydroxy-delta-9-tetrahydrocannabinol, levonantradol, delta-11-tetrahydrocannabinol, tetrahydrocannabivarin, amandamide, nabilone, acids, analogs, and synthetic derivatives thereof. In a preferred embodiment, the cannabinoid is cannabidiol.

In a preferred embodiment, the formulations contain from about 1 to about 40% of a cannabidiol. In more preferred embodiments, the formulations contain from about 5 to about 35%, from about 20 to about 35% or from about 30 to 35% of a cannabidiol.

In yet another embodiment, the formulations contain cannabidiol that is substantially pure and synthetically synthesized which has a purity of greater than 98%. In a more preferred embodiment, the cannabidiol is greater than 99% pure. In an even more preferred embodiment, the cannabidiol is greater than 99.5% pure. In a most preferred embodiment, the cannabidiol formulation contains less than 0.3% delta-9-tetrahydrocannabinol.

In another embodiment, the formulations contain from about 0.001 to about 1% of an antioxidant. In a preferred embodiment, the formulations contain from about 0.01 to about 1% antioxidant. In a more preferred embodiment, the formulations contain from about 0.02 to about 0.5% antioxidant.

Suitable antioxidants include butylated hydroxyltoluene ("BHT"), butylated hydroxyl anisole ("BHA"), alpha-tocopherol (Vitamin E), ascorbyl palmitate, ascorbic acid, sodium ascorbate, ethylenediamino tetraacetic acid, cysteine hydrochloride, citric acid, sodium citrate, sodium bisulfate, sodium metabisulfite, lecithin, propyl gallate, sodium sulfate, monothioglycerol tert-butylhydroquinone ("TBHQ") and combinations thereof. In a preferred embodiment, the formulations contain alpha-tocopherol (Vitamin E), ascorbic acid, sodium ascorbate, ascobyl palmitate or combinations thereof.

In another embodiment, the formulations contain from about 1 to about 40% of a polyethylene glycol. In a preferred embodiment, the formulations contain from about 1 to about 35%, from about 5 to about 35%, from about 20 to about 30%, or from about 25 to about 30% polyethylene glycol.

Suitable polyethylene glycols include low molecular weight polyethylene glycols with an average molecular weight of between 200 and 10,000. One preferred polyethylene glycol that can be used is polyethylene glycol 400.

In another embodiment, the formulations contain from about 1 to about 40% of polyethylene glycol 400. In a preferred embodiment, the formulations contain from about 1 to about 35%, from about 5 to about 35%, from about 20 to about 30%, or from about 25 to about 30% polyethylene glycol 400.

In another embodiment, the formulations contain from about 1 to about 50% of propylene glycol. In a preferred embodiment, the formulations contain from about 1 to about 40%, from about 5 to about 35%, from about 20 to about 35%, or from about 30 to about 35% propylene glycol.

In a further embodiment, the formulations contain water. The formulations can contain 0% water. If the formulations contain water, they can include from about 1 to about 15% water, from about 1 to about 10% water, or from about 4 to about 8% water.

The pH of the formulations may be modified using any pharmaceutically acceptable means. Preferably the pH of the formulation is from about 5 to about 8. In a more preferred embodiment, the pH of the formulations is from about 6 to about 7. In a most preferred embodiment, the pH of the formulations is from about 6.2 to about 6.7.

The formulations of the present invention may also contain sweeteners, sweetener enhancers, preservatives, pH modifiers, and flavoring agents.

Suitable sweeteners include, but are not limited to, sucralose, sucrose, aspartame, saccharin, dextrose, mannitol, xylitol, and combinations thereof.

If the formulations contain a sweetener, the formulations preferably contain from about 0.001 to about 1% sweetener.

If the formulations contain a sweetness enhancer, the formulations preferably contain from about 0.001 to about 1% sweetness enhancer.

Suitable sweetness enhancers include, but are not limited to, the ammonium salt forms of crude and refined Glycyrrhizic Acid. Magnasweet® products (available from Mafco Worldwide Corporation, Magnasweet is a registered trademark of Mafco Worldwide Corporation) use the ammonium salt forms of crude and refined Glycyrrhizic Acid. Glycyrrhizic Acid is also available as a pure derivative in the sodium and potassium salt forms.

Suitable pH modifiers include, but are not limited to, hydrochloric acid, ascorbic acid, citric acid, sodium citrate, fumaric acid, sodium hydroxide, sodium bicarbonate, sodium carbonate, ammonium carbonate, and combinations thereof.

Suitable preservatives include, but are not limited to, methyl paraben, propyl paraben, benzyl alcohol, benzoic acid, sodium benzoate, sorbic acid, and combinations thereof.

Suitable flavoring agents include, but are not limited to, raspberry, peppermint oil, grape flavor, menthol, spearmint oil, citrus oil, cinnamon oil, strawberry flavor, cherry flavor, raspberry flavor, orange oil, lemon oil, lemon mint flavor, fruit punch flavor, and combinations thereof. In a preferred embodiment, the formulations contain strawberry flavor.

If the formulations contain a flavoring agent, the formulations preferably contain from about 0.001 to about 1% flavoring agent. In a more preferred embodiment, the formulations contain from about 0.005 to about 0.5% of the flavoring agent.

The formulations are suitable for oral, buccal, sublingual, inhalation or intravenous/intramuscular administration. Preferably, the formulations are liquids administered orally. More preferably, the formulations are simple solutions administered orally.

Formulations Containing Alcohol

In another embodiment, the invention is directed to stable pharmaceutical formulation for oral administration comprising from about 0.1 to about 40% of a cannabinoid, from about 0.1 to about 25% of a polyethylene glycol, from about 0.1 to about 40% of propylene glycol, optionally from about 0.1 to about 50% of water, and from about 0.1 to about 70% of alcohol, wherein the formulation has a pH of from about 5 to about 8.

In a preferred embodiment, the formulations contain from about 1 to about 35% of a cannabinoid. In a more preferred embodiment, the formulations contain from about 1 to about 15%, from about 5 to about 12% or from about 7 to about 11% cannabinoid. Alternatively, the formulations may contain from about 20 to about 35% or from about 30 to about 35% cannabinoid.

In yet another embodiment, the formulations contain a cannabinoid selected from group consisting of cannabinol, cannabidiol, dronabinol (delta-9-tetrahydrocannabinol), delta-8-tetrahydrocannabinol, 11-hydroxy-tetrahydrocannabinol, 11-hydroxy-delta-9-tetrahydrocannabinol, levonantradol, delta-11-tetrahydrocannabinol, tetrahydrocannabivarin, amandamide, nabilone, acids, analogs, and synthetic derivatives thereof. In a preferred embodiment, the cannabinoid is cannabidiol.

In a preferred embodiment, the formulations contain from about 1 to about 35% of a cannabidiol. In a more preferred embodiment, the formulations contain from about 1 to about 15%, from about 5 to about 12% or from about 7 to about 11% cannabidiol. Alternatively, the formulations may contain from about 20 to about 35% or from about 30 to about 35% cannabidiol.

In yet another embodiment, the formulations contain cannabidiol that is substantially pure and synthetically synthesized which has a purity of greater than 98%. In a more preferred embodiment, the cannabidiol is greater than 99% pure. In an even more preferred embodiment, the cannabidiol is greater than 99.5% pure. In a most preferred embodiment, the cannabidiol formulation contains less than 0.3% delta-9-tetrahydrocannabinol.

In another embodiment, the formulations contain from about 0.001 to about 1% of an antioxidant. In a preferred embodiment, the formulations contain from about 0.01 to about 1% antioxidant. In a more preferred embodiment, the formulations contain from about 0.02 to about 0.5% antioxidant.

Suitable antioxidants include butylated hydroxyltoluene ("BHT"), butylated hydroxyl anisole ("BHA"), alpha-tocopherol (Vitamin E), ascorbyl palmitate, ascorbic acid, sodium ascorbate, ethylenediamino tetraacetic acid, cysteine hydrochloride, citric acid, sodium citrate, sodium bisulfate, sodium metabisulfite, lecithin, propyl gallate, sodium sulfate, tert-butylhydroquinone ("TBHQ") and combinations thereof. In a preferred embodiment, the formulations contain alpha-tocopherol (Vitamin E), ascorbyl palmitate, or combinations thereof.

In another embodiment, the formulations contain from about 1 to about 20% of propylene glycol. In a preferred embodiment, the formulations contain from about 1 to about 15% or from about 5 to about 10% propylene glycol.

In an alternative embodiment, the formulations contain from about 20 to about 50% of propylene glycol. In a preferred embodiment, the formulations contain from about 30 to about 40% or from about 35 to about 40% propylene glycol.

In another embodiment, the formulations contain from about 1 to about 20% of a polyethylene glycol. In a preferred embodiment, the formulations contain from about 1 to about 10% or from about 1 to about 5% polyethylene glycol.

In an alternative embodiment, the formulations contain from about 10 to about 30% of a polyethylene glycol. In a preferred alternative embodiment, the formulations contain from about 15 to about 25% polyethylene glycol.

Suitable polyethylene glycols include low molecular weight polyethylene glycols with an average molecular weight of between 200 and 10,000. One preferred polyethylene glycol that can be used is polyethylene glycol 400.

In another embodiment, the formulations contain from about 1 to about 20% of polyethylene glycol 400. In a preferred embodiment, the formulations contain from about 1 to about 10% or from about 1 to about 5% polyethylene glycol 400.

In an alternative embodiment, the formulations contain from about 1 to about 5% of polyethylene glycol 400. In a preferred alternative embodiment, the formulations contain from about 15 to about 25% polyethylene glycol 400.

In a further embodiment, the formulations contain water. The formulations can contain 0% water. If the formulations contain water, they can include from about 1 to about 40% water, from about 5 to about 40% water, from about 10 to about 35% water or from about 25 to about 35% water.

In yet another embodiment, the formulations contain from about 1 to about 65% alcohol. In a preferred embodiment, the formulations contain from about 10 to about 65%, from about 15 to about 60%, or from about 30 to 55% alcohol.

In an alternative embodiment, the formulations contain from about 1 to about 20% alcohol. In a preferred alternative embodiment, the formulations contain from about 1 to about 10% or from about 3 to about 7% alcohol.

The pH of the formulations may be modified using any pharmaceutically acceptable means. Preferably the pH of the formulations is from about 6 to about 7. In a more preferred embodiment, the pH of the formulations is from about 6.2 to about 6.7.

The formulations of the present invention may also contain sweeteners, sweetener enhancers, pH modifiers, preservatives, and flavoring agents.

Suitable sweeteners include, but are not limited to, sucralose, sucrose, aspartame, saccharin, dextrose, mannitol, xylitol, and combinations thereof.

If the formulations contain a sweetener, the formulations preferably contain from about 0.001 to about 1% sweetener.

Suitable sweetness enhancers include, but are not limited to, the ammonium salt forms of crude and refined Glycyrrhizic Acid. Magnasweet® products (available from Mafco Worldwide Corporation, Magnasweet is a registered trademark of Mafco Worldwide Corporation) use the ammonium salt forms of crude and refined Glycyrrhizic Acid. Glycyrrhizic Acid is also available as a pure derivative in the sodium and potassium salt forms.

If the formulations contain a sweetness enhancer, the formulations preferably contain from about 0.001 to about 1% sweetness enhancer.

Suitable pH modifiers include, but are not limited to, hydrochloric acid, ascorbic acid, citric acid, sodium citrate, fumaric acid, sodium hydroxide, sodium bicarbonate, sodium carbonate, ammonium carbonate, and combinations thereof.

Suitable preservatives include, but are not limited to, methyl paraben, propyl paraben, benzyl alcohol, benzoic acid, sodium benzoate, sorbic acid, and combinations thereof.

Suitable flavoring agents include, but are not limited to, raspberry, peppermint oil, grape flavor, menthol, spearmint oil, citrus oil, cinnamon oil, strawberry flavor, cherry flavor, raspberry flavor, orange oil, lemon oil, lemon mint flavor, fruit punch flavor, and combinations thereof. In a preferred embodiment, the formulations contain fruit punch flavor, raspberry flavor, grape flavor, or lemon mint flavor.

If the formulations contain a flavoring agent, the formulations preferably contain from about 0.001 to about 1% flavoring agent. In a more preferred embodiment, the formulations contain from about 0.005 to about 0.5% of the flavoring agent.

The formulations are suitable for oral, buccal, sublingual, inhalation or intravenous/intramuscular administration. Preferably, the formulations are liquids administered orally. More preferably, the formulations are simple solutions administered orally.

Formulations Containing Lipids

In another embodiment, the invention is directed to stable pharmaceutical formulation for oral administration comprising from about 0.1 to about 40% of a cannabinoid and from about 10 to about 95% of a lipid.

In a preferred embodiment, the lipid is selected from the group consisting of sesame oil, olive oil, corn oil, sunflower oil, safflower oil, flaxseed oil, almond oil, peanut oil, walnut oil, cashew oil, castor oil, coconut oil, palm oil, soybean oil, canola oil, vegetable oil, rice bran oil, fatty acids including caproic acid, enanthic acid, caprylic acid, pelargonic acid, capric acid, undecylenic acid, lauric acid, myristic acid, pentadecylic acid, palmitic acid, margaric acid, oleic acid, stearic acid, nonadecylic acid, linoleic acid, arachidic acid and arachidonic acid, medium chain glycerides, decanoyl glycerides, octanoyl glycerides, caprylic/capric triglyceride, caprylic/capric/linoleic triglyceride, oleoyl polyoxyl-6 glycerides, linoleoyl polyoxyl-6 glycerides, polyglyceryl-3 dioleate, glyceryl monolinoleate, glyceryl monocaprylate, oleic acid, and a combination thereof. In a more preferred embodiment, the lipid is a medium-chain triglyceride whose fatty acids have an aliphatic tail of from 6 to 12 carbon atoms. In a most preferred embodiment, the lipid is caprylic/capric triglyceride.

Suitable commercial sources for the lipid include Miglyol® 812N (caprylic/capric triglyceride) containing a proprietary mixture of decanoyl and octanoyl glycerides (fatty acid esters) (Miglyol is available from and a registered trademark of Cremer Oleo GmbH & Co.) and Miglyol® 840 (caprylic/capric/linoleic triglyceride) containing a proprietary mixture of propylene glycol dicaprylate/dicaprate and otherwise known as decanoic acid/octanoic acid/propane-1, 2-diol.

In yet another embodiment, the formulations contain a cannabinoid selected from group consisting of cannabinol, cannabidiol, dronabinol (delta-9-tetrahydrocannabinol), delta-8-tetrahydrocannabinol, 11-hydroxy-tetrahydrocannabinol, 11-hydroxy-delta-9-tetrahydrocannabinol, levonantradol, delta-11-tetrahydrocannabinol, tetrahydrocannabivarin, amandamide, nabilone, acids, analogs, and synthetic derivatives thereof. In a preferred embodiment, the cannabinoid is cannabidiol.

In yet another embodiment, the formulations contain cannabidiol that is substantially pure and synthetically synthesized which has a purity of greater than 98%. In a more preferred embodiment, the cannabidiol is greater than 99% pure. In an even more preferred embodiment, the cannabidiol is greater than 99.5% pure. In a most preferred embodiment, the cannabidiol formulation contains less than 0.3% delta-9-tetrahydrocannabinol.

In a preferred embodiment, the formulations contain from about 1 to about 35% of a cannabidiol. In a more preferred embodiment, the formulations contain from about 10 to about 32% cannabidiol. In a most preferred embodiment, the formulations contain about 31.09% cannabidiol.

In a preferred embodiment, the formulations contain from about 20 to about 90% of lipids. In a more preferred embodiment, the formulations contain from about 50 to about 90% lipids. In a most preferred embodiment, the formulations contain from about 50 to about 74% lipids.

In yet another embodiment, the formulations contain alcohol. The formulations can contain 0% alcohol. If the formulations contain alcohol, they can include from about 0.1 to about 20% alcohol. In a preferred embodiment, the formulations contain from about 1 to about 15% alcohol. In a more preferred embodiment, the formulations contain from about 1 to about 10% alcohol.

In another embodiment, the formulations contain an antioxidant. The formulations can contain 0% antioxidant. If the formulations contain antioxidant, they can include from about 0.01 to about 1% of an antioxidant. In a preferred embodiment, the formulations contain from about 0.02 to about 0.5% antioxidant.

Suitable antioxidants include butylated hydroxyltoluene, butylated hydroxyl anisole, alpha-tocopherol (Vitamin E), ascorbyl palmitate, ascorbic acid, sodium ascorbate, ethylenediamino tetraacetic acid, cysteine hydrochloride, citric acid, sodium citrate, sodium bisulfate, sodium metabisulfite, lecithin, propyl gallate, sodium sulfate, TBHQ, and combinations thereof. In a preferred embodiment, the formulations contain alpha-tocopherol (Vitamin E), ascorbyl palmitate or combinations thereof.

Suitable sweeteners include, but are not limited to, sucralose, sucrose, aspartame, saccharin, dextrose, mannitol, xylitol, and combinations thereof. In a preferred embodiment the sweetener is saccharin.

If the formulations contain a sweetener, the formulations preferably contain from about 0.01 to about 2% sweetener. In a more preferred embodiment, the formulations contain from about 0.01 to about 0.8% sweetener. In a most preferred embodiment, the formulations contain from about 0.02 to about 0.05% sweetener.

Suitable sweetness enhancers include, but are not limited to, the ammonium salt forms of crude and refined Glycyrrhizic Acid. Magnasweet® products (available from Mafco Worldwide Corporation, Magnasweet is a registered trademark of Mafco Worldwide Corporation) use the ammonium salt forms of crude and refined Glycyrrhizic Acid. Glycyrrhizic Acid is also available as a pure derivative in the sodium and potassium salt forms.

If the formulations contain a sweetness enhancer, the formulations preferably contain from about 0.001 to about 1% sweetness enhancer.

Suitable pH modifiers include, but are not limited to, hydrochloric acid, ascorbic acid, citric acid, sodium citrate, fumaric acid, sodium hydroxide, sodium bicarbonate, sodium carbonate, ammonium carbonate, and combinations thereof.

Suitable preservatives include, but are not limited to, methyl paraben, propyl paraben, benzyl alcohol, benzoic acid, sodium benzoate, sorbic acid, and combinations thereof.

Suitable flavoring agents include, but are not limited to, raspberry, peppermint oil, grape flavor, menthol, spearmint oil, citrus oil, cinnamon oil, strawberry flavor, cherry flavor, raspberry flavor, orange oil, lemon oil, lemon mint flavor, fruit punch flavor, and combinations thereof. In a preferred embodiment the flavoring agent is strawberry flavor.

If the formulations contain a flavoring agent, the formulations preferably contain from about 0.01 to about 1% flavoring agent. In a more preferred embodiment, the formulations contain from about 0.005 to about 0.5% of the flavoring agent.

The formulations are suitable for oral, buccal, sublingual, inhalation or intravenous/intramuscular administration. Preferably, the formulations are liquids administered orally.

Exemplary Uses of Formulations of the Present Invention (Alcohol-Containing, Alcohol-Free, and Lipid) and Synthetically Synthesized, Substantially Pure, Cannabidiol The formulations of the present invention are especially suitable for treatment of many diseases or disorders or symptoms of diseases and disorders. Further, cannabidiol which is synthetically synthesized and substantially pure will be even more effective and suitable for the treatment of diseases or symptoms of these diseases.

The formulations of the present invention may be administered to a patient in a fed condition. As used herein a "fed condition" refers to a patient that consumes food prior to administration of a formulation of the present invention and from which the food has not been cleared from the gastrointestinal tract prior to the administration.

Disease and disorders or symptoms of these disease or disorders that can be treated or prevented by formulations of the present invention include, but are not limited to, Prader-Willi syndrome, obesity, graft versus host disease, gelastic seizures/hypothalamic hamartoma, neonatal seizures, movement disorders including dystonia, central pain syndromes including but not limited to complex regional pain syndrome, phantom limb pain, multiple sclerosis, traumatic brain injury, radiation therapy, acute and chronic graft versus host disease, T-cell autoimmune disorders, colitis, Dravet Syndrome, Lennox Gastaut Syndrome, mycolonic seizures, juvenile mycolonic epilepsy, refractory epilepsy, childhood absence epilepsy, schizophrenia, juvenile spasms, West syndrome, infantile spasms, refractory infantile spasms, tuberous sclerosis complex, brain tumors, neuropathic pain, cannabis use disorder, post-traumatic stress disorder, anxiety, early psychosis, Alzheimer's Disease, autism, acne, Parkinson's disease, social anxiety disorder, depression, diabetic retinopathy, diabetic nephropathy, diabetic neuropathy, ischemic injury of heart, ischemic injury of brain, chronic pain syndrome, rheumatoid arthritis, patients encountering adverse emotional stimuli, nausea and addiction disorders related to drugs of abuse such as opioid, heroin, cocaine, amphetamine dependence and including acute and long-term treatment of dependence and relapse associated with drugs of abuse.

As first explained in U.S. Patent Application No. 62/004,495, Applicant unexpectedly created a new synthetic pathway for creating cannabidiol. This new process eliminated the need to grow cannabis in order to extract cannabidiol. Applicant's cannabidiol has a high purity level and is substantially free of Schedule I drugs, including delta-9-tetrahydrocannabinol.

Applicant chemically synthesized cannadbidiol by combining p-menthadienol and olivetol in toluene or dichloromethane or hexane with a p-toluene sulfonic acid catalyst to produce cannabidiol (see diagram below).

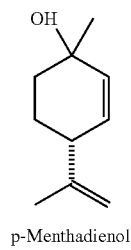
p-Menthadienol

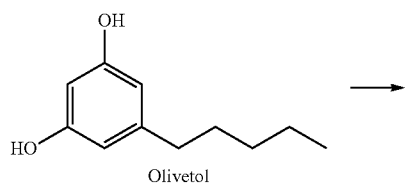
Olivetol

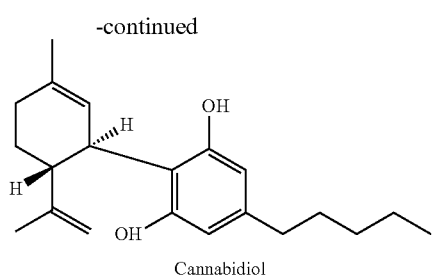
Cannabidiol

In an embodiment, the present invention is directed to methods for treating Prader-Willi syndrome comprising administering the formulations of the present invention to a patient in need thereof.

In another embodiment, the present invention is directed to methods for treating one or more symptoms of Prader-Willi syndrome comprising administering the formulations of the present invention to a patient in need thereof.

In a preferred embodiment, the one or more symptoms of Prader-Willi syndrome is hyperphagia.

In another embodiment, the present invention is directed to methods for treating a Prader-Willi syndrome comprising administering synthetically synthesized, substantially pure, cannabidiol to a patient in need thereof.

In another embodiment, the present invention is directed to methods for treating infantile spasms comprising administering the formulations of the present invention to a patient in need thereof.

In another embodiment, the invention is directed to a method of treating childhood absence epilepsy comprising administering the formulations of the present invention to a patient in need thereof.

In another embodiment, the present invention is directed to methods for treating obesity comprising administering synthetically synthesized, substantially pure, cannabidiol to a patient in need thereof.

In an embodiment, the present invention is directed to methods for treating graft versus host disease comprising administering the formulations of the present invention to a patient in need thereof.

In another embodiment, the present invention is directed to methods for treating graft versus host disease comprising administering synthetically synthesized, substantially pure, cannabidiol to a patient in need thereof.

In an embodiment, the present invention is directed to methods for preventing or treating acute and chronic graft versus host disease comprising administering the formulations of the present invention to a patient in need thereof.

In another embodiment, the present invention is directed to methods for preventing or treating acute and chronic graft versus host disease comprising administering synthetically synthesized, substantially pure, cannabidiol to a patient in need thereof.

In an embodiment, the present invention is directed to methods for treating gelastic seizures/hypothalamic hamartoma comprising administering the formulations of the present invention to a patient in need thereof.

In another embodiment, the present invention is directed to methods for treating gelastic seizures/hypothalamic hamartoma comprising administering synthetically synthesized, substantially pure, cannabidiol to a patient in need thereof.

In an embodiment, the present invention is directed to methods for treating neonatal seizures comprising administering the formulations of the present invention to a patient in need thereof.

In another embodiment, the present invention is directed to methods for treating neonatal seizures comprising administering synthetically synthesized, substantially pure, cannabidiol to a patient in need thereof.

In another embodiment, the present invention is directed to methods for treating movement disorders comprising administering synthetically synthesized, substantially pure, cannabidiol to a patient in need thereof, preferably the movement disorder is dystonia.

In an embodiment, the present invention is directed to methods for treating movement disorders comprising administering the formulations of the present invention to a patient in need thereof, preferably the movement disorder is dystonia.

In another embodiment, the present invention is directed to methods for treating central pain syndromes comprising administering synthetically synthesized, substantially pure, cannabidiol to a patient in need thereof, preferably the central pain syndrome is complex regional pain syndrome.

In an embodiment, the present invention is directed to methods for treating central pain syndromes comprising administering the formulations of the present invention to a patient in need thereof, preferably the central pain syndrome is complex regional pain syndrome.

In an embodiment, the present invention is directed to methods for treating phantom limb pain comprising administering the formulations of the present invention to a patient in need thereof.

In another embodiment, the present invention is directed to methods for treating phantom limb pain comprising administering synthetically synthesized, substantially pure, cannabidiol to a patient in need thereof.

In an embodiment, the present invention is directed to methods for providing neuroprotection after stroke comprising administering the formulations of the present invention to a patient in need thereof.

In another embodiment, the present invention is directed to methods for providing neuroprotection after stroke comprising administering synthetically synthesized, substantially pure, cannabidiol to a patient in need thereof.

In an embodiment, the present invention is directed to methods for treating traumatic brain injury comprising administering the formulations of the present invention to a patient in need thereof.

In another embodiment, the present invention is directed to methods for treating traumatic brain injury comprising administering synthetically synthesized, substantially pure, cannabidiol to a patient in need thereof.

In an embodiment, the present invention is directed to methods for treating brain injury due to radiation therapy comprising administering the formulations of the present invention to a patient in need thereof.

In another embodiment, the present invention is directed to methods for treating brain injury due to radiation therapy comprising administering synthetically synthesized, substantially pure, cannabidiol to a patient in need thereof.

In an embodiment, the present invention is directed to methods for providing enhancement of neural repair following traumatic brain injury, concussion, cerebral infarction, brain irradiation or encephalomyelitis comprising administering the formulations of the present invention to a patient in need thereof.

In another embodiment, the present invention is directed to methods for providing enhancement of neural repair following traumatic brain injury, concussion, cerebral infarction, brain irradiation or encephalomyelitis comprising administering synthetically synthesized, substantially pure, cannabidiol to a patient in need thereof.

In an embodiment, the present invention is directed to methods for providing recovery from myocardial infarction comprising administering the formulations of the present invention to a patient in need thereof.

In another embodiment, the present invention is directed to methods for providing recovery from myocardial infarction comprising administering synthetically synthesized, substantially pure, cannabidiol to a patient in need thereof.

In an embodiment, the present invention is directed to methods for providing recovery from radiation injury comprising administering the formulations of the present invention to a patient in need thereof, preferably radiation injury to lung, bowel, kidney, and heart.

In another embodiment, the present invention is directed to methods for providing recovery from radiation injury comprising administering synthetically synthesized, substantially pure, cannabidiol to a patient in need thereof, preferably radiation injury to lung, bowel, kidney, and heart.

In an embodiment, the present invention is directed to methods for treating a brain tumor comprising administering the formulations of the present invention to a patient in need thereof.

In another embodiment, the present invention is directed to methods for treating a brain tumor comprising administering synthetically synthesized, substantially pure, cannabidiol to a patient in need thereof.

In an embodiment, the present invention is directed to methods for treating T-cell autoimmune disorders comprising administering the formulations of the present invention to a patient in need thereof.

In another embodiment, the present invention is directed to methods for treating T-cell autoimmune disorders comprising administering synthetically synthesized, substantially pure, cannabidiol to a patient in need thereof.

In an embodiment, the present invention is directed to methods for treating colitis comprising administering the formulations of the present invention to a patient in need thereof.

In another embodiment, the present invention is directed to methods for treating colitis comprising administering synthetically synthesized, substantially pure, cannabidiol to a patient in need thereof.

In an embodiment, the present invention is directed to methods for treating glioma comprising administering the formulations of the present invention to a patient in need thereof.

In another embodiment, the present invention is directed to methods for treating glioma comprising administering synthetically synthesized, substantially pure, cannabidiol to a patient in need thereof.

In an embodiment, the present invention is directed to methods for treating glioblastoma multiforme comprising administering the formulations of the present invention to a patient in need thereof.

In another embodiment, the present invention is directed to methods for treating glioblastoma multiforme comprising administering synthetically synthesized, substantially pure, cannabidiol to a patient in need thereof.

In an embodiment, the present invention is directed to methods for treating Dravet Syndrome comprising administering the formulations of the present invention to a patient in need thereof.

In another embodiment, the present invention is directed to methods for treating Dravet Syndrome comprising administering synthetically synthesized, substantially pure, cannabidiol to a patient in need thereof.

In yet another embodiment, the present invention is directed to methods for treating Lennox Gastaut Syndrome comprising administering the formulations of the present invention to a patient in need thereof.

In another embodiment, the present invention is directed to methods for treating Lennox Gastaut Syndrome comprising administering synthetically synthesized, substantially pure, cannabidiol to a patient in need thereof.

In a further embodiment, the present invention is directed to methods for treating Mycolonic Seizures comprising administering the formulations of the present invention to a patient in need thereof. In a more preferred embodiment, the alcohol-free formulations contain substantially pure cannabidiol.

In another embodiment, the present invention is directed to methods for treating Mycolonic Seizures comprising administering synthetically synthesized, substantially pure, cannabidiol to a patient in need thereof.

In a further embodiment, the present invention is directed to methods for treating Juvenile Mycolonic Epilepsy comprising administering the formulations of the present invention to a patient in need thereof. In a preferred embodiment, the alcohol-free formulations of the present invention are administered to young patients in need of treatment.

In another embodiment, the present invention is directed to methods for treating Juvenile Mycolonic Epilepsy comprising administering synthetically synthesized, substantially pure, cannabidiol to a patient in need thereof.

In an embodiment, the present invention is directed to methods for treating Refractory Epilepsy comprising administering the formulations of the present invention to a patient in need thereof. In a preferred embodiment, the alcohol-free formulations of the present invention are administered to young patients in need of treatment.

In another embodiment, the present invention is directed to methods for treating Refractory Epilepsy comprising administering synthetically synthesized, substantially pure, cannabidiol to a patient in need thereof.

In an embodiment, the present invention is directed to methods for treating juvenile spasms comprising administering the formulations of the present invention to a patient in need thereof. In a preferred embodiment, the alcohol-free formulations of the present invention are administered to young patients in need of treatment.

In another embodiment, the present invention is directed to methods for treating juvenile spasms comprising administering synthetically synthesized, substantially pure, cannabidiol to a patient in need thereof.

In an embodiment, the present invention is directed to methods for treating West Syndrome comprising administering the formulations of the present invention to a patient in need thereof. In a preferred embodiment, the alcohol-free formulations of the present invention are administered to young patients in need of treatment.

In another embodiment, the present invention is directed to methods for treating West Syndrome comprising administering synthetically synthesized, substantially pure, cannabidiol to a patient in need thereof.

In an embodiment, the present invention is directed to methods for treating infantile spasms comprising administering the formulations of the present invention to a patient in need thereof. In a preferred embodiment, the alcohol-free formulations of the present invention are administered to young patients in need of treatment.

In another embodiment, the present invention is directed to methods for treating infantile spasms comprising administering synthetically synthesized, substantially pure, cannabidiol to a patient in need thereof.

In an embodiment, the present invention is directed to methods for treating refractory infantile spasms comprising administering the formulations of the present invention to a patient in need thereof. In a preferred embodiment, the alcohol-free formulations of the present invention are administered to young patients in need of treatment.

In another embodiment, the present invention is directed to methods for treating refractory infantile spasms comprising administering synthetically synthesized, substantially pure, cannabidiol to a patient in need thereof.

In an embodiment, the present invention is directed to methods for treating tuberous sclerosis complex comprising administering the formulations of the present invention to a patient in need thereof. In a preferred embodiment, the alcohol-free formulations of the present invention are administered to young patients in need of treatment.

In another embodiment, the present invention is directed to methods for treating tuberous sclerosis complex comprising administering synthetically synthesized, substantially pure, cannabidiol to a patient in need thereof.

In a further embodiment, the present invention is directed to methods for treating neuropathic pain comprising administering the formulations of the present invention to a patient in need thereof. In a further embodiment, the neuropathic pain is caused by neurotoxic chemotherapy agents such as Paclitaxel, Docetaxel, Cisplatin, Oxaliplatin, Carboplatin, Vincristine, Methotrexate, Cytarabine, Fluorouracil, Ifosfamide, Cyclophosphamide, Procarbazine, etoposide, Carmustine, and Lomustine. In yet another embodiment, the neuropathic pain is caused by Paclitaxel and the patient is receiving Paclitaxel due to a diagnosis of breast, cervical, endometrial and/or ovarian cancer. In a further embodiment, the breast, cervical, endometrial and/or ovarian cancer is platinum-resistant. In another embodiment, the breast, cervical, endometrial and/or ovarian cancer is recurrent.

In another embodiment, the present invention is directed to methods for treating neuropathic pain comprising administering synthetically synthesized, substantially pure, cannabidiol to a patient in need thereof. In a further embodiment, the neuropathic pain is caused by neurotoxic chemotherapy agents such as Paclitaxel, Docetaxel, Cisplatin, Oxaliplatin, Carboplatin, Vincristine, Methotrexate, Cytarabine, Fluorouracil, Ifosfamide, Cyclophosphamide, Procarbazine, etoposide, Carmustine, and Lomustine. In yet another embodiment, the neuropathic pain is caused by Paclitaxel and the patient is receiving Paclitaxel due to a diagnosis of breast, cervical, endometrial and/or ovarian cancer. In a further embodiment, the breast, cervical, endometrial and/or ovarian cancer is platinum-resistant. In another embodiment, the breast, cervical, endometrial and/or ovarian cancer is recurrent.

In a further embodiment, the present invention is directed to methods for using cannabidiol as an analgesic comprising administering the formulations of the present invention to a patient in need thereof.

In another embodiment, the present invention is directed to methods for using cannabidiol as an analgesic comprising administering synthetically synthesized, substantially pure, cannabidiol to a patient in need thereof.

In a further embodiment, the present invention is directed to methods for treating opioid addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating opioid addiction withdrawal comprising administering synthetically synthesized, substantially pure, cannabidiol to a patient in need thereof.

In yet another embodiment, the present invention is directed to methods for treating cocaine addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating cocaine addiction withdrawal comprising administering synthetically synthesized, substantially pure, cannabidiol to a patient in need thereof.

In a further embodiment, the present invention is directed to methods for treating heroin addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating heroin addiction withdrawal comprising administering synthetically synthesized, substantially pure, cannabidiol to a patient in need thereof.

In a further embodiment, the present invention is directed to methods for treating nicotine addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating nicotine addiction withdrawal comprising administering synthetically synthesized, substantially pure, cannabidiol to a patient in need thereof.

In a further embodiment, the present invention is directed to methods for treating amphetamine addiction withdrawal comprising administering the formulations of the present invention to a patient in need thereof. In a preferred embodiment, the alcohol-free formulations of the present invention are administered to the patient in need of treatment.

In another embodiment, the present invention is directed to methods for treating amphetamine addiction withdrawal comprising administering synthetically synthesized, substantially pure, cannabidiol to a patient in need thereof.

In another embodiment, the present invention is directed to methods for treating drug dependence, wherein treatment is selected from acute and long-term.

In another embodiment, the present invention is directed to methods for treating relapse associated with drug abuse.

In an embodiment, the present invention is directed to methods for treating acne comprising administering the formulations of the present invention to a patient in need thereof.

In another embodiment, the present invention is directed to methods for treating acne comprising administering synthetically synthesized, substantially pure, cannabidiol to a patient in need thereof.

In an embodiment, the present invention is directed to methods for treating Parkinson's disease comprising administering the formulations of the present invention to a patient in need thereof.

In another embodiment, the present invention is directed to methods for treating Parkinson's disease comprising administering synthetically synthesized, substantially pure, cannabidiol to a patient in need thereof.

In an embodiment, the present invention is directed to methods for treating schizophrenia comprising administering the formulations of the present invention to a patient in need thereof.

In another embodiment, the present invention is directed to methods for treating schizophrenia comprising administering synthetically synthesized, substantially pure, cannabidiol to a patient in need thereof.

In an embodiment, the present invention is directed to methods for treating social anxiety disorder comprising administering the formulations of the present invention to a patient in need thereof.

In another embodiment, the present invention is directed to methods for treating social anxiety disorder comprising administering synthetically synthesized, substantially pure, cannabidiol to a patient in need thereof.

In a further embodiment, the present invention is directed to methods for treating depression comprising administering the formulations of the present invention to a patient in need thereof.

In another embodiment, the present invention is directed to methods for treating depression comprising administering synthetically synthesized, substantially pure, cannabidiol to a patient in need thereof.

In a further embodiment, the present invention is directed to methods for treating patients encountering adverse emotional stimuli comprising administering the formulations of the present invention to a patient in need thereof.

In another embodiment, the present invention is directed to methods for treating patients encountering adverse emotional stimuli comprising administering synthetically synthesized, substantially pure, cannabidiol to a patient in need thereof.

In an embodiment, the present invention is directed to methods for treating nausea comprising administering the formulations of the present invention to a patient in need thereof.

In another embodiment, the present invention is directed to methods for treating nausea comprising administering synthetically synthesized, substantially pure, cannabidiol to a patient in need thereof.

In an embodiment, the present invention is directed to methods for treating multiple sclerosis comprising administering the formulations of the present invention to a patient in need thereof.

In another embodiment, the present invention is directed to methods for treating multiple sclerosis comprising administering synthetically synthesized, substantially pure, cannabidiol to a patient in need thereof.

In an embodiment, the invention is directed to methods for treating symptoms of cannabis use disorder comprising administering formulations of the present invention to a patient in need thereof. In a preferred embodiment, the alcohol-free formulations of the present invention are administered to the patient in need of treatment.

In another embodiment, the present invention is directed to methods for treating symptoms of cannabis use disorder comprising administering synthetically synthesized, substantially pure, cannabidiol to a patient in need thereof.

In another embodiment, the invention is directed to methods for treating symptoms of early psychosis comprising administering formulations of the present invention to a patient in need thereof.

In another embodiment, the present invention is directed to methods for treating symptoms of early psychosis comprising administering synthetically synthesized, substantially pure, cannabidiol to a patient in need thereof.

In another embodiment, the invention is directed to methods for treating symptoms of Alzheimer's Disease comprising administering formulations of the present invention to a patient in need thereof.

In another embodiment, the present invention is directed to methods for treating symptoms of Alzheimer's Disease comprising administering synthetically synthesized, substantially pure, cannabidiol to a patient in need thereof.

In yet another embodiment, the invention is directed to methods for treating symptoms of post-traumatic stress disorder ("PT SD") comprising administering formulations of the present invention to a patient in need thereof.

In another embodiment, the present invention is directed to methods for treating symptoms of post-traumatic stress disorder PTSD comprising administering synthetically synthesized, substantially pure, cannabidiol to a patient in need thereof.

In an embodiment, the invention is directed to methods for treating symptoms of anxiety comprising administering formulations of the present invention to a patient in need thereof.

In another embodiment, the present invention is directed to methods for treating anxiety comprising administering synthetically synthesized, substantially pure, cannabidiol to a patient in need thereof.

In a further embodiment, the invention is directed to methods for treating symptoms of autism comprising administering formulations of the present invention to a patient in need thereof. In a preferred embodiment, the alcohol-free formulations of the present invention are administered to the patient in need of treatment.

In another embodiment, the present invention is directed to methods for treating symptoms of autism comprising administering synthetically synthesized, substantially pure, cannabidiol to a patient in need thereof.

Definitions

As used herein, a "patient" refers to a single patient and not a patient population.

As used herein, "synthetic" refers to the chemical synthesis of cannabidiol does not refer to cannabidiol that is extracted from cannabis plant material.

As used herein, "substantially pure" refers to a preparation having chromatographical purity of cannabidiol of greater than 98%, preferably greater than 98.5%, more preferably greater than 99.0%, and most preferably greater than 99.5%.

As used herein, "substantially free of delta-9-tetrahydrocannabinol" refers to a preparation of cannabidiol having less than 0.3% of delta-9-tetrahydrocannabinol as determined by HPLC. Preferably, the preparation contains less than 0.25% of delta-9-tetrahydrocannabinol, more preferably 0.2%, and most preferably less than 0.1% of delta-9-tetrahydrocannabinol.

As used herein, all numerical values relating to amounts, weights, and the like, that are defined as "about" each particular value is plus or minus 10%. For example, the phrase "about 10% w/w" is to be understood as "9% w/w to 11% w/w." Therefore, amounts within 10% of the claimed value are encompassed by the scope of the claims.

As used here, "liquid" refers to a flowable, fluid pharmaceutical formulation. This type of formulation is not a powder or solid.

All weights herein refer to % w/w or percent weight of the total formulation.

As used herein the term "effective amount" refers to the amount necessary to treat a patient in need thereof.

As used herein the term "pharmaceutically acceptable" refers to ingredients that are not biologically or otherwise undesirable in an oral dosage form.

As used herein, "qs" means a sufficient quantity of that component to reach a desired volume or concentration.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

All claims, aspects and embodiments of the invention, and specific examples thereof, are intended to encompass equivalents thereof.

EXAMPLES

Example 1. Alcohol-Free Formulations

The formulations in Table 1 below were prepared as follows. All the solvents are purged with nitrogen before using in manufacturing. Vitamin E, methyl paraben, propyl paraben were dissolved in propylene glycol. Polyethylene glycol 400 (PEG400) and a flavoring agent were added to the propylene glycol solution and mixed thoroughly. The water phase was prepared by dissolving sucralose and sodium ascorbate in water. Next, the solutions were combined and pH adjusted using a pH modifier. The cannabinoid was added to the excipient solution and mixed until dissolved.

Synthetically synthesized, substantially pure, cannabidiol was used as the cannabinoid.

Strawberry flavor was used as the flavoring agent.

TABLE 1

Alcohol-free Formulations

| Formulation | # AF1 | # AF2 | # AF3 | # AF4 | # AF5 | # AF6 | # AF7 | # AF8 |
| --- | --- | --- | --- | --- | --- | --- | --- | --- |
| Cannabinoid | 32 | 32 | 32 | 32 | 32 | 32 | 32 | 32 |
| PEG400 | 28 | 28 | 27.9 | 27.38 | | | 67.95 | 62.95 |
| Propylene Glycol | 34 | 34 | 34 | 34 | 62.95 | 67.95 | | |
| Water | 6 | 6 | 6 | 6 | 5 | | | 5 |
| Vitamin E (Alpha-Tocopherol) | | | | 0.05 | 0.05 | 0.05 | 0.05 | 0.05 |
| Sodium Ascorbate | | | 0.1 | 0.1 | | | | |
| Methyl Paraben | | | | 0.1 | | | | |
| Propyl Paraben | | | | 0.02 | | | | |
| Sucralose | | | | 0.05 | | | | |

TABLE 1-continued

Alcohol-free Formulations

| Formulation | # AF1 | # AF2 | # AF3 | # AF4 | # AF5 | # AF6 | # AF7 | # AF8 |
|---|---|---|---|---|---|---|---|---|
| Flavoring | | | | 0.3 | | | | |
| pH adjustment | None | 6 to 7 | 6 to 7 | 6 to 7 | | | | |
| pH | 8.7 | 6.7 | 6.6 | 6.4 | | | | |

Example 2. Stability of Alcohol-Free Formulations

The formulations listed in Table 1 were subjected to stability at 55° C. 2° C., 40° C.±2° C. under 75%±5% relative humidity, and 25° C.±2° C. under 60%±5% relative humidity. Stability of the formulations was analyzed at specified time points by evaluating for their potency (assay value) and impurity levels. Assay and impurities were detected using high-performance liquid chromatography with an ultraviolet detector. The assay was performed at 228 nm and indicated as a % of initial concentration. For all impurities, analysis was performed at 228 nm and expressed as a % area. Amounts of particular impurities are listed in Tables 2 to 13 as a percentage of area of each formulation along with amount of total impurities. Relative retention time (RRT) is given for each impurity.

TABLE 2

Stability Data for Cannabidiol Oral Solution Formulation # AF1 stored at 55° C. ± 2° C.

| 55° C.-Formulation # AF1 | RRT | 0 Week | 1 Week | 2 Weeks | 3 Weeks | 4 Weeks |
|---|---|---|---|---|---|---|
| Assay (% of initial concentration) | | 100.00 | 97.11 | 97.30 | 94.47 | 87.91 |
| % Cis-cannabidiol | 1.440 | 0.01 | 0.02 | 0.02 | 0.02 | 0.02 |
| % Delta-9-tetrahydrocannabinol | 1.729 | ND | ND | 0.01 | ND | 0.02 |
| % Trans-(1R, 6R)-3'-methyl-cannabidiol | 1.840 | 0.05 | 0.03 | 0.03 | 0.03 | 0.02 |
| % Unknown Impurity | 0.328 | ND | BQL | BQL | BQL | 0.06 |
| | 0.345 | ND | BQL | BQL | BQL | 0.07 |
| | 0.385 | ND | BQL | BQL | BQL | 0.05 |
| | 0.404 | ND | 0.08 | 0.13 | 0.23 | 0.38 |
| | 0.460 | ND | 0.05 | 0.07 | 0.10 | 0.17 |
| | 0.486 | ND | 0.42 | 0.65 | 1.23 | 2.73 |
| | 0.505 | BQL | 0.22 | 0.22 | 0.19 | ND |
| | 0.526 | ND | 0.10 | 0.14 | 0.13 | 0.17 |
| | 0.610 | ND | ND | BQL | 0.05 | 0.08 |
| | 0.702 | ND | BQL | BQL | 0.07 | 0.08 |
| | 0.742 | ND | BQL | BQL | 0.05 | 0.07 |
| | 0.774 | 0.07 | 0.06 | 0.06 | ND | ND |
| | 0.796 | ND | 0.58 | 1.04 | 2.13 | 3.80 |
| | 0.830 | BQL | 0.31 | 0.39 | 0.59 | 0.87 |
| | 0.933 | ND | BQL | 0.06 | 0.17 | 0.37 |
| | 1.881 | ND | 0.06 | 0.09 | 0.06 | 0.06 |
| | 2.025 | ND | BQL | BQL | 0.34 | 0.39 |
| | 2.291 | ND | 0.06 | ND | ND | ND |
| Total Impurities (% Area) | | 0.13 | 1.99 | 2.91 | 5.39 | 9.41 |

ND—Not Detected
BQL—Below Quantification Limit, for unknown impurity only

TABLE 3

Stability Data for Cannabidiol Oral Solution Formulation # AF2 stored at 55° C. ± 2° C.

| 55° C.-Formulation # AF2 | RRT | 0 Week | 1 Week | 2 Weeks | 3 Weeks | 4 Weeks |
|---|---|---|---|---|---|---|
| Assay (% of initial concentration) | | 100.00 | 100.31 | 99.90 | 95.25 | 96.85 |
| % Cis-cannabidiol | 1.440 | 0.01 | 0.01 | 0.01 | 0.01 | 0.01 |
| % Delta-9-tetrahydrocannabinol | 1.730 | ND | ND | 0.01 | 0.03 | 0.06 |
| % Trans-(1R, 6R)-3'-methyl-cannabidiol | 1.840 | 0.05 | 0.07 | 0.05 | 0.05 | 0.04 |
| % Unknown Impurity | 0.340 | ND | BQL | BQL | 0.05 | 0.07 |
| | 0.404 | ND | BQL | BQL | BQL | 0.08 |
| | 0.462 | ND | BQL | BQL | BQL | 0.05 |
| | 0.486 | ND | BQL | 0.22 | 0.35 | 0.94 |
| | 0.506 | ND | 0.07 | 0.13 | 0.15 | ND |
| | 0.584 | ND | BQL | BQL | 0.05 | 0.11 |
| | 0.776 | 0.07 | 0.07 | 0.06 | 0.05 | ND |
| | 0.795 | ND | BQL | 0.30 | 0.50 | 1.09 |
| | 0.830 | BQL | BQL | 0.10 | 0.14 | 0.22 |
| | 0.932 | ND | BQL | 0.07 | 0.10 | 0.18 |

TABLE 3-continued

Stability Data for Cannabidiol Oral Solution Formulation # AF2 stored at 55° C. ± 2° C.

| 55° C.-Formulation # AF2 | RRT | 0 Week | 1 Week | 2 Weeks | 3 Weeks | 4 Weeks |
|---|---|---|---|---|---|---|
|  | 2.034 | ND | ND | BQL | 0.09 | BQL |
| Total Impurities (% Area) |  | 0.13 | 0.22 | 0.95 | 1.57 | 2.85 |

ND—Not Detected
BQL—Below Quantification Limit, for unknown impurity only

TABLE 4

Stability Data for Cannabidiol Oral Solution Formulation # AF3 stored at 55° C. ± 2° C.

| 55° C.-Formulation # AF3 | RRT | 0 Week | 1 Week | 2 Weeks | 3 Weeks | 4 Weeks |
|---|---|---|---|---|---|---|
| Assay (% of initial concentration) |  | 100.00 | 99.25 | 98.60 | 98.28 | 96.12 |
| % Cis-cannabidiol | 1.440 | 0.01 | 0.01 | 0.01 | 0.01 | 0.01 |
| % Delta-9-tetrahydrocannabinol | 1.736 | ND | ND | ND | 0.01 | 0.02 |
| % Trans-(1R, 6R)-3'-methyl-cannabidiol | 1.840 | 0.05 | 0.05 | 0.05 | 0.05 | 0.05 |
| % Unknown Impurity | 0.484 | ND | ND | ND | BQL | 0.14 |
|  | 0.502 | ND | BQL | BQL | 0.05 | 0.09 |
|  | 0.775 | 0.06 | 0.09 | 0.10 | 0.06 | 0.05 |
|  | 0.793 | ND | ND | ND | 0.06 | 0.27 |
|  | 0.830 | BQL | BQL | BQL | BQL | 0.06 |
|  | 0.951 | ND | BQL | ND | BQL | 0.05 |
|  | 1.158 | ND | 0.06 | 0.08 | 0.12 | 0.05 |
| Total Impurities (% Area) |  | 0.12 | 0.21 | 0.24 | 0.36 | 0.79 |

ND—Not Detected
BQL—Below Quantification Limit, for unknown impurity only

TABLE 5

Stability Data for Cannabidiol Oral Solution Formulation # AF4 stored at 55° C. ± 2° C.

| 55° C.-Formulation # AF4 | RRT | 0 Week | 1 Week | 2 Weeks | 3 Weeks | 4 Weeks |
|---|---|---|---|---|---|---|
| Assay (% of initial concentration) |  | 100.00 | 100.92 | 99.27 | 100.16 | 98.10 |
| % Cis-cannabidiol | 1.440 | 0.01 | 0.01 | 0.01 | 0.01 | 0.01 |
| % Trans-(1R, 6R)-3'-methyl-cannabidiol | 1.840 | 0.05 | 0.05 | 0.05 | 0.06 | 0.07 |
| % Unknown Impurity | 0.403 | ND | BQL | BQL | BQL | 0.06 |
|  | 0.485 | ND | BQL | 0.06 | 0.18 | 0.38 |
|  | 0.505 | ND | BQL | 0.05 | 0.08 | 0.12 |
|  | 0.524 | ND | ND | BQL | BQL | 0.07 |
|  | 0.776 | 0.07 | 0.08 | 0.05 | 0.06 | ND |
|  | 0.794 | ND | ND | 0.07 | 0.31 | 0.70 |
|  | 0.822 | ND | ND | BQL | 0.10 | 0.15 |
|  | 0.931 | ND | ND | ND | BQL | 0.06 |
|  | 1.159 | ND | BQL | 0.08 | 0.10 | ND |
|  | 1.774 | ND | ND | ND | 0.05 | 0.11 |
| Total Impurities (% Area) |  | 0.13 | 0.14 | 0.37 | 0.95 | 1.73 |

ND—Not Detected
BQL—Below Quantification Limit, for unknown impurity only

TABLE 6

Stability Data for Cannabidiol Oral Solution Formulation # AF1 stored at 40° C. ± 2° C. under 75% ± 5% relative humidity

| 40° C.-Formulation # AF1 | RRT | 0 Week | 2 Weeks | 4 Weeks |
|---|---|---|---|---|
| Assay (% of initial concentration) |  | 100.00 | 100.18 | 95.64 |
| % Cis-cannabidiol | 1.440 | 0.01% | 0.01% | 0.01% |
| % Trans-(1R,6R)-3'-methyl-cannabidiol | 1.846 | 0.05% | 0.05% | 0.03% |
| % Unknown Impurity | 0.404 | ND | BQL | 0.12% |
|  | 0.460 | ND | 0.07% | 0.08% |
|  | 0.486 | ND | 0.23% | 0.87% |
|  | 0.505 | BQL | 0.30% | 0.30% |
|  | 0.526 | ND | 0.05% | 0.14% |
|  | 0.702 | ND | BQL | 0.06% |

TABLE 6-continued

Stability Data for Cannabidiol Oral Solution Formulation # AF1 stored at 40° C. ± 2° C. under 75% ± 5% relative humidity

| 40° C. - Formulation # AF1 | RRT | 0 Week | 2 Weeks | 4 Weeks |
|---|---|---|---|---|
| | 0.774 | 0.07% | 0.07% | ND |
| | 0.796 | ND | 0.25% | 1.31% |
| | 0.830 | BQL | 0.12% | 0.44% |
| | 0.931 | ND | ND | 0.06% |
| Total Impurities (% Area) | | 0.13% | 1.15% | 3.42% |

ND - Not Detected
BQL - Below Quantification Limit, for unknown impurity only

TABLE 7

Stability Data for Cannabidiol Oral Solution Formulation # AF2 stored at 40° C. ± 2° C. under 75% ± 5% relative humidity

| 40° C. - Formulation # AF2 | RRT | 0 Week | 2 Weeks | 4 Weeks |
|---|---|---|---|---|
| Assay (% of initial concentration) | | 100.00 | 100.08 | 98.77 |
| % Cis-cannabidiol | 1.442 | 0.01% | 0.01% | 0.01% |
| % Trans-(1R,6R)-3'-methyl-cannabidiol | 1.848 | 0.05% | 0.05% | 0.04% |
| % Unknown Impurity | 0.484 | ND | ND | 0.08% |
| | 0.506 | ND | BQL | 0.11% |
| | 0.776 | 0.07% | 0.07% | 0.06% |
| | 0.794 | ND | ND | 0.09% |
| | 0.830 | BQL | BQL | 0.05% |
| Total Impurities (% Area) | | 0.13% | 0.13% | 0.44% |

ND - Not Detected
BQL - Below Quantification Limit, for unknown impurity only

TABLE 8

Stability Data for Cannabidiol Oral Solution Formulation #AF3 stored at 40° C. ± 2° C. under 75% ± 5% relative humidity

| 40° C. - Formulation # AF3 | RRT | 0 Week | 2 Week | 4 Week |
|---|---|---|---|---|
| Assay (% of initial concentration) | | 100.00 | 98.47 | 96.90 |
| % Cis-cannabidiol | 1.442 | 0.01% | 0.01% | 0.01% |
| % Trans-(1R,6R)-3'-methyl-cannabidiol | 1.846 | 0.05% | 0.05% | 0.05% |
| % Unknown Impurity | 0.775 | 0.06% | 0.08% | 0.10% |
| | 1.160 | ND | ND | 0.05% |
| Total Impurities (% Area) | | 0.12% | 0.14% | 0.21% |

ND - Not Detected

TABLE 9

Stability Data for Cannabidiol Oral Solution Formulation # AF4 stored at 40° C. ± 2° C. under 75% ± 5% relative humidity

| 40° C. - Formulation # AF4 | RRT | 0 Week | 2 Weeks | 4 Weeks |
|---|---|---|---|---|
| Assay (% of initial concentration) | | 100.00 | 99.63 | 99.50 |
| % Cis-cannabidiol | 1.437 | 0.01% | 0.01% | 0.01% |
| % Trans-(1R,6R)-3'-methyl-cannabidiol | 1.840 | 0.05% | 0.05% | 0.06% |
| % Unknown Impurity | 0.776 | 0.07% | 0.07% | 0.08% |
| Total Impurities (% Area) | | 0.13% | 0.13% | 0.15% |

TABLE 10

Stability Data for Cannabidiol Oral Solution Formulation # AF1 stored at 25° C. ± 2° C. under 60% ± 5% relative humidity

| 25° C. - Formulation # AF1 | RRT | 0 Week | 4 Weeks |
|---|---|---|---|
| Assay (% of initial concentration) | | 100.00 | 101.24 |
| % Cis-cannabidiol | 1.440 | 0.01% | 0.01% |
| % Trans-(1R,6R)-3'-methyl-cannabidiol | 1.846 | 0.05% | 0.04% |
| % Unknown Impurity | 0.459 | ND | 0.09% |
| | 0.483 | ND | 0.11% |
| | 0.505 | BQL | 0.27% |
| | 0.774 | 0.07% | 0.06% |
| | 0.796 | ND | 0.10% |
| | 0.836 | BQL | 0.06% |
| Total Impurities (% Area) | | 0.13% | 0.74% |

ND - Not Detected
BQL - Below Quantification Limit, for unknown impurity only

TABLE 11

Stability Data for Cannabidiol Oral Solution Formulation # AF2 stored at 25° C. ± 2° C. under 60% ± 5% relative humidity

| 25° C. - Formulation # AF2 | RRT | 0 Week | 4 Weeks |
|---|---|---|---|
| Assay (% of initial concentration) | | 100.00 | 100.22 |
| % Cis-cannabidiol | 1.442 | 0.01% | 0.01% |
| % Trans-(1R,6R)-3'-methyl-cannabidiol | 1.848 | 0.05% | 0.05% |
| % Unknown Impurity | 0.776 | 0.07% | 0.07% |
| Total Impurities (% Area) | | 0.13% | 0.13% |

TABLE 12

Stability Data for Cannabidiol Oral Solution Formulation # AF3 stored at 25° C. ± 2° C. under 60% ± 5% relative humidity

| 25° C. - Formulation # AF3 | RRT | 0 Week | 4 Weeks |
|---|---|---|---|
| Assay (% of initial concentration) | | 100.00 | 97.52 |
| % Cis-cannabidiol | 1.442 | 0.01% | 0.01% |
| % Trans-(1R,6R)-3'-methyl-cannabidiol | 1.846 | 0.05% | 0.05% |
| % Unknown Impurity | 0.775 | 0.06% | 0.08% |
| Total Impurities (% Area) | | 0.12% | 0.14% |

TABLE 13

Stability Data for Cannabidiol Oral Solution Formulation # AF4 stored at 25° C. ± 2° C. under 60% ± 5% relative humidity

| 25° C. - Formulation # AF4 | RRT | T = 0 | 4 Weeks |
|---|---|---|---|
| Assay (% of initial concentration) | | 100.00 | 99.26 |
| % Cis-cannabidiol | 1.437 | 0.01% | 0.01% |
| % Trans-(1R,6R)-3'-methyl-cannabidiol | 1.840 | 0.05% | 0.06% |
| % Unknown Impurity | 0.776 | 0.07% | 0.07% |
| Total Impurities (% Area) | | 0.13% | 0.14% |

Control formulation (#AF1) showed significant increase in levels of total impurities and decrease in the assay value. Adjusting the pH of formulation (#AF2) in the range of from about 6 to about 7 increased the stability of the formulation in comparison to control formulation. This illustrates the critical role that pH plays in cannabinoid formulations' stability. Applicant determined that the pH should be from about 6 to about 7 for optimal stability. Addition of antioxidants along with pH adjustment further increased the stability of the cannabinoid formulation. For example, formulations #AF3 and #AF4, containing antioxidant(s) and pH modifiers, showed excellent stability for four weeks regardless of temperature and humidity conditions.

Example 3. Alcohol Formulations

The formulations in Tables 14 and 15 below were prepared as follows. All the solvents were purged with nitrogen before using in manufacturing. Vitamin E, ascorbyl palmitate, methyl paraben, propyl paraben, sucralose were dissolved in ethanol. propylene glycol, polyethylene glycol 400, glycerol, flavoring agent, and water were added to the solution and mixed thoroughly. Then, if applicable, the pH of the solution was adjusted using a pH modifier. The cannabinoid was added to the excipient solution and mixed until completely dissolved.

Synthetically synthesized, substantially pure, cannabidiol was used as the cannabinoid. Strawberry flavor was used as the flavoring agent.

TABLE 14

Formulations with Alcohol

| Formulation | # A5 | # A6 | # A7 | # A8 |
|---|---|---|---|---|
| Cannabinoid | 9.1 | 9.1 | 9.1 | 8.8 |
| Polyethylene glycol 400 | 3 | 3 | 3 | 3 |
| Propylene Glycol | 7.5 | 7.5 | 7.5 | 7.5 |
| Ethanol | 50.3 | 50.2 | 50.2 | 49.7 |
| Water | 30 | 30 | 30 | 30.5 |
| Vitamin E (Alpha-Tocopherol) | | 0.05 | 0.05 | 0.05 |
| Ascorbyl Palmitate | | 0.1 | 0.1 | 0.1 |
| Sucralose | 0.05 | 0.05 | 0.05 | 0.05 |
| Methyl Paraben | 0.02 | 0.02 | 0.02 | 0.02 |
| Propyl Paraben | 0.02 | 0.02 | 0.02 | 0.02 |
| Flavoring | | | | 0.3 |
| pH adjustment | None | None | pH adjusted to 6 to 7 | pH adjusted to 6 to 7 |
| Final pH of formulation | 6.06 | 4.9 | 6.5 | 6.4 |

TABLE 15

Additional Formulations with Alcohol

| Formulation | # A9 | # A10 | # A11 | # A12 | # A13 |
|---|---|---|---|---|---|
| Cannabinoid | 32 | 32 | 8.756 | 32 | 32 |
| Polyethylene glycol 400 | 18.8 | 23.8 | 3.0 | | 62.85 |
| Propylene Glycol | 39 | 39 | 7.5 | 62.85 | |
| Glycerol | 5 | | | | |
| Water | | | 30.204 | | |
| Ethanol | 5 | 5 | 50.0 | 5 | 5 |
| Vitamin E (Alpha Tocopherol) | 0.05 | 0.05 | 0.05 | 0.05 | 0.05 |
| Ascorbyl Palmitate | 0.1 | 0.1 | 0.1 | 0.1 | 0.1 |
| Sucralose | 0.05 | 0.05 | 0.05 | | |
| Methyl Paraben | 0.02 | 0.02 | 0.02 | | |
| Propyl Paraben | 0.02 | 0.02 | 0.02 | | |

Example 4. Stability of Formulations with Alcohol

The formulations listed in Table 14 and Table 15 were subjected to stability at 25° C.±2° C. under 60%±5% relative humidity and 40° C.±2° C. under 75%±5% relative humidity. Stability of the formulations was analyzed at specified time points by evaluating for their potency (assay value) and impurity levels. Assay and impurities were detected using high-performance liquid chromatography with an ultraviolet detector. The assay was performed at 228 nm and indicated as a % of initial concentration. For all impurities, analysis was performed at 228 nm and expressed as a % area. Amounts of particular impurities are listed in Table 16 to 22 as a percentage of area of each formulation along with amount of total impurities. Relative retention time (RRT) is given for each impurity.

TABLE 16

Stability Data for Cannabidiol Oral Solution Formulation # A5 stored at 25° C. ± 2° C. under 60% ± 5% relative humidity

| 25° C.-Formulation # A5 | RRT | 0 Month | 3 Months | 6 Months | 9 Months | 12 Months |
|---|---|---|---|---|---|---|
| Assay (% of initial concentration) | | 100.00 | 92.97 | 83.87 | 77.31 | 68.92 |
| % Cannabinol | 1.400 | ND | ND | ND | 0.01 | ND |
| % Cis-cannabidiol | 1.455 | 0.01 | 0.01 | 0.01 | 0.02 | 0.02 |
| % Delta-9-tetrahydrocannabinol | 1.761 | ND | ND | 0.01 | 0.15 | 0.17 |
| % Unknown Impurity | 0.319 | ND | 0.08 | 0.18 | 0.34 | 0.39 |
| | 0.337 | ND | BQL | BQL | BQL | 0.05 |
| | 0.370 | ND | BQL | 0.07 | 0.08 | 0.08 |
| | 0.389 | ND | 0.11 | 0.24 | 0.42 | 0.54 |
| | 0.448 | ND | 0.18 | 0.23 | 0.24 | 0.25 |
| | 0.479 | ND | 0.78 | 1.65 | 2.66 | 3.49 |
| | 0.494 | ND | 0.50 | 0.72 | 0.82 | 0.88 |
| | 0.522 | ND | 0.05 | BQL | BQL | BQL |
| | 0.600 | ND | BQL | 0.05 | 0.09 | 0.15 |
| | 0.678 | ND | BQL | 0.10 | 0.16 | 0.21 |
| | 0.697 | ND | BQL | 0.08 | 0.08 | 0.09 |
| | 0.713 | ND | ND | ND | 0.06 | 0.10 |
| | 0.770 | 0.05 | ND | ND | ND | ND |
| | 0.790 | ND | 0.99 | 2.28 | 4.19 | 5.55 |
| | 0.819 | ND | 0.39 | 0.87 | 1.44 | 1.97 |
| | 0.930 | ND | 0.05 | 0.21 | 0.38 | 0.56 |
| | 1.189 | ND | ND | ND | BQL | 0.09 |
| | 2.053 | ND | 0.07 | ND | BQL | 0.14 |

TABLE 16-continued

Stability Data for Cannabidiol Oral Solution Formulation # A5 stored at 25° C. ± 2° C. under 60% ± 5% relative humidity

| 25° C.-Formulation # A5 | RRT | 0 Month | 3 Months | 6 Months | 9 Months | 12 Months |
|---|---|---|---|---|---|---|
| | 3.192 | ND | ND | ND | ND | 0.09 |
| | 3.256 | ND | ND | ND | 0.08 | 0.08 |
| | 3.650 | ND | ND | ND | ND | 0.13 |
| Total Impurities (% Area) | | 0.06 | 3.21 | 6.70 | 11.22 | 15.03 |

ND—Not Detected
BQL—Below Quantification Limit, for unknown impurity only

TABLE 17

Stability Data for Cannabidiol Oral Solution Formulation # A6 stored at 25° C. ± 2° C. under 60% ± 5% relative humidity

| 25° C.-Formulation # A6 | RRT | 0 Month | 3 Months | 6 Months | 9 Months | 12 Months |
|---|---|---|---|---|---|---|
| Assay (% of initial concentration) | | 100.00 | 97.49 | 94.25 | 91.14 | 87.53 |
| % Cannabinol | 1.400 | ND | ND | ND | 0.01 | ND |
| % Cis-cannabidiol | 1.455 | 0.01 | 0.01 | 0.01 | 0.01 | ND |
| % Delta-9-tetrahydrocannabinol | 1.761 | ND | 0.06 | 0.23 | 0.68 | 0.82 |
| % Unknown Impurity | 0.390 | ND | BQL | 0.05 | 0.10 | 0.14 |
| | 0.479 | ND | BQL | 0.08 | 0.17 | 0.25 |
| | 0.496 | ND | 0.20 | 0.87 | 1.80 | 2.41 |
| | 0.577 | ND | BQL | BQL | 0.08 | 0.10 |
| | 0.721 | ND | ND | BQL | BQL | 0.05 |
| | 0.770 | 0.05 | 0.05 | BQL | BQL | BQL |
| | 0.790 | ND | 0.05 | 0.11 | 0.25 | 0.43 |
| | 0.834 | BQL | BQL | BQL | 0.05 | 0.07 |
| | 0.961 | ND | 0.06 | 0.33 | 0.71 | 0.97 |
| | 1.197 | ND | ND | ND | ND | 0.06 |
| | 1.869 | BQL | BQL | BQL | 0.06 | 0.27 |
| | 2.066 | ND | 0.07 | 0.42 | 0.59 | 0.86 |
| | 3.247 | ND | ND | ND | 0.07 | 0.08 |
| | 3.655 | ND | ND | ND | ND | 0.11 |
| Total Impurities (% Area) | | 0.06 | 0.50 | 2.10 | 4.58 | 6.62 |

ND—Not Detected
BQL—Below Quantification Limit, for unknown impurity only

TABLE 18

Stability Data for Cannabidiol Oral Solution Formulation # A7 stored at 25° C. ± 2° C. under 60% ± 5% relative humidity

| 25° C.-Formulation # A7 | RRT | 0 Month | 3 Months | 6 Months | 9 Months | 12 Months |
|---|---|---|---|---|---|---|
| Assay (% of initial concentration) | | 100.00 | 98.69 | 96.52 | 96.30 | 96.54 |
| % Cis-cannabidiol | 1.455 | 0.01 | 0.01 | 0.01 | 0.01 | 0.01 |
| % Delta-9-tetrahydrocannabinol | 1.761 | ND | 0.01 | 0.02 | 0.03 | 0.05 |
| % Unknown Impurity | 0.479 | ND | BQL | BQL | BQL | 0.07 |
| | 0.495 | ND | BQL | 0.06 | 0.14 | 0.20 |
| | 0.770 | 0.05 | 0.05 | 0.05 | 0.05 | BQL |
| | 0.793 | ND | BQL | 0.06 | 0.06 | 0.10 |
| | 0.958 | ND | ND | ND | BQL | 0.06 |
| | 1.160 | ND | BQL | 0.05 | BQL | 0.05 |
| | 1.883 | ND | ND | ND | ND | 0.06 |
| | 2.057 | ND | ND | BQL | BQL | 0.06 |
| | 3.652 | ND | ND | ND | ND | 0.05 |
| Total Impurities (% Area) | | 0.06 | 0.07 | 0.25 | 0.29 | 0.71 |

ND—Not Detected
BQL—Below Quantification Limit, for unknown impurity only

TABLE 19

Stability Data for Cannabidiol Oral Solution Formulation # A8 stored at 25° C. ± 2° C. under 60% ± 5% relative humidity

| 25° C. - Formulation # A8 | RRT | 0 Month | 3 Months | 6 Months |
|---|---|---|---|---|
| Assay (% of initial concentration) | | 100.00 | 100.51 | 100.14 |
| % Cis-cannabidiol | 1.454 | 0.04 | 0.04 | 0.04 |
| % Delta-9-tetrahydrocannabinol | 1.762 | 0.03 | 0.04 | 0.05 |
| % Unknown Impurity | 0.501 | BQL | BQL | 0.07 |
| | 1.162 | ND | BQL | 0.07 |
| | 1.198 | ND | ND | 0.05 |
| Total Impurities (% Area) | | 0.07 | 0.08 | 0.28 |

ND - Not Detected
BQL - Below Quantification Limit, for unknown impurity only

TABLE 20

Stability Data for Cannabidiol Oral Solution Formulation # A5 stored at 40° C. ± 2° C. under 75% ± 5% relative humidity

| 40° C. - Formulation # A7 | RRT | 0 Month | 3 Months | 6 Months |
|---|---|---|---|---|
| Assay (% of initial concentration) | | 100.00 | 95.22 | 89.72 |
| % Cis-cannabidiol | 1.451 | 0.01 | 0.01 | 0.01 |
| % Delta-9-tetrahydrocannabinol | 1.753 | 0.01 | 0.06 | 0.16 |
| % Unknown Impurity | 0.390 | ND | 0.05 | 0.15 |
| | 0.450 | ND | BQL | 0.06 |
| | 0.476 | BQL | 0.23 | 0.75 |
| | 0.501 | BQL | 0.30 | 0.80 |
| | 0.609 | ND | BQL | 0.05 |
| | 0.675 | ND | BQL | 0.05 |
| | 0.772 | 0.05 | BQL | ND |
| | 0.791 | ND | 0.36 | 1.35 |
| | 0.830 | BQL | 0.12 | 0.37 |
| | 0.934 | ND | BQL | 0.25 |
| | 0.958 | ND | BQL | 0.18 |
| | 1.333 | ND | ND | 0.05 |
| | 1.982 | ND | ND | 0.17 |
| | 2.062 | BQL | 0.05 | 0.32 |
| | 3.253 | ND | BQL | 0.09 |
| | 3.744 | ND | ND | 0.13 |
| Total Impurities (% Area) | | 0.07 | 1.18 | 4.94 |

ND - Not Detected
BQL - Below Quantification Limit, for unknown impurity only

TABLE 21

Stability Data for Cannabidiol Oral Solution Formulation # A6 stored at 40° C. ± 2° C. under 75% ± 5% relative humidity

| 40° C. - Formulation # A8 | RRT | 0 Month | 3 Months | 6 Months |
|---|---|---|---|---|
| Assay (% of initial concentration) | | 100.00 | 96.57 | 92.84 |
| % Cis-cannabidiol | 1.454 | 0.04 | 0.03 | 0.03 |
| % Delta-9-tetrahydrocannabinol | 1.762 | 0.03 | 0.13 | 0.62 |
| % Unknown Impurity | 0.392 | ND | 0.06 | 0.14 |
| | 0.478 | ND | 0.22 | 0.64 |
| | 0.501 | BQL | 0.41 | 0.84 |
| | 0.610 | ND | BQL | 0.05 |
| | 0.670 | ND | BQL | 0.05 |
| | 0.792 | ND | 0.38 | 1.15 |
| | 0.821 | ND | 0.12 | 0.30 |
| | 0.931 | ND | 0.05 | 0.19 |
| | 0.956 | ND | 0.09 | 0.21 |
| | 2.068 | BQL | 0.11 | 0.23 |
| | 3.251 | ND | BQL | 0.09 |
| | 3.754 | ND | ND | 0.13 |
| Total Impurities (% Area) | | 0.07 | 1.60 | 4.67 |

ND - Not Detected
BQL - Below Quantification Limit, for unknown impurity only

TABLE 22

Stability Data for Cannabidiol Oral Solution Formulation # A7 stored at 40° C. ± 2° C. under 75% ± 5% relative humidity

| 40° C.-Formulation # A9 | RRT | 0 Week | 2 Weeks | 4 Weeks |
|---|---|---|---|---|
| Assay (% of initial concentration) | | 100.00 | 99.77 | 100.65 |
| % Cis-cannabidiol | 1.440 | 0.01 | 0.01 | 0.01 |
| % Trans-(1R,6R)-3'-methyl-cannabidiol | 1.841 | 0.05 | 0.06 | 0.05 |
| % Unknown Impurity | 0.770 | 0.06 | 0.07 | 0.08 |
| Total Impurities (% Area) | | 0.12 | 0.14 | 0.14 |

TABLE 23

Stability Data for Cannabidiol Oral Solution Formulation # A8 stored at 40° C. ± 2° C. under 75% ± 5% relative humidity

| 40° C.-Formulation # A10 | RRT | 0 Week | 2 Weeks | 4 Weeks |
|---|---|---|---|---|
| Assay (% of initial concentration) | | 100.00 | 101.25 | 100.78 |
| % Cis-cannabidiol | 1.440 | 0.01 | 0.01 | 0.01 |
| % Delta-9-tetrahydrocannabinol | 1.723 | ND | ND | 0.01 |
| % Trans-(1R,6R)-3'-methyl-cannabidiol | 1.842 | 0.05 | 0.05 | 0.05 |
| % Unknown Impurity | 0.770 | 0.07 | 0.07 | 0.06 |
| Total Impurities (% Area) | | 0.13 | 0.13 | 0.13 |

ND-Not Detected

Control formulation (#A5) showed significant increase in levels of total impurities and decrease in the assay value. The addition of antioxidants, Vitamin E and ascorbyl palmitate (see #A6) significantly increased the stability of formulation. These results illustrate the critical role of antioxidants in stabilizing cannabinoid formulations. Antioxidants Vitamin E and ascorbic acid (or its salt) show excellent synergism as ascorbic acid (or its salt) strongly inhibits the depletion of Vitamin E by regenerating it. Along with the antioxidants, the addition of pH modifiers to adjust the pH to the range of 6 to 7 resulted in exceptionally stable formulations (#A7 and #A8). The stability testing data illustrates that the pH range of from about 6 to about 7 is critical. Formulations #A9 and #A10 also showed good stability after four weeks.

Example 5. Lipid Formulations

The formulations in Table 24 were created by mixing all the solid and liquid excipients in the lipid. Cannabidiol was then dissolved. Synthetically synthesized, substantially pure, cannabidiol used as the source of the cannabinoid. Strawberry was used as the source of flavoring.

TABLE 24

Formulations with Lipids

| Formulation | #LF1 | #LF2 | #LF3 | #LF4 | #LF5 | #LF6 | #LF7 | #LF8 |
|---|---|---|---|---|---|---|---|---|
| Cannabinoid | 24.6 | 19.5 | 19.5 | 19.5 | 19.5 | 18 | 28 | 18 |
| Vitamin E (Alpha Tocopherol) | | 0.05 | 0.05 | 0.05 | 0.05 | 0.05 | 0.05 | |
| Flavor | | 0.3 | 0.3 | 0.3 | 0.3 | 0.3 | | |
| Sesame oil | 75.4 | 80.15 | 70.15 | | | | | |
| Sunflower oil | | | | 80.45 | | | | |
| Soybean oil | | | | | | 81.95 | | |
| Corn Oil | | | | | 80.45 | | | |
| Olive Oil | | | | | | | | 82.00 |
| Caprylic/Capric Triglyceride (Miglyol ® 812N) | | | | | | | 61.95 | |
| Ethanol | | | 10.0 | | | | 10.0 | |

TABLE 25

Additional Formulations with Lipids

| Formulation | #LF9 | #LF10 | #LF11 | #LF12 | #LF13 | #LF14 | #LF15 | #LF16 |
|---|---|---|---|---|---|---|---|---|
| Cannabinoid | 31.09 | 31.09 | 31.09 | 31.09 | 31.09 | 31.09 | 31.09 | 31.09 |
| Ascorbyl palmitate | | | | | 0.1 | 0.1 | 0.1 | 0.1 |
| Vitamin E (Alpha Tocopherol) | 0.1 | 0.2 | 0.5 | 1.0 | | 0.1 | | |
| Flavor | | 0.3 | 0.3 | | 0.3 | 0.3 | 0.3 | 0.3 |
| Saccharin | 0.025 | 0.025 | 0.025 | 0.025 | 0.025 | 0.025 | 0.025 | 0.025 |
| Caprylic/Capric Triglyceride (Miglyol ® 812N) | 68.785 | 68.385 | 68.085 | 67.885 | 67.485 | 67.385 | 63.485 | 58.485 |
| Ethanol | | | | | 1.0 | 1.0 | 5.0 | 10.0 |

| Formulation | #LF17 | #LF18 | #LF19 | #LF20 | #LF21 | #LF22 | #LF23 | #LF24 |
|---|---|---|---|---|---|---|---|---|
| Cannabinoid | 31.09 | 31.09 | 31.09 | 31.09 | 31.09 | 31.09 | 31.09 | 31.09 |
| BHA | 0.05 | 0.05 | 0.05 | | 0.05 | 0.05 | 0.1 | 0.01 |
| BHT | 0.01 | 0.01 | 0.01 | | 0.01 | 0.01 | 0.1 | 0.005 |
| TBHQ | | | | 0.02 | 0.02 | | | |
| Propyl gallate | | | 0.02 | | | | | |
| EDTA | | | | | | 0.05 | | |
| Ascorbyl palmitate | | | | | | | | |
| Linoleic acid | | | | | | | | |
| Propylparaben | | | | | | | | |
| Methylparaben | | | | | | | | |
| Vitamin E (Alpha Tocopherol) | 0.05 | | | | | | | |
| Flavor | | | | | | | 0.3 | 0.3 |
| Saccharin | 0.025 | 0.025 | 0.025 | 0.025 | 0.025 | 0.025 | 0.025 | 0.025 |
| Caprylic/Capric Triglyceride (Miglyol ® 812N) | 68.775 | 68.825 | 68.805 | 68.865 | 68.805 | 68.775 | 68.385 | 68.57 |
| Miglyol ® 840 | | | | | | | | |
| Olive Oil | | | | | | | | |
| Ethanol | | | | | | | | |

| Formulation | #LF25 | #LF26 | #LF27 | #LF28 | #LF29 | #LF30 | #LF31 | #LF32 |
|---|---|---|---|---|---|---|---|---|
| Cannabinoid | 31.09 | 31.09 | 31.09 | 31.09 | 31.09 | 31.09 | 31.09 | 31.09 |
| BHA | | 0.01 | | | | | | |
| BHT | 0.005 | | | | | | | |
| TBHQ | | | | | | | | |
| Propyl gallate | | | | | | | | |
| EDTA | | | | | | | | |
| Ascorbyl palmitate | | | | 4 | 0.05 | | 0.02 | 0.02 | 0.02 |
| Linoleic acid | | | 4 | 4 | 10 | | | |
| Propylparaben | | | | | | | | |
| Methylparaben | | | | | | | | |
| Vitamin E (Alpha Tocopherol) | | | | | | | | |

TABLE 25-continued

Additional Formulations with Lipids

| | | | | | | | | |
|---|---|---|---|---|---|---|---|---|
| Flavor | 0.3 | 0.3 | 0.3 | 0.3 | 0.3 | 0.3 | 0.3 | 0.3 |
| Saccharin | 0.025 | 0.025 | 0.025 | 0.025 | 0.025 | 0.025 | 0.025 | 0.025 |
| Caprylic/Capric Triglyceride (Miglyol ® 812N) | 68.58 | 68.575 | 64.585 | 64.535 | 58.585 | 68.565 | 63.565 | 58.565 |
| Miglyol ® 840 | | | | | | | | |
| Olive Oil | | | | | | | | |
| Ethanol | | | | | | 1 | 5 | 10 |

| Formulation | #LF33 | #LF34 | #LF35 | #LF36 | #LF37 | #LF38 | #LF39 | #LF40 |
|---|---|---|---|---|---|---|---|---|
| Cannabinoid | 31.09 | 31.09 | 31.09 | 31.09 | 31.09 | 31.09 | 18 | 18 |
| BHA | | | 0.05 | 0.05 | | | 0.01 | |
| BHT | | 0.05 | | 0.01 | | | 0.05 | 0.05 |
| TBHQ | | | | | | | | |
| Propyl gallate | | | | | | | | |
| EDTA | | | | | | | | |
| Ascorbyl palmitate | 0.02 | 0.02 | | | | | | |
| Linoleic acid | | | | | | | | |
| Propylparaben | | | | | | 0.01 | | |
| Methylparaben | | | | | | 0.1 | | |
| Vitamin E (Alpha Tocopherol) | 0.05 | | | | 0.2 | 0.2 | | |
| Flavor | 0.3 | 0.3 | 0.3 | | 0.3 | 0.3 | | |
| Saccharin | 0.025 | 0.025 | | 0.025 | 0.025 | 0.025 | | |
| Caprylic/Capric Triglyceride (Miglyol ® 812N) | 63.515 | 63.515 | 68.55 | | 68.385 | 68.275 | | |
| Miglyol ® 840 | | | | 68.825 | | | | |
| Olive Oil | | | | | | | 81.94 | 81.95 |
| Ethanol | 5 | 5 | | | | | | |

| Formulation | | #LF41 | | | | #LF42 | | |
|---|---|---|---|---|---|---|---|---|
| Cannabinoid | | 10.53 | | | | 10.98 | | |
| BHA | | | | | | | | |
| BHT | | | | | | | | |
| TBHQ | | | | | | | | |
| Propyl gallate | | | | | | | | |
| EDTA | | | | | | | | |
| Ascorbyl palmitate | | | | | | | | |
| Linoleic acid | | | | | | | | |
| Propylparaben | | | | | | | | |
| Sucralose | | | | | | 0.05 | | |
| Vitamin E (Alpha Tocopherol) | | 0.2 | | | | | | |
| Flavor | | 0.3 | | | | 0.02 | | |
| Saccharin | | 0.025 | | | | | | |
| Caprylic/Capric Triglyceride (Miglyol ® 812N) | | 88.945 | | | | | | |
| Sesame oil | | | | | | 80.28 | | |
| Olive Oil | | | | | | | | |
| Ethanol | | | | | | 8.67 | | |

Example 6. Stability of a Formulation with Lipids

Formulation #LF1 was subjected to stability at 25° C.±2° C. under 60%±5% relative humidity and 40° C.±2° C. under 75%±5% relative humidity. Formulations #LF10 and #LF11 were subjected to stability at 55° C.±2° C. and 40° C.±2° C. under 75%±5% relative humidity. Formulations #LF8, #LF9 and #LF12-#LF15 were subjected to stability at all 3 storage conditions. The stability of the formulation was analyzed at specified time points by evaluating the potency (assay value) and impurity levels. Assay and impurities were detected using high-performance liquid chromatography with an ultraviolet detector. The assay was performed at 228 nm and indicated as a % of initial concentration. For all impurities, analysis was performed at 228 nm and expressed as a % area. Amounts of particular impurities are listed in Table 25 as a percentage of area of each formulation along with amount of total impurities. Relative retention time (RRT) is given for each impurity.

TABLE 26

Three Month Stability Data for Cannabidiol Oral Solution Formulation #LF1 stored at 40° C. ± 2° C. under 75% ± 5% relative humidity and stored at 25° C. ± 2° C. under 60% ± 5% relative humidity

| Formulation #LF1 | RRT | 0 Month | 3 Months- 40° C. | 3 Months- 25° C. |
|---|---|---|---|---|
| Assay (% of initial concentration) | | 100.00 | 100.87 | 100.72 |
| % Cis-cannabidiol | 1.437 | 0.03 | 0.04 | 0.04 |
| % Delta 9-THC | 1.736 | 0.06 | 0.06 | 0.08 |
| % Trans-(1R,6R)-3'-methyl-cannabidiol | 1.840 | 0.02 | 0.06 | 0.02 |
| Total Impurities (% Area) | | 0.11 | 0.16 | 0.14 |

TABLE 27

Stability Data for Cannabidiol Oral Solution Formulation #LF8 stored at 55° C. ± 2° C.

| 55° C.-Formulation #LF8 | RRT | T = 0 | 1 Week | 2 Week | 3 Week | 4 Week |
|---|---|---|---|---|---|---|
| Assay (% of Initial Concentration) | | 100.00 | 100.25 | 101.20 | 100.08 | 99.41 |
| % Cis-cannabidiol | 1.450 | 0.06 | 0.05 | 0.05 | 0.05 | 0.05 |
| % Delta 9-THC | 1.752 | ND | 0.02 | 0.01 | 0.03 | 0.02 |
| % Trans-(1R, 6R)-3'-methyl-cannabidiol | 1.862 | 0.06 | 0.06 | 0.07 | 0.06 | 0.06 |
| % Total Impurities (% Area) | | 0.12 | 0.13 | 0.13 | 0.14 | 0.13 |

ND—Not Detected

TABLE 28

Stability Data for Cannabidiol Oral Solution Formulation #LF9 stored at 55° C. ± 2° C.

| 55° C.-Formulation #LF9 | RRT | T = 0 | 1 Week | 2 Week | 3 Week | 4 Week |
|---|---|---|---|---|---|---|
| Assay (% of Initial Concentration) | | 100.00 | 100.69 | 101.01 | 98.88 | 97.63 |
| % Cannabinol | 1.395 | ND | ND | ND | ND | 0.01 |
| % Cis-cannabidiol | 1.450 | 0.01 | 0.01 | 0.02 | 0.02 | 0.02 |
| % Delta 9-THC | 1.749 | ND | ND | ND | 0.03 | 0.04 |
| % Trans-(1R,6R)-3'-methyl-cannabidiol | 1.862 | 0.05 | 0.06 | 0.04 | 0.04 | ND |
| % Unknown Impurity | 0.396 | ND | BQL | BQL | 0.05 | 0.06 |
| | 0.455 | ND | BQL | 0.06 | 0.09 | 0.11 |
| | 0.480 | ND | 0.11 | 0.18 | 0.32 | 0.39 |
| | 0.499 | ND | 0.07 | 0.11 | 0.18 | 0.23 |
| | 0.520 | ND | BQL | BQL | 0.07 | 0.08 |
| | 0.584 | ND | BQL | BQL | 0.07 | 0.09 |
| | 0.771 | 0.07 | 0.07 | 0.07 | 0.05 | 0.05 |
| | 0.796 | ND | 0.09 | 0.21 | 0.40 | 0.60 |
| | 0.824 | ND | 0.05 | 0.09 | 0.10 | 0.11 |
| | 0.853 | ND | BQL | BQL | BQL | 0.06 |
| | 0.920 | ND | ND | BQL | BQL | 0.05 |
| | 1.908 | ND | BQL | 0.06 | 0.13 | 0.22 |
| Total Impurities (% Area) | | 0.13 | 0.46 | 0.84 | 1.55 | 2.12 |

ND - Not Detected
BQL - Below Quantification Limit

TABLE 29

Stability Data for Cannabidiol Oral Solution Formulation #LF10 stored at 55° C. ± 2° C.

| 55° C.-Formulation #LF10 | RRT | T = 0 | 2 Week | 4 Weeks |
|---|---|---|---|---|
| Assay (% of Initial Concentration) | | 100.00 | 98.35 | 97.12 |
| % Cis-cannabidiol | 1.450 | 0.01 | 0.01 | ND |
| % Delta 9-THC | 1.746 | ND | 0.04 | ND |
| % Trans-(1R,6R)-3'-methyl-cannabidiol | 1.862 | 0.04 | 0.04 | ND |
| % Unknown Impurity | 0.398 | ND | BQL | BQL |
| | 0.457 | ND | 0.09 | 0.10 |
| | 0.483 | ND | 0.22 | 0.36 |
| | 0.508 | ND | 0.12 | 0.17 |
| | 0.587 | ND | 0.05 | 0.05 |
| | 0.771 | 0.06 | 0.05 | BQL |
| | 0.796 | ND | 0.29 | 0.59 |
| | 0.823 | ND | 0.06 | 0.05 |
| | 1.895 | ND | 0.10 | 0.07 |
| | 18.000 | ND | ND | ND |
| Total Impurities (% Area) | | 0.11 | 1.07 | 1.39 |

ND-Not Detected
BQL-Below Quantification Limit

TABLE 30

Stability Data for Cannabidiol Oral Solution Formulation stored at 55° C. ± 2° C.

| 55° C.-Formulation #LF11 | RRT | T = 0 | 2 Week | 4 Weeks |
|---|---|---|---|---|
| Assay (% of Initial Concentration) | | 100.00 | 98.96 | 95.50 |
| % Cis-cannabidiol | 1.450 | 0.01 | 0.01 | 0.01 |
| % Delta 9-THC | 1.751 | ND | 0.02 | 0.01 |
| % Trans-(1R,6R)-3'-methyl-cannabidiol | 1.862 | 0.04 | 0.05 | 0.03 |
| % Unknown Impurity | 0.397 | ND | 0.06 | 0.11 |
| | 0.482 | ND | 0.17 | 0.35 |
| | 0.507 | ND | 0.13 | 0.24 |
| | 0.771 | 0.06 | 0.05 | 0.05 |
| | 0.795 | ND | 0.32 | 0.74 |
| | 0.823 | ND | 0.09 | 0.10 |
| Total Impurities (% Area) | | 0.11 | 0.90 | 1.64 |

ND - Not Detected
BQL - Below Quantification Limit

TABLE 31

Stability Data for Cannabidiol Oral Solution Formulation #LF12 stored at 55° C. ± 2° C.

| 55° C.-Formulation #LF12 | RRT | T = 0 | 1 Week | 2 Week | 3 Week | 4 Week |
|---|---|---|---|---|---|---|
| Assay (% of Initial Concentration) | | 100.00 | 99.94 | 100.87 | 100.85 | 99.58 |
| % Cannabinol | 1.395 | ND | ND | ND | ND | 0.01 |
| % Cis-cannabidiol | 1.450 | 0.01 | 0.01 | 0.01 | 0.01 | 0.01 |
| % Delta 9-THC | 1.749 | ND | ND | ND | 0.05 | 0.06 |
| % Trans-(1R,6R)-3'-methyl-cannabidiol | 1.862 | 0.05 | 0.07 | 0.05 | 0.05 | 0.05 |
| % Unknown Impurity | 0.396 | ND | BQL | BQL | 0.06 | 0.08 |
| | 0.479 | ND | 0.06 | 0.10 | 0.15 | 0.23 |
| | 0.499 | ND | BQL | BQL | 0.09 | 0.11 |
| | 0.584 | ND | BQL | BQL | 0.07 | 0.10 |
| | 0.771 | 0.07 | 0.07 | 0.07 | 0.06 | 0.07 |
| | 0.796 | ND | 0.06 | 0.14 | 0.21 | 0.34 |
| | 0.824 | ND | ND | 0.05 | BQL | 0.06 |
| Total Impurities (% Area) | | 0.13 | 0.27 | 0.42 | 0.75 | 1.12 |

ND - Not Detected
BQL - Below Quantification Limit

TABLE 32

Stability Data for Cannabidiol Oral Solution Formulation #LF13 stored at 55° C. ± 2° C.

| 55° C. - Formulation #LF13 | RRT | T = 0 | 1 Week | 2 Week | 3 Week | 4 Week |
|---|---|---|---|---|---|---|
| Assay (% of Initial Concentration) | | 100.00 | 99.09 | 100.73 | 99.39 | 99.35 |
| % Cis-cannabidiol | 1.450 | 0.05 | 0.05 | 0.05 | 0.05 | 0.05 |
| % Delta 9-THC | 1.752 | 0.01 | ND | 0.02 | 0.03 | 0.03 |
| % Trans-(1R,6R)-3'-methyl-cannabidiol | 1.862 | 0.06 | 0.05 | 0.06 | 0.06 | 0.06 |
| % Total Impurities (% Area) | | 0.12 | 0.10 | 0.13 | 0.14 | 0.14 |

ND - Not Detected

TABLE 33

Stability Data for Cannabidiol Oral Solution Formulation #LF14 stored at 55° C. ± 2° C.

| 55° C. - Formulation #LF14 | RRT | T = 0 | 1 Week | 2 Week | 3 Week | 4 Week |
|---|---|---|---|---|---|---|
| Assay (% of Initial Concentration) | | 100.00 | 100.99 | 99.20 | 100.89 | 100.24 |
| % Cis-cannabidiol | 1.450 | 0.05 | 0.05 | 0.05 | 0.05 | 0.05 |
| % Delta 9-THC | 1.752 | 0.01 | 0.01 | ND | 0.03 | 0.04 |
| % Trans-(1R,6R)-3'-methyl-cannabidiol | 1.862 | 0.06 | 0.06 | 0.08 | 0.06 | 0.07 |
| % Total Impurities (% Area) | | 0.12 | 0.12 | 0.13 | 0.14 | 0.16 |

ND - Not Detected

TABLE 34

Stability Data for Cannabidiol Oral Solution Formulation #LF15 stored at 55° C. ± 2° C.

| 55° C. - Formulation #LF15 | RRT | T = 0 | 1 Week | 2 Week | 3 Week | 4 Week |
|---|---|---|---|---|---|---|
| Assay (% of Initial Concentration) | | 100.00 | 101.11 | 101.70 | 100.44 | 100.70 |
| % Cis-cannabidiol | 1.450 | 0.05 | 0.05 | 0.05 | 0.05 | 0.05 |
| % Delta 9-THC | 1.752 | 0.01 | 0.01 | 0.02 | 0.03 | 0.03 |
| % Trans-(1R,6R)-3'-methyl-cannabidiol | 1.862 | 0.06 | 0.06 | 0.06 | 0.06 | 0.06 |
| % Total Impurities (% Area) | | 0.12 | 0.12 | 0.13 | 0.14 | 0.14 |

TABLE 35

Stability Data for Cannabidiol Oral Solution Formulation #LF8 stored at 40° C. ± 2° C. under 75% ± 5% relative humidity

| 40° C.—Formulation #LF8 | RRT | T = 0 | 1 Month | 2 Months | 3 Months |
|---|---|---|---|---|---|
| Assay (% of Initial Concentration) | | 100.00 | 99.74 | 99.75 | 101.93 |
| % Cis-cannabidiol | 1.450 | 0.06 | 0.05 | 0.05 | 0.05 |
| % Delta 9-THC | 1.752 | ND | ND | ND | 0.04 |
| % Trans-(1R,6R)-3'-methyl-cannabidiol | 1.862 | 0.06 | 0.06 | 0.08 | 0.06 |
| % Unknown Impurity | 1.197 | ND | BQL | BQL | 0.17 |
| % Total Impurities (% Area) | | 0.12 | 0.11 | 0.13 | 0.32 |

ND - Not Detected
BQL - Below Quantification Limit

TABLE 36

Stability Data for Cannabidiol Oral Solution Formulation #LF9 stored at 40° C. ± 2° C. under 75% ± 5% relative humidity

| 40° C.-Formulation #LF9 | RRT | T = 0 | 1 Week | 2 Week | 4 Week |
|---|---|---|---|---|---|
| Assay (% of Initial Concentration) | | 100.00 | 100.25 | 100.92 | 99.73 |
| % Cis-cannabidiol | 1.450 | 0.01 | 0.01 | 0.01 | 0.01 |
| % Delta 9-THC | 1.749 | ND | ND | ND | 0.04 |
| %Trans-(1R,6R)-3'-methyl-cannabidiol | 1.862 | 0.05 | 0.07 | 0.06 | 0.05 |
| % Unknown Impurity | 0.455 | ND | BQL | BQL | 0.05 |
| | 0.480 | ND | BQL | 0.09 | 0.22 |
| | 0.499 | ND | BQL | BQL | 0.13 |
| | 0.771 | 0.07 | 0.07 | 0.07 | 0.07 |
| | 0.796 | ND | BQL | BQL | 0.19 |
| | 0.823 | ND | ND | ND | 0.08 |
| Total Impurities (% Area) | | 0.13 | 0.15 | 0.23 | 0.84 |

ND-Not Detected
BQL-Below Quantification Limit

TABLE 37

Stability Data for Cannabidiol Oral Solution Formulation #LF10 stored at 40° C. ± 2° C. under 75% ± 5% relative humidity

| 40° C.-Formulation #LF10 | RRT | T = 0 | 2 Week | 4 Weeks |
|---|---|---|---|---|
| Assay (% of Initial Concentration) | | 100.00 | 100.33 | 99.74 |
| % Cis-cannabidiol | 1.450 | 0.01 | ND | 0.05 |
| % Delta 9-THC | 1.746 | ND | 0.02 | ND |
| % Trans-(1R,6R)-3'-methyl-cannabidiol | 1.862 | 0.04 | 0.04 | 0.06 |
| % Unknown Impurity | 0.483 | ND | 0.08 | 0.23 |
| | 0.508 | ND | 0.06 | 0.16 |
| | 0.771 | 0.06 | 0.06 | 0.05 |
| | 0.796 | ND | 0.13 | 0.43 |
| | 0.822 | ND | 0.05 | 0.10 |
| Total Impurities (% Area) | | 0.11 | 0.44 | 0.11 |

ND-Not Detected
BQL-Below Quantification Limit

TABLE 38

Stability Data for Cannabidiol Oral Solution Formulation #LF11 stored at 40° C. ± 2° C. under 75% ± 5% relative humidity

| 40C-Formulation #LF11 | RRT | T = 0 | 2 Weeks | 4 Weeks |
|---|---|---|---|---|
| Assay (% of Initial Concentration) | | 100.00 | 100.99 | 99.60 |
| % Cis-cannabidiol | 1.450 | 0.01 | 0.01 | 0.01 |
| % Delta 9-THC | 1.751 | ND | 0.02 | ND |
| % Trans-(1R,6R)-3'-methyl-cannabidiol | 1.862 | 0.04 | 0.04 | ND |
| % Unknown Impurity | 0.482 | ND | BQL | 0.05 |
| | 0.771 | 0.06 | 0.05 | 0.06 |
| | 0.795 | ND | BQL | 0.1 |
| Total Impurities (% Area) | | 0.11 | 0.12 | 0.22 |

ND-Not Detected

TABLE 39

Stability Data for Cannabidiol Oral Solution Formulation #LF12 stored at 40° C. ± 2° C. under 75% ± 5% relative humidity

| 40° C.-Formulation #LF12 | RRT | T = 0 | 1 Week | 2 Week | 4 Week |
|---|---|---|---|---|---|
| Assay (% of Initial Concentration) | | 100.00 | 100.04 | 100.54 | 100.65 |
| % Cis-cannabidiol | 1.450 | 0.01 | 0.01 | 0.01 | 0.01 |
| % Delta 9-THC | 1.749 | ND | ND | ND | 0.02 |
| % Trans-(1R,6R)-3'-methyl-cannabidiol | 1.862 | 0.05 | 0.06 | 0.05 | 0.05 |
| % Unknown Impurity | 0.771 | 0.07 | 0.07 | 0.07 | 0.07 |
| % Total Impurities (% Area) | | 0.13 | 0.14 | 0.13 | 0.15 |

ND -Not Detected

TABLE 40

Stability Data for Cannabidiol Oral Solution Formulation #LF13 stored at 40° C. ± 2° C. under 75% ± 5% relative humidity

| 40° C.-Formulation #LF13 | RRT | T = 0 | 1 Week | 2 Week | 4 Week |
|---|---|---|---|---|---|
| Assay (% of Initial Concentration) | | 100.00 | 101.52 | 101.13 | 99.79 |
| % Cis-cannabidiol | 1.450 | 0.05 | 0.06 | 0.05 | 0.05 |
| % Delta 9-THC | 1.752 | 0.01 | ND | 0.02 | 0.02 |
| % Trans-(1R,6R)-3'-methyl-cannabidiol | 1.862 | 0.06 | 0.06 | 0.06 | 0.06 |
| % Total Impurities (% Area) | | 0.12 | 0.12 | 0.13 | 0.13 |

ND -Not Detected

TABLE 41

Stability Data for Cannabidiol Oral Solution Formulation #LF14 stored at 40° C. ± 2° C. under 75% ± 5% relative humidity

| 40° C.-Formulation #LF14 | RRT | T = 0 | 1 Week | 2 Week | 4 Week |
|---|---|---|---|---|---|
| Assay (% of Initial Concentration) | | 100.00 | 101.16 | 99.75 | 100.47 |
| % Cis-cannabidiol | 1.450 | 0.05 | 0.05 | 0.05 | 0.05 |
| % Delta 9-THC | 1.752 | 0.01 | 0.01 | ND | 0.02 |
| % Trans-(1R,6R)-3'-methyl-cannabidiol | 1.862 | 0.06 | 0.06 | 0.06 | 0.06 |
| % Total Impurities (% Area) | | 0.12 | 0.12 | 0.11 | 0.13 |

ND-Not Detected

TABLE 42

Stability Data for Cannabidiol Oral Solution Formulation #LF15 stored at 40° C. ± 2° C. under 75% ± 5% relative humidity

| 40° C.-Formulation #LF15 | RRT | T = 0 | 1 Week | 2 Week | 4 Week |
|---|---|---|---|---|---|
| Assay (% of Initial Concentration) | | 100.00 | 96.78 | 100.68 | 100.94 |
| % Cis-cannabidiol | 1.450 | 0.05 | 0.06 | 0.05 | 0.05 |
| % Delta 9-THC | 1.752 | 0.01 | ND | 0.02 | 0.02 |
| % Trans-(1R,6R)-3'-methyl-cannabidiol | 1.862 | 0.06 | 0.06 | 0.06 | 0.07 |
| % Total Impurities (% Area) | | 0.12 | 0.12 | 0.13 | 0.14 |

ND-Not Detected

TABLE 43

Stability Data for Cannabidiol Oral Solution Formulation #LF8 stored at 25° C. ± 2° C. under 60% ± 5% relative humidity

| 25° C.-Formulation #LF8 | RRT | T = 0 | 1 Month | 2 Months | 3 Months |
|---|---|---|---|---|---|
| Assay (% of Initial Concentration) | | 100.00 | 100.12 | 101.11 | 102.02 |
| % Cis-cannabidiol | 1.450 | 0.06 | 0.05 | 0.05 | 0.05 |
| % Delta 9-THC | 1.752 | ND | 0.01 | ND | ND |
| % Trans-(1R,6R)-3'-methyl-cannabidiol | 1.862 | 0.06 | 0.07 | 0.07 | 0.06 |
| % Unknown Impurity | 1.197 | ND | ND | BQL | 0.17 |
| % Total Impurities (% Area) | | 0.12 | 0.13 | 0.12 | 0.22 |

ND-Not Detected
BQL-Below Quantification Limit

TABLE 44

Stability Data for Cannabidiol Oral Solution Formulation #LF9 stored at 25° C. ± 2° C. under 60% ± 5% relative humidity

| 25° C.-Formulation #LF9 | RRT | T = 0 | 4 Week |
|---|---|---|---|
| Assay (% of Initial Concentration) | | 100.00 | 100.14 |
| % Cis-cannabidiol | 1.450 | 0.01 | 0.01 |
| % Trans-(1R,6R)-3'-methyl-cannabidiol | 1.862 | 0.05 | 0.05 |
| % Unknown Impurity | 0.771 | 0.07 | 0.06 |
| Total Impurities (% Area) | | 0.13 | 0.12 |

TABLE 45

Stability Data for Cannabidiol Oral Solution Formulation #LF12 stored at 25° C. ± 2° C. under 60% ± 5% relative humidity

| 25° C.-Formulation #LF12 | RRT | T = 0 | 4 Week |
|---|---|---|---|
| Assay (% of Initial Concentration) | | 100.00 | 100.69 |
| % Cis-cannabidiol | 1.450 | 0.01 | 0.01 |
| % Trans-(1R,6R)-3'-methyl-cannabidiol | 1.862 | 0.05 | 0.05 |
| % Unknown Impurity | 0.771 | 0.07 | 0.07 |
| % Total Impurities (% Area) | | 0.13 | 0.13 |

TABLE 46

Stability Data for Cannabidiol Oral Solution Formulation #LF13 stored at 25° C. ± 2° C. under 60% ± 5 % relative humidity

| 25° C.-Formulation #LF13 | RRT | T = 0 | 4 Week |
|---|---|---|---|
| Assay (% of Initial Concentration) | | 100.00 | 99.83 |
| % Cis-cannabidiol | 1.450 | 0.05 | 0.05 |
| % Delta 9-THC | 1.752 | 0.01 | 0.01 |
| % Trans-(1R,6R)-3'-methyl-cannabidiol | 1.862 | 0.06 | 0.06 |
| % Total Impurities (% Area) | | 0.12 | 0.12 |

TABLE 47

Stability Data for Cannabidiol Oral Solution Formulation #LF14 stored at 25° C. ± 2° C. under 60% ± 5% relative humidity

| 25° C.-Formulation #LF14 | RRT | T = 0 | 4 Week |
|---|---|---|---|
| Assay (% of Initial Concentration) | | 100.00 | 100.64 |
| % Cis-cannabidiol | 1.450 | 0.05 | 0.05 |
| % Delta 9-THC | 1.752 | 0.01 | 0.01 |
| % Trans-(1R,6R)-3'-methyl-cannabidiol | 1.862 | 0.06 | 0.06 |
| % Total Impurities (% Area) | | 0.12 | 0.12 |

TABLE 48

Stability Data for Cannabidiol Oral Solution Formulation #LF15 stored at 25° C. ± 2° C. under 60% ± 5% relative humidity

| 25° C.-Formulation #LF15 | RRT | T = 0 | 4 Week |
|---|---|---|---|
| Assay (% of Initial Concentration) | | 100.00 | 100.38 |
| % Cis-cannabidiol | 1.450 | 0.05 | 0.05 |
| % Delta 9-THC | 1.752 | 0.01 | 0.01 |
| % Trans-(1R,6R)-3'-methyl-cannabidiol | 1.862 | 0.06 | 0.06 |
| % Total Impurities (% Area) | | 0.12 | 0.12 |

As seen in Table 25 above, formulation #LF1 with sesame oil showed good stability after 3 months at both storage conditions 25° C.±2° C./60%±5% relative humidity and 40° C.±2° C./75%±5% relative humidity. Also, formulation #LF8 with olive oil showed good stability after four weeks at storage conditions 55° C.±2° C., after three months at 25° C.±2° C./60%±5% relative humidity and 40° C.±2° C./75%±5% relative humidity.

Formulations #LF9-#LF15 each contain capyrlic/capric triglyceride and one of alpha-tocopherol (Vitamin E), ascorbyl palmitate, or a combination thereof as an antioxidant. Formulations #LF13-#LF15 each additionally contain ethanol. Each of formulations #LF9-#LF15 showed good stability after four weeks at storage conditions 55° C.±2° C., 40° C.±2° C./75%±5% relative humidity and 25° C.±2° C./60%±5% relative humidity. #LF9-#LF12 demonstrate the ability of alpha-tocopherol (Vitamin E) to surprisingly achieve less than 0.5% total impurities after four weeks at 40° C.±2° C./75%±5% relative humidity. #LF13-#LF15 demonstrate the ability of ascorbyl palmitate to surprisingly achieve less than 0.2% total impurities after four weeks at all 3 storage conditions in formulations containing from 1% to 5% ethanol. #LF14 demonstrates that the addition of alpha tocopherol (Vitamin E) does not improve the surprising stability from the use of ascorbyl palmitate.

Example 7. Paclitaxel Induced Neuropathic Pain Study

Paclitaxel is an antineoplastic agent that has activity against several types of cancer including ovary, breast, lung and the head and neck. Paclitaxel works by promoting microtubule assembly which results in neuropathy as a toxic side effect. Peripheral sensory neuropathy is the most commonly reported neurotoxic side effect of paclitaxel and it limits treatment with high and cumulative doses of paclitaxel when given alone or in combination with other neurotoxic antineoplastic agents such as cisplatin. Currently there is not a highly effective treatment for this type of pain. Therefore, there is a need for a highly effective treatment to relieve the symptoms of paclitaxel induced neuropathy.

A mouse study was conducted in order to determine the effects of cannabidiol, delta-9-tetrahydrocannabinol, and cannabidiol plus delta-9-tetrahydrocannabinol combinations to alleviate neuropathic pain caused by chemotherapy-induced peripheral neuropathy. The cannadidiol administered to the mice was substantially pure, synthetically synthesized, cannabidiol which had a purity greater than 98%.

A detailed explanation of FIG. 1 is as follows. The Y-axes represent the threshold sensitivity to mechanical stimulation, expressed as a percent of baseline sensitivity. The X-axes represent the dose of drug in milligrams per kilogram ("mg/kg") administered intraperitoneally ("IP".) Whereas the dotted lines represent withdrawal threshold level to mechanical stimulation of saline controls, the dashed lines represent paclitaxel-treated animals. The points along the dashed line indicate neuropathic pain while points along the dotted line represent protection from neuropathic pain. The data shown are mean+SEM sensitivity measured on Day 21 post treatment. *$p<0.05$ from saline control as determined by one-way ANOVA.

Specific doses of agents producing similar overt behavioral effects when added to together should produce the additive effect level.

Examples

1) If 1.25 mg/kg cannabidiol produces 100% alleviation of pain effect and 1.25 mg/kg delta-9-tetrahydrocannabinol produces 0% effect, then those doses added together should be fully effective (as should the 2.5 mg/kg cannabidiol+2.5 mg/kg delta-9-tetrahydrocannabinol).
2) If 0.625 mg/kg cannabidiol and 0.625 delta-9-tetrahydrocannabinol produce 0% effect, then those doses in combination should be ineffective.

Applicant found (as illustrated in FIG. 1) that cannabidiol when administered alone provided the most effective level of alleviating chemotherapy-induced neuropathic pain compared to delta-9-tetrahydrocannabinol. The presence of delta-9-tetrahydrocannabinol depending on its concentration can inhibit the ability of cannabidiol to alleviate neuropathic pain. The ability of delta-9-tetrahydrocannabinol to block the pain alleviating activity of cannabidiol is also dependent of the concentration of cannabidiol. This test illustrates that a substantially pure cannabidiol formulation is highly desirable.

Example 8. Additional Paclitaxel Induced Neuropathic Pain Study

Methods

Paclitaxel was administered on days 1, 3, 5, and 7 following baseline mechanical sensitivity, and cannabinoids were administered 15 minutes prior to each paclitaxel injection. Mechanical sensitivity was then reassessed on days 9, 14, and 21. For mechanical sensitivity testing, mice are placed on a wire mesh surface inside individual clear Plexiglas chambers, and the plantar surface of their hindpaw is touched with increasing thicknesses of Von Frey filaments (0.16-2.0 grams of force) until they withdraw their paw from the stimulation. Von Frey hairs are a series of fine, calibrated filaments that are pressed against the plantar surface of the mouse into a bent "C" shape for 6 seconds. For each treatment group the final sample size was 8 animals. Two-way ANOVA were used to determine significant effects of CBD and THC treatment.

Single agent dose effect curves are shown as percent level of mechanical sensitivity at baseline to normalize data. Dose equivalence analysis was used to determine significant synergistic effects of CBD+THC compared with predicted additive values derived from single agent dose response curves. To obtain predicted and observed effect levels, data were transformed into percent maximal possible effect (MPE) of the cannabinoid to reverse paclitaxel-induced mechanical sensitivity. To determine this value for each animal, the mean sensitivity score of the paclitaxel control group on given test day is set at zero and the animal's baseline score prior to treatment is set at 100. For example, if an animal has a mechanical sensitivity score of 1.0 at baseline and a score of 0.75 on day 9, and the paclitaxel group shows an average score of 0.5 on day 9, then the animal's percent MPE score is 50%. A % MPE score of 0% would indicate that the animal was at least as sensitive as the paclitaxel control group. A % MPE score of 100% would indicate that the animal was as sensitive or less sensitive on test day as it was at baseline. This transformation of the data is necessary to determine effective dose levels (ED50s, ED25s, etc).

Results

Pretreatment with CBD or THC significantly attenuated paclitaxel-induced mechanical sensitivity, $P<0.0001$ for each agent. See FIG. 2. CBD produced this effect with higher potency, in that the minimal effective dose for CBD was 1.25 mg/kg IP, while the minimal effective dose for THC was 2.5 mg/kg IP. Two-way ANOVA also revealed a significant difference between the CBD and THC dose response curves, with the 1.25 mg/kg dose of CBD producing a significantly higher % baseline score as compared to 1.25 mg/kg dose of THC. Both drugs appeared to be efficacious.

Across a wider range of doses, it becomes apparent that both CBD and THC do not produce monotonic dose effects but instead follow an inverted-U or N shaped function. For both CBD and THC at each time point, the curve turns over at between 5.0 and 10 mg/kg, but the treatments regain efficacy at higher doses. See FIG. 3, top center and middle center panels. In the combination groups, the data appear more U-shaped, although it is unclear whether the rise would again emerge with larger dose combinations. See FIG. 3, bottom middle panel.

Dose equivalence analysis was used to predict the combined effects of CBD and THC based on their effects alone on the ascending limbs of their dose response curves. The individual dose effect equations are $E=78.47D^{2.5}/D^{2.5}+0.497$ for CBD, and $E=80D^3/D^3+3.44$ for THC. In dose equivalence analysis, for each CBD dose, an effect-equivalent dose of THC is identified. This dose is added to the actual THC dose in each combination so that the sum is the effective dose of the predicted combination. For example, to predict the additive effect of 0.31 mg/kg CBD and 0.31 mg/kg THC, a dose of THC is identified that is equi-effective to 0.31 mg/kg CBD using the determined dose effect equation for CBD. CBD 0.31 mg/kg produces a % MPE of 8.3%. From this, the dose of THC to produce a % MPE of 8.3 is calculated using the determined dose effect equation for THC. The dose of THC required to achieve a % MPE is 0.7 mg/kg, and this represents a dose that is equi-effective to 0.31 mg/kg CBD. The 0.7 mg/kg is added to the 0.31 mg/kg to give 1.01 mg/kg THC, whose effect level will equal the predicted effect level of 0.31 mg/kg CBD+0.31 mg/kg THC. This predicted effect level is determined to be 13.68% MPE.

Figure 2:
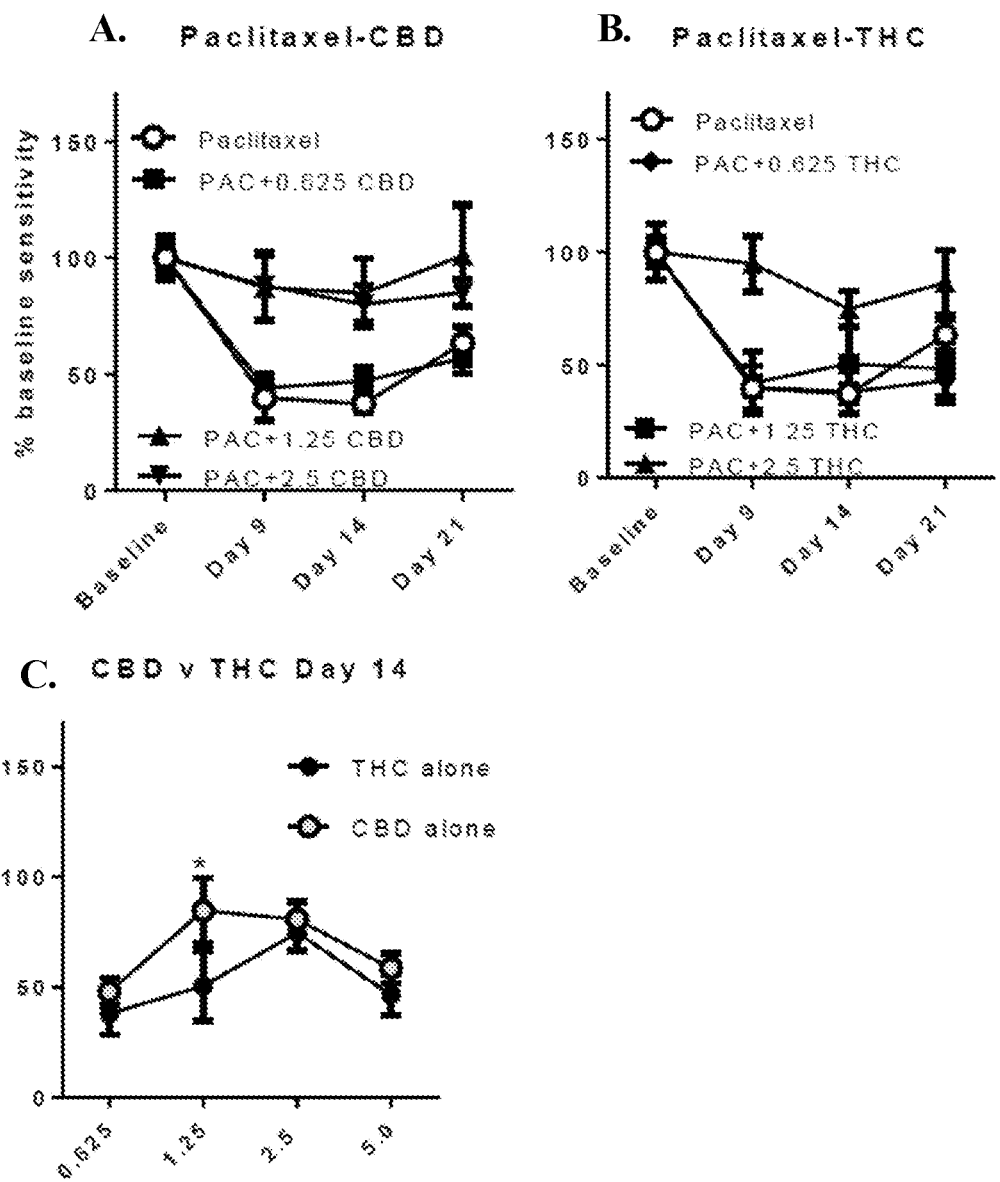
FIG. 2 shows the results from the study detailed in Example 8 and illustrates the advantages of administration of substantially pure, synthetically synthesized, cannabidiol formulations over THC formulations for treatment of neuropathic pain. Panel A. shows the results of Paclitaxel alone and the combination of Paclitaxel and CBD. Panel B. shows the results of Paclitaxel alone and the combination of Paclitaxel and HTC. Panel C. shows the results of CBD and THC alone at Day 14.
Figure 3:
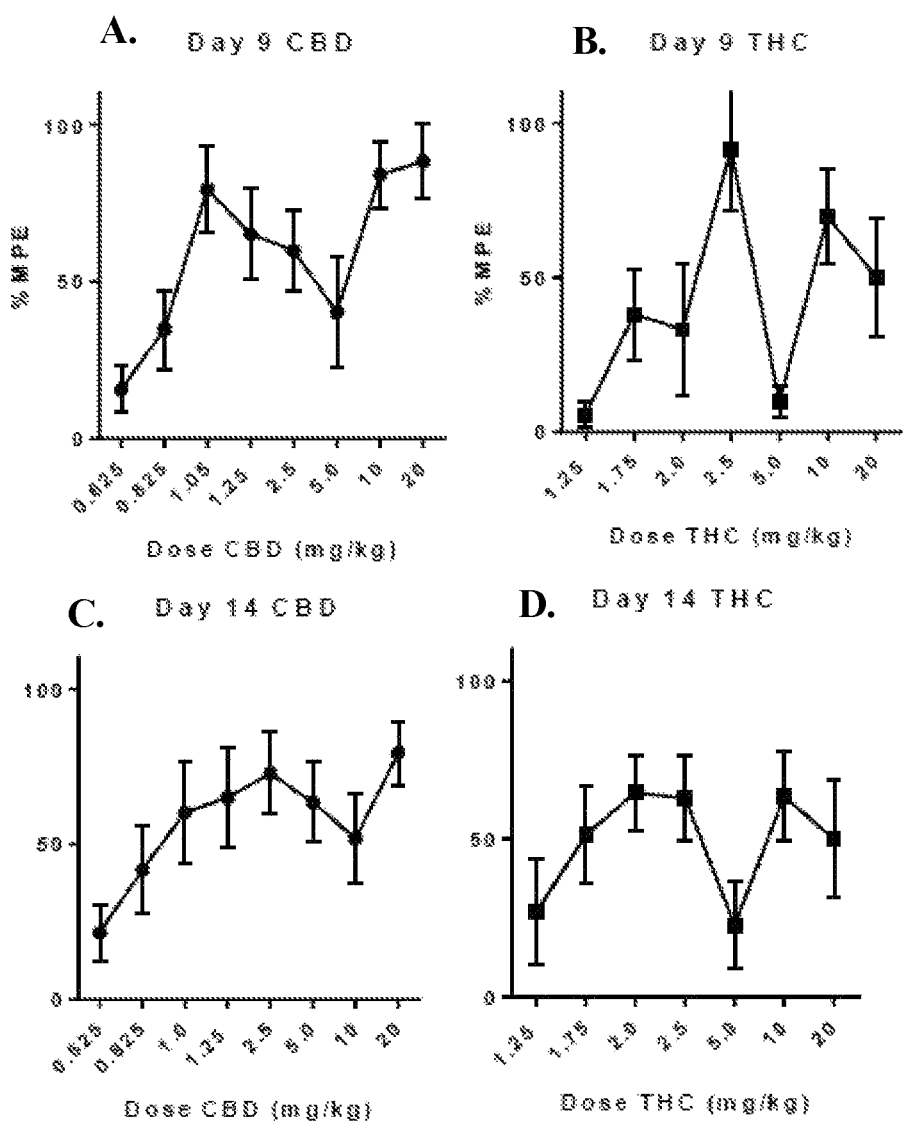
FIG. 3 shows further results from the study detailed in Example 8 and illustrates dose-dependent advantages of administration of substantially pure, synthetically synthesized, cannabidiol formulations over THC formulations for treatment of neuropathic pain. Panel A. shows the results of CBD at Day 9. Panel B. shows the results of THC at Day 9. Panel C. shows the results of CBD at Day 14. Panel D. shows the results of THC at Day 14. Panel E. shows the results of CBD at Day 21. Panel F. shows the results of THC at Day 21. Panel G. shows the results of the combination of THC and CBD at Day 9. Panel H. shows the results of the combination of THC and CBD at Day 14. Panel I. shows the results of the combination of THC and CBD at Day 21.
Figure 3:
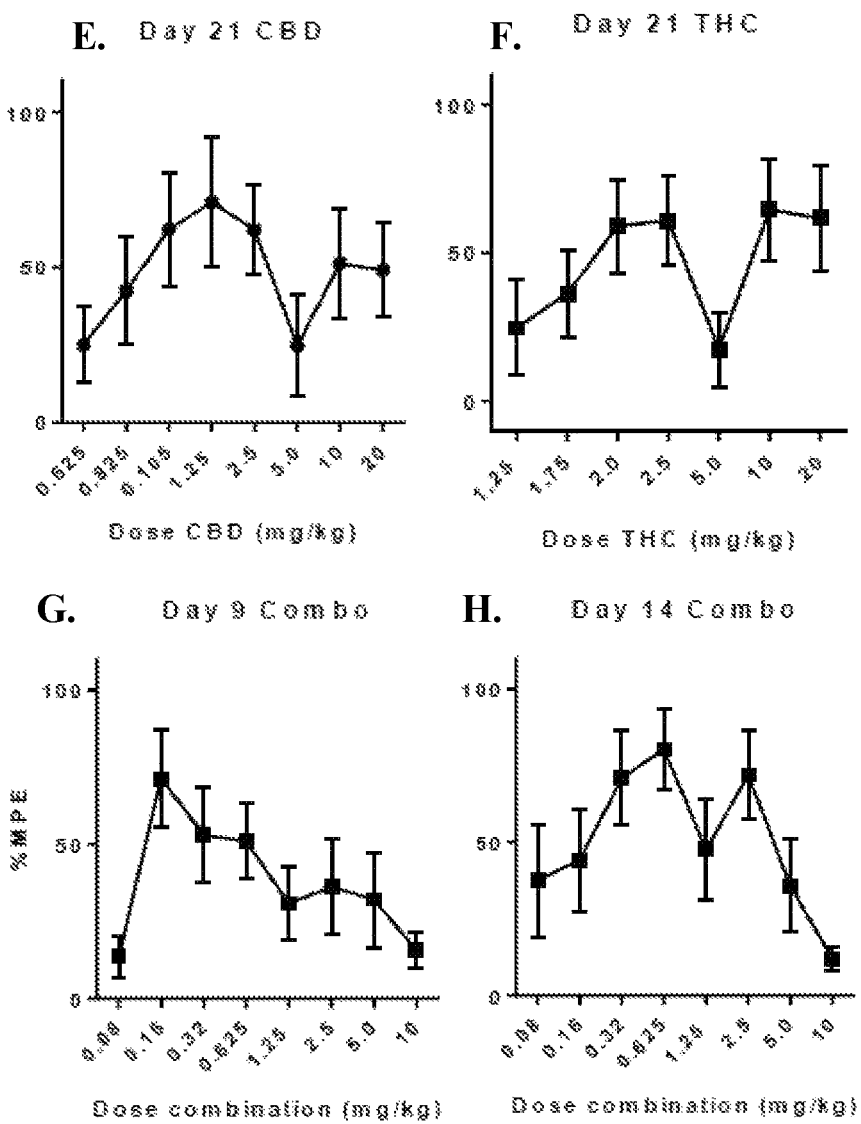
Figure 3:
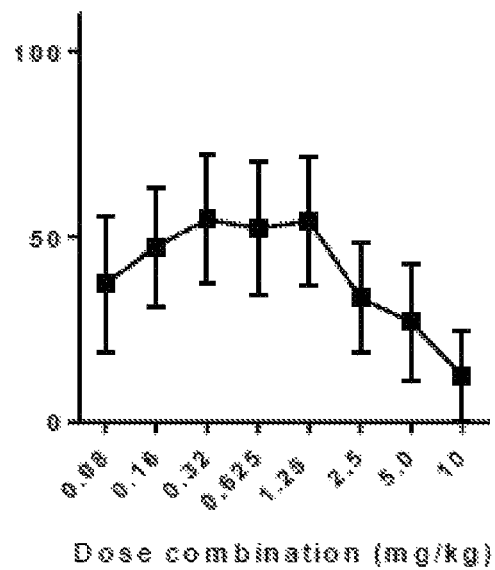
Figure 4:
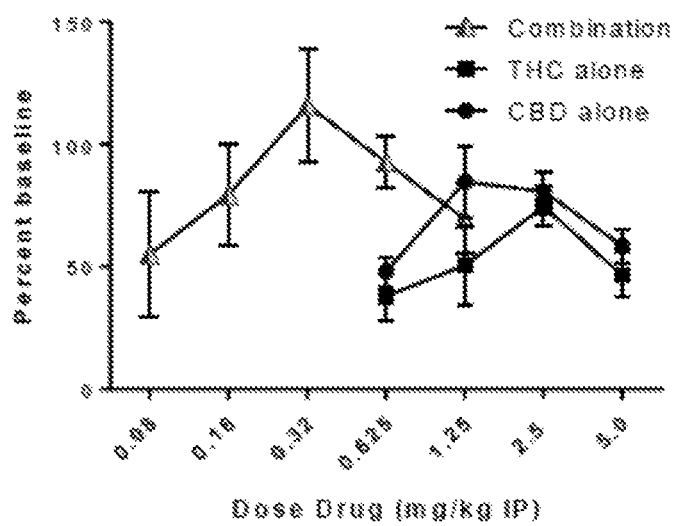
FIG. 4 shows further results from the study detailed in Example 8 and illustrates synergistic results of administration of substantially pure, synthetically synthesized, cannabidiol formulations and THC formulations for treatment of neuropathic pain.
Figure 5:
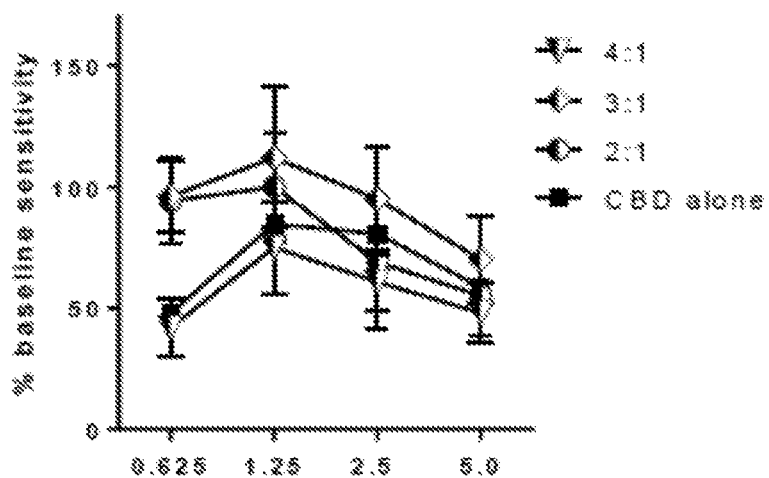
FIG. 5 shows the results from the study detailed in Example 9 and illustrates the advantages administration of higher ratio substantially pure, synthetically synthesized, cannabidiol to THC formulations for treatment of neuropathic pain. Panel A. shows the results of CBD alone and CBD-rich combinations of THC and CBD. Panel B. shows the results of THC alone and THC-rich combinations of CBD and THC.
Figure 5:
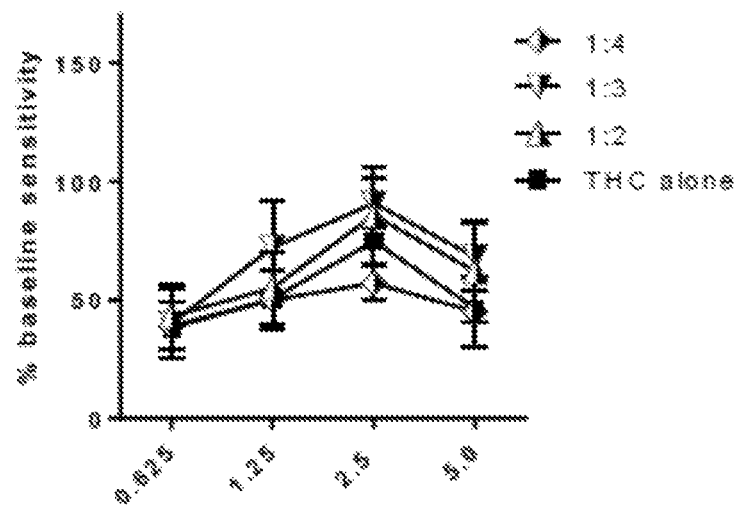
Figure 6:
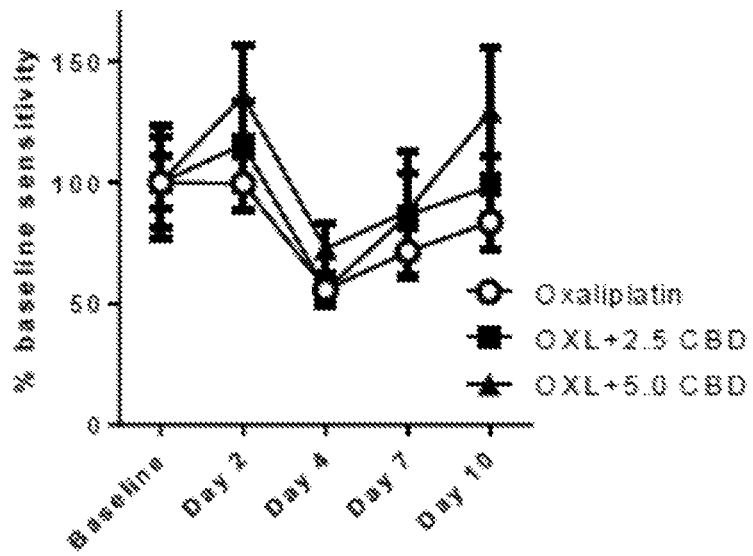
FIG. 6 shows the results from the study detailed in Example 10 and illustrates the advantages of administration of substantially pure, synthetically synthesized, cannabidiol formulations for treatment of neuropathic pain. Panel A. shows the results of Oxaliplatin alone and the combination of Oxaliplatin and CBD. Panel B. shows the results of Vincristine alone and the combination of Vincristine and CBD.
Figure 6:
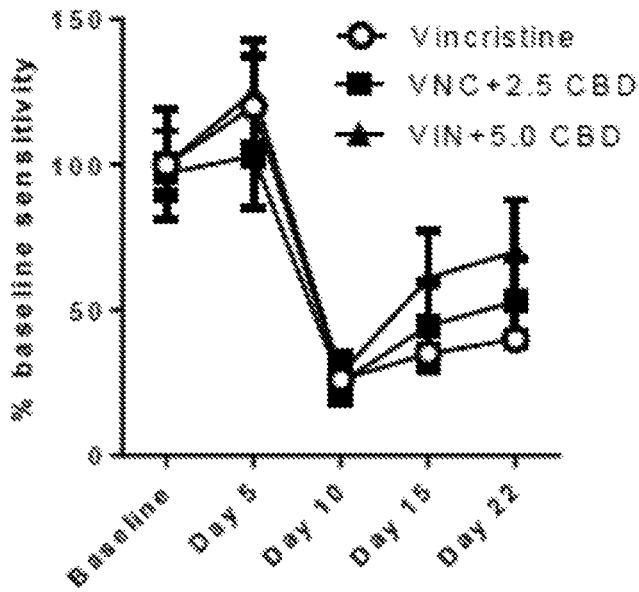

When the actual combination experiment was conducted, 0.31 mg/kg CBD+0.31 mg/kg THC (labeled on the graph as 0.625 mg/kg combination), was actually the ED78 (78% maximum possible effect; FIG. 2 bottom panel). Modified t-test statistics are applied and it was determined that the predicted combination dose response curve was statistically significantly different from the observed dose response curve, demonstrating a synergistic effect of CBD+THC combinations. See FIG. 4.

Example 9. Additional Paclitaxel Induced Neuropathic Pain Study

Methods

A study was designed to test the efficacy of CBD+THC combinations outside of the 1:1 dose ratio. Six additional combinations were tested: 4:1, 3:1, 2:1, 1:2, 1:3, and 1:4. Four doses of each treatment combination were tested in groups of mice treated with paclitaxel. For each treatment group the final sample size was 8 animals.

Results

The 4:1 combination of CBD to THC produced a similar effect to CBD alone, while 2:1 and 3:1 ratios of CBD to THC were more potent than CBD alone. See FIG. 5. Two-way ANOVA revealed an overall effect of treatment and of dose ($p<0.05$) but no significant interaction. Combinations higher in THC than in CBD produced an effect similar to THC alone, with a significant effect of dose ($p<0.05$) but no main effect of treatment and no significant interaction.

Example 10. Oxaliplatin or Vincristine Induced Neuropathic Pain Study

Methods

A study was designed to test the efficacy of CBD in preventing oxaliplatin- or vincristine-induced peripheral neuropathy. Two doses of CBD and vehicle were tested against each of these first line chemotherapeutic agents. Oxaliplatin was administered once at a dose of 6 mg/kg. CBD was administered 15 minutes prior to the single oxaliplatin injection. Vincristine was administered once daily for 7 days at a dose of 0.1 mg/kg. CBD was administered 15 minutes prior to each vincristine injection. For each treatment group the final sample size was 8 animals.

Results

Pretreatment with CBD attenuated oxaliplatin but not vincristine-induced mechanical sensitivity. See FIG. 6. Two-way ANOVA for oxaliplatin revealed a significant effect of time and a significant effect of treatment ($p<0.05$) and no significant interaction. Two-way ANOVA for vincristine revealed a significant effect of time ($p<0.05$), but no main effect of treatment and no interaction.

Example 11. Anticonvulsant Study

This study was conducted as follows according to standard models for anticonvulsant screening including the maximal electroshock test ("MES"), the minimal clonic seizure ("6 Hz") test and evaluations of toxicity ("TOX"). The data was recorded as number of animals protected (N) out of the number of animals tested (F), see Tables 26 to 29 below. The test was repeated one time. The cannabidiol administered to the mice and rats was substantially pure, synthetically synthesized, cannabidiol which had a purity greater than 98%. The cannabidiol was dissolved in 0.5% methylcellulose or a 1:1:18 ratio of ethanol:polyethoxylated castor oil:phosphate buffered saline ("PBS").

The maximal electroshock test is a model for generalized tonic-clonic seizures and provides an indication of a compound's ability to prevent seizure spread when all neuronal circuits in the brain are maximally active. These seizures are highly reproducible and are electrophysiologically consistent with human seizures. For all tests based on maximal electroshock convulsions, 60 Hz of alternating current (50 mA in mice, 150 in rats) was delivered for 0.2 s by corneal electrodes which were primed with an electrolyte solution containing an anesthetic agent (0.5% tetracaine HCl). The mice were tested at various intervals following doses of 10, 30 and 100 mg/kg of cannabidiol given by intraperitoneal injection of a volume of 0.01 mL/g. An animal was considered "protected" from maximal electroshock-induced seizures upon abolition of the hindlimb tonic extensor component of the seizure.

The minimal motor impairment test was used to determine the compounds' undesirable side effects or toxicity. During this test, the animals were monitored for overt signs of impaired neurological or muscular function. The rotorod procedure was used to disclose minimal muscular or neurological impairment. When a control mouse is placed on a rod that rotates at a speed of 6 rpm, the animal can maintain its equilibrium for long periods of time. The animal was considered toxic if it fell off this rotating rod three times during a 60 second period. In addition to minimal motor impairment, the animals may have exhibited a circular or zigzag gait, abnormal body posture and spread of the legs, tremors, hyperactivity, lack of exploratory behavior, somnolence, stupor, catalepsy, loss of placing response and changes in muscle tone.

The third test was the minimal clonic seizure (6 Hz) test. Like the maximal electroshock test, the minimal clonic seizure (6 Hz) test is used to assess a compound's efficacy against electrically induced seizures but uses a lower frequency (6 Hz) and longer duration of stimulation (3 s). Cannabidiol was pre-administered to mice via intraperitoneal injection. At varying times, individual mice (four per time point) were challenged with sufficient current delivered through corneal electrodes to elicit a psychomotor seizure in 97% of animals (32 mA for 3 s). Untreated mice will display seizures characterized by a minimal clonic phase followed by stereotyped, automatistic behaviors described originally as being similar to the aura of human patients with partial seizures. Animals not displaying this behavior are considered protected.

TABLE 49

Anticonvulsant Screening, Mice, Methylcellulose

| Test | Dose | Time (Hours) | | |
|---|---|---|---|---|
| | | 0.5 N/F | 1.0 N/F | 2.0 N/F |
| 6 HZ | 10 | 0/4 | 0/4 | 0/4 |
| 6 HZ | 30 | 0/4 | 0/4 | 0/4 |
| 6 HZ | 100 | 1/4 | 0/4 | 0/4 |
| MES | 10 | 0/4 | 0/4 | 0/4 |
| MES | 30 | 0/4 | 0/4 | 0/4 |
| MES | 100 | 0/4 | 1/4 | 2/4 |
| TOX | 10 | 0/8 | 0/8 | 0/8 |
| TOX | 30 | 0/8 | 0/8 | 0/8 |
| TOX | 100 | 0/8 | 0/8 | 0/8 |

TABLE 50

Anticonvulsant Screening, Mice, Ethanol:Polyethoxylated castor oil:PBS

| Test | Dose | Time (Hours) | | |
|---|---|---|---|---|
| | | 0.5 N/F | 1.0 N/F | 2.0 N/F |
| 6 HZ | 10 | 0/4 | 0/4 | 0/4 |
| 6 HZ | 30 | 0/4 | 0/4 | 0/4 |
| 6 HZ | 100 | 2/4 | 0/4 | 0/4 |
| MES | 10 | 0/4 | 0/4 | 0/4 |
| MES | 30 | 0/4 | 1/4 | 0/4 |
| MES | 100 | 0/4 | 2/4 | 1/4 |
| TOX | 10 | 0/8 | 0/8 | 0/8 |
| TOX | 30 | 0/8 | 0/8 | 0/8 |
| TOX | 100 | 0/8 | 0/8 | 0/8 |

TABLE 51

Anticonvulsant Screening, Rats, Methylcellulose

| Test | Dose | Time (Hours) | | |
|---|---|---|---|---|
| | | 1.0 N/F | 2.0 N/F | 4.0 N/F |
| MES | 30 | 0/4 | 0/4 | 0/4 |
| MES | 100 | 0/4 | 0/4 | 0/4 |
| TOX | 30 | 0/4 | 0/4 | 0/4 |
| TOX | 100 | 0/4 | 0/4 | 0/4 |

TABLE 52

Anticonvulsant Screening, Rats, Ethanol: Polyethoxylated castor oil:PBS

| Test | Dose | Time (Hours) | | |
|---|---|---|---|---|
| | | 1.0 N/F | 2.0 N/F | 4.0 N/F |
| MES | 30 | 0/4 | 0/4 | 0/4 |
| MES | 100 | 1/4 | 0/4 | 0/4 |
| TOX | 30 | 0/4 | 0/4 | 0/4 |
| TOX | 100 | 0/4 | 0/4 | 0/4 |

As seen in Tables 49 to 52 above, Applicant found that cannabidiol protected the mice and rats from epilepsy.

Example 12. 6 Hz Psychomotor Seizure Test

This study was conducted in order to determine the ability of synthetically-synthesized, substantially pure cannabidiol to block a psychomotor seizure induced by long-duration frequency (6 Hz) stimulation. This is a study model for therapy-resistant partial seizures.

Adult male CF1 mice (weighing 18 to 25 g) were pretreated intraperitoneally with the cannabidiol at a dose of 100 mg/kg. The cannabidiol administered to the mice was substantially pure, synthetically synthesized, cannabidiol which had a purity greater than 98%. The cannabidiol was dissolved in 0.5% methylcellulose or a 1:1:18 ratio of ethanol:polyethoxylated castor oil:PBS.

Each treatment group (n=4 mice/group) was examined for anticonvulsive effects at one of five time points (¼, ½, 1, 2, and 4 hours) following treatment with cannabidiol. Following pretreatment, each mouse received a drop of 0.5% tetracaine hydrochloride applied to each eye. The mouse was then challenged with the low-frequency (6 Hz) stimulation for 3 seconds delivered through corneal electrodes. The low-frequency, long-duration stimuli was initially delivered at 32 mA intensity. Animals were manually restrained and released immediately following the stimulations and observed for seizure activity. If the test compound was effective in the 32 mA screen, an additional assay wherein the stimulation current is increased to 44 mA is employed using the same protocol as described above. Additionally, a dose response curve can be generated at the time of peak effect (TPE) at the specific stimulation intensity.

Typically, the 6 Hz stimulation results in a seizure characterized by a minimal clonic phase that is followed by stereotyped, automatistic behaviors, including twitching of the vibrissae, and Straub-tail. Animals not displaying such behaviors were considered protected. Data was analyzed by Mann-Whitney U test, with $p<0.05$ determined to be statistically significant.

For each time group, the results are expressed as the total number of animals protected out of the number of animals tested over time (i.e., 2/4 represents 2 out of 4 mice tested were protected).

TABLE 53

ED50 Biological Response, Methylcellulose

| Test | Dose | Time (Hours) 0.5 N/F |
|---|---|---|
| 6 Hz | 30 | 0/8 |
| 6 Hz | 65 | 5/8 |
| 6 Hz | 130 | 5/8 |
| 6 Hz | 160 | 8/16 |
| 6 Hz | 190 | 7/8 |

TABLE 54

Time to Peak Effect, Methylcellulose

| | | Time (Hours) | | | | | | |
|---|---|---|---|---|---|---|---|---|
| Test | Dose | 0.25 N/F | 0.5 N/F | 1 N/F | 2 N/F | 4 N/F | 6 N/F | 24 N/F |
| 6 Hz | 300 | 1/8 | 0/8 | 0/8 | 0/8 | 0/8 | 0/8 | 0/8 |
| 6 Hz | 500 | 1/8 | 0/8 | 0/8 | 0/8 | 0/8 | 0/8 | 2/8 |

TABLE 55

ED50 Biological Response, Ethanol:Polyethoxylated castor oil:PBS

| Test | Dose | Time | N/F |
|---|---|---|---|
| 6 Hz | 50 | 0.5 | 1/8 |
| 6 Hz | 100 | 0.5 | 1/8 |
| 6 Hz | 130 | 0.5 | 4/8 |
| 6 Hz | 170 | 0.5 | 6/8 |
| 6 Hz | 200 | 0.5 | 8/8 |
| TOX | 200 | 2 | 0/8 |
| TOX | 250 | 2 | 4/8 |
| TOX | 300 | 2 | 6/8 |
| TOX | 500 | 2 | 8/8 |

TABLE 56

Time to Peak Effect, Ethanol:Polyethoxylated castor oil:PBS

| | | Time (Hours) | | | | | | | |
|---|---|---|---|---|---|---|---|---|---|
| Test | Dose | 0.25 N/F | 0.5 N/F | 1 N/F | 2 N/F | 4 N/F | 6 N/F | 8 N/F | 24 N/F |
| TOX | 200 | — | — | — | 0/8 | 0/8 | — | — | — |
| TOX | 250 | — | — | — | 4/8 | 3/8 | — | — | — |
| TOX | 300 | — | — | — | 6/8 | 7/8 | 4/8 | 2/8 | 1/8 |
| TOX | 500 | 0/8 | 0/8 | 0/8 | 8/8 | 8/8 | 8/8 | — | 4/7 |

As seen in Tables 53 to 56, cannabidiol in both solvents showed comparable median effective doses that inhibited seizures in 50% of animals (ED50s) in the 100 mg/kg range. While cannabidiol dissolved in the methylcellulose solvent had an ED50 of 103.75 mg/kg (95% Confidence Interval of 53.89 mg/kg to 163.84 mg/kg), it showed an ED50 of 121.52 mg/kg when dissolved in the 1:1:18 ethanol:polyethoxylated castor oil:PBS solvent (95% Confidence Interval of 87.83 mg/kg to 152.96 mg/kg). Based on the toxicity data for the cannabidiol in the methylcellulose solvent, the median toxicity dose where toxicity is observed in 50% of animals ("TD50") was determined to exceed 500 mg/kg at 0.5 hours post administration. Diarrhea at 24 hours and 1 death was reported at 24 hours at 500 mg/kg, the highest dose tested.

The TD50 was determined to be 262.37 mg/kg (95% Confidence Interval of 232.64 to 301.78) with cannabidiol dissolved in the 1:1:18 ethanol:polyethoxylated castor oil:PBS solvent. Death was reported at 24 hours at 300 mg/kg and at 6 and 24 hours for 500 mg/kg with the with the 1:1:18 ethanol:polyethoxylated castor oil:PBS solvent.

These results further illustrate that cannabidiol is likely to be effective in humans for the treatment of epilepsy and other conditions. Further, synthetically synthesized cannabidiol will likely be less toxic than cannabidiol that is derived from plants and not substantially pure.

Example 13. Maximal Electroshock Seizure and Subcutaneous Metrazol

The maximal electroshock seizure ("MES") and subcutaneous Metrazol ("sc Met") tests have been the two most widely employed preclinical seizure models for the early identification and high through-put screening of investigational anti-seizure drugs. These tests have been extremely effective in identifying new anti-seizure drugs that may be useful for the treatment of human generalized tonic-clonic seizures and generalized myoclonic seizures. The MES test provides an indication of CBD's ability to prevent seizure spread when all neuronal circuits in the brain are maximally active. The s.c. Met test detects the ability of CBD to raise the chemoconvulsant-induced seizure threshold of an animal and, thus, protect it from exhibiting a clonic, forebrain seizure.

For the MES test, 60 Hz of alternating current is delivered by corneal electrodes for 0.2 seconds. Supra-maximal seizures are elicited with a current intensity five times that necessary to evoke a threshold tonic extension seizure, i.e., 50 mA in mice and 150 mA in rats. A drop of anesthetic solution, 0.5% tetracaine hydrochloride, is placed on the eyes of each animal just before the corneal electrodes are applied to the eyes to elicit electrical stimulation. The animals are restrained by hand and released immediately following stimulation to allow observation of the entire seizure. Inhibition of the hind leg tonic extensor component is taken as the endpoint for the MES test.

A dose of Metrazol (85 mg/kg in mice) will induce convulsions in 97% of mice (CD97). The CD97 dose of Metrazol is injected into a loose fold of skin in the midline of the neck. The CD97 doses for Metrazol are confirmed annually in mice. It is administered to mice at a volume of 0.01 ml/g body weight. The animals are then placed in isolation cages to minimize stress and continuously monitored for the next 30 min for the presence or absence of a seizure. An episode of clonic spasms, approximately 3 to 5 seconds, of the fore and/or hind limbs, jaws, or vibrissae is taken as the endpoint. Animals not displaying fore and/or hind limb clonus, jaw chomping, or vibrissae twitching are considered protected.

All quantitative in vivo antiseizure/behavioral impairment studies are typically conducted at the previously determined TPE. Groups of at least 8 mice were tested with various doses of cannabidiol until at least two points are established between the limits of 100% protection or minimal toxicity and 0% protection or minimal toxicity. The dose of drug required to produce the desired endpoint in 50% of animals (ED50 or TD50) in each test, the 95% confidence interval, the slope of the regression line, and the standard error of the mean (S.E.M.) of the slope is then calculated by probit analysis.

The cannabidiol administered to the mice was substantially pure, synthetically synthesized, cannabidiol which had a purity greater than 98%. The cannabidiol was dissolved in 0.5% methylcellulose or a 1:1:18 ratio of ethanol:polyethoxylated castor oil:PBS. The maximal electric shock (MES) and subsucanteous Metrazol ("sc MET") are the most widely used preclinical seizure models for the early identification and screening of new antiepileptic drugs.

TABLE 57

ED50 Biological Response, Methylcellulose

| Test | Dose | Time | N/F |
|---|---|---|---|
| MES | 200 | 2 | 5/8 |
| MES | 250 | 2 | 4/8 |
| MES | 300 | 2 | 4/8 |
| MES | 350 | 2 | 3/8 |
| MES | 400 | 2 | 3/8 |
| MES | 450 | 2 | 6/8 |
| MES | 500 | 2 | 8/8 |
| Sc MET | 150 | 2 | 1/8 |
| Sc MET | 200 | 2 | 3/8 |
| Sc MET | 300 | 2 | 5/8 |
| Sc MET | 360 | 2 | 7/8 |
| TOX | 500 | 2 | 0/8 |

TABLE 58

Time to Peak Effect, Methylcellulose

| | | Time (Hours) | | | | |
|---|---|---|---|---|---|---|
| Test | Dose | 0.25 N/F | 0.5 N/F | 1 N/F | 2 N/F | 4 N/F |
| MES | 300 | 0/4 | 1/4 | 1/4 | 4/8 | 2/4 |
| Sc MET | 200 | 0/4 | 0/4 | 2/8 | 3/8 | — |
| TOX | 300 | 0/4 | 0/4 | 0/4 | 0/4 | 0/4 |

TABLE 59

ED50 Biological Response, Ethanol:Polyethoxylated castor oil:PBS

| Test | Dose | Time | N/F |
|---|---|---|---|
| MES | 75 | 2 | 1/8 |
| MES | 95 | 2 | 5/8 |
| MES | 120 | 2 | 7/8 |
| MES | 150 | 2 | 8/8 |
| Sc MET | 120 | 2 | 0/8 |
| Sc MET | 160 | 2 | 2/8 |
| Sc MET | 220 | 2 | 5/8 |
| Sc MET | 260 | 2 | 7/8 |
| TOX | 175 | 2 | 0/8 |
| TOX | 250 | 2 | 4/8 |
| TOX | 325 | 2 | 6/8 |
| TOX | 500 | 2 | 8/8 |

TABLE 60

Time to Peak Effect, Ethanol:Polyethoxylated castor oil:PBS

| | | Time (Hours) | | | | | | |
|---|---|---|---|---|---|---|---|---|
| Test | Dose | 0.25 N/F | 0.5 N/F | 1 N/F | 2 N/F | 4 N/F | 6 N/F | 8 N/F |
| TOX | 500 | 0/8 | 0/8 | 0/8 | 8/8 | 7/8 | 7/8 | 4/8 |

The ED50 in the MES model for cannabidiol dissolved in the methylcellulose solvent could not be calculated due to a U shaped dose response (¼ protected at 0.5 hr, ¼ at 1 hr, ⅜ at 2 hr and ⅔ at 4 hr). However, the ED50 for cannabidiol dissolved in the 1:1:18 ethanol:polyethoxlated castor oil:PBS solvent is 92.21 mg/kg (95% Confidence Interval of 78.4 mg/kg to 104.63 mg/kg).

For the MET model, the ED50 was 241.03 mg/kg (95% Confidence Interval of 182.23 to 311.87) for cannabidiol dissolved in the methylcellulose solvent and 198.51 mg/kg (95% Confidence Interval of 167.76 mg/kg to 232.58 mg/kg) for cannabidiol dissolved in the 1:1:18 ethanol:polyethoxlated castor oil:PBS solvent. Based on the toxicity data for cannabidiol dissolved in the methylcellulose solvent the TD50 was determined to exceed 500 mg/kg, the highest dose tested.

Myoclonic jerks were reported in at 1 hour with 200 mg/kg dose and at 2 hours with 360 mg/kg dose. The TD50 was determined to be 266.76 mg/kg (95% Confidence Interval of 222.28 mg/kg to 317.42 mg/kg) with the cannabidiol dissolved in the 1:1:18 ethanol:polyethoxlated castor oil:PBS solvent.

These results further illustrate that cannabidiol is likely to be effective in humans for the treatment of epilepsy and other conditions. Further, synthetically synthesized cannabidiol will likely be less toxic than cannabidiol that is derived from plants and not substantially pure.

Example 14. Glioblastoma Multiforme Study

A study was conducted in order to determine the extent to which systemic administration of cannabidiol or cannabidiol plus delta-9-tetrahydrocannabinol (cannabidiol/delta-9-tetrahydrocannabinol 1:1) can inhibit glioblastoma multiforme progression and enhance the activity of temozolomide, a chemotherapy drug, in an orthotopic mouse model of glioblastoma multiforme utilizing U87 cells. It was previously suggested that the combination of cannabidiol plus delta-9- tetrahydrocannabinol is the most effective treatment for targeting tumors derived from U87 serum-derived glioblastoma multiforme cells.

The study was conducted as follows. Human U87 luciferase labeled cells were grown in Roswell Park Memorial Institute media with 10% fetal bovine serum and then harvested from dishes while in their exponential growth phase in culture with 0.1% trypsin/ethylenediaminetetraacetic acid and washed twice with serum-free Roswell Park Memorial Institute media. For the intracranial model, tumors were generated in female athymic nu/nu mice by the intracranial injection of $0.3 \times 10^6$ U87 cells in 4 µl of Roswell Park Memorial Institute media. Using this model, you can assess drug efficacy (in vivo imaging) as well as survival in the same group of animals. Survival studies were carried out in accordance with the National Institutes of Health's guidelines involving experimental neoplasia and our approved Institutional Animal Care and Use Committees protocol. Animals in all groups are removed from the study when they demonstrate any single sign indicative of significant tumor burden development, including hunched back, sustained decreased general activity, or a significant decrease in weight. In limited cases where tumors were able to escape the intracranial space, the mice were euthanized when the external tumors measured greater than 5 mm as assessed by callipers. Additionally, mice with tumors measuring $>500 \times 10^6$ radiance where removed from the study even if symptoms were not observed to assure spontaneous deaths related to seizures did not occur do to the existence of the large intracranial tumor.

The cannabinoids were dissolved in a mixture of 3% ethanol, 3% surfactant and 94% saline, and temozolomide was dissolved in 30% dimethyl sulfoxide and 70% saline. Cannabidiol that was synthetically synthesized and substantially pure was used in this study. The treatments were initiated 9 days after the injection of the tumor cells. Mice were imaged the morning before the first injection to determine initial tumor size and then groups were organized to have equal distribution of tumor size before the initiation of the first injection. Mice were treated once a day for five days with temozolomide. Mice were treated once a day, 5 days a week (Monday through Friday), with the cannabinoids until the completion of the study, except for the first week of the study where mice were injected over the weekend. All mice were administered the treatments via intraperitoneal injection. There were 12 mice per group, for a total of 72 mice. The treatment rates were as follows: cannabidiol (15 mg/kg); cannabidiol/delta-9-tetrahydrocannabinol (1:1, together @ 15 mg/kg); and temozolomide (2 mg/kg intraperitoneal injection.

Significant differences were determined using a one-way ANOVA. Bonferroni-Dunn post-hoc analyses were conducted when appropriate. Survival between groups was compared using a long-rank Mantel-Cox test. P values <0.05 defined statistical significance.

Figure 7:
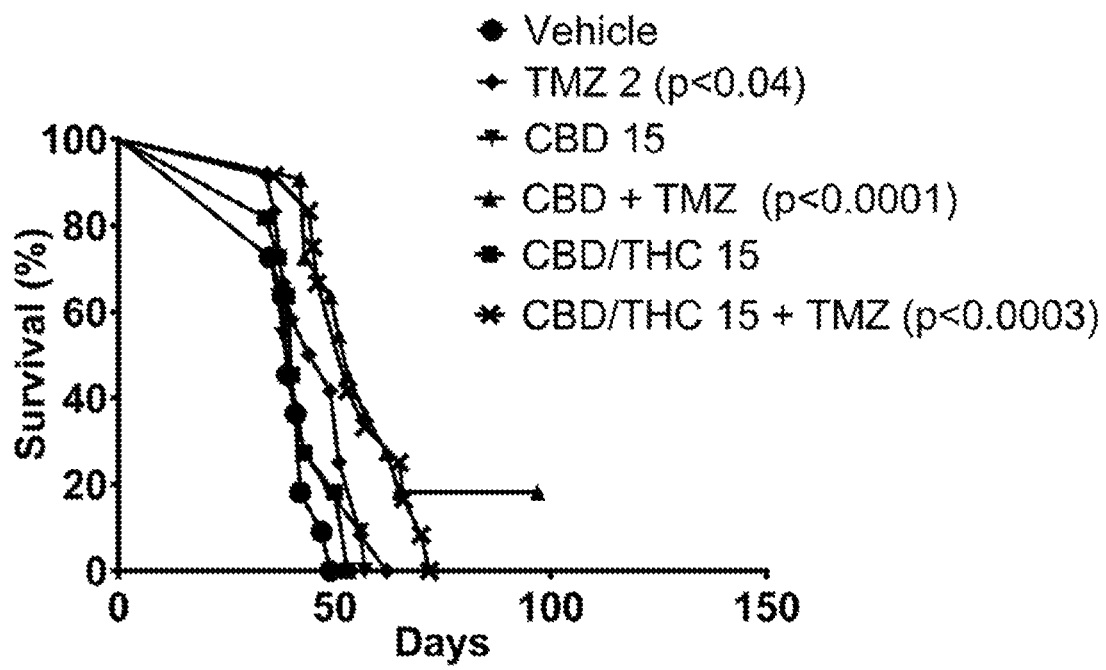
FIG. 7 shows the results from the study detailed in Example 14 and illustrates the advantages of administration of substantially pure, synthetically synthesized, cannabidiol formulations for treatment of glioblastoma multiforme.

A detailed explanation of FIG. 7 is as follows. The X-axis represents the number of days after treatment and the Y-axis represents the survival rates.

As seen in FIG. 7, while 15 mg/kg of cannabidiol alone or cannabidiol/delta-9-tetrahydrocannabinol (1:1) did not inhibit glioblastoma multiforme progression, it enhanced the antitumor activity of suboptimal doses of temozolomide leading to a significant increase in survival. Further, the substantially pure, synthetically synthesized, cannabidiol produced full regression of 20% of tumors. This effect was not observed following the 1:1 cannabidiol:delta-9-tetrahydrocannabinol treatments. It was unexpected that substantially pure, synthetically synthesized, cannabidiol would have these effects because previously it was thought that a 1:1 ratio of cannabidiol (that was extracted from cannabis and not substantially pure):delta-9-tetrahydrocannabinol would produce better effects than cannabidiol alone. However, this study again illustrates the superiority of Applicant's substantially pure, synthetically synthesized, cannabidiol.

Example 15. Additional Glioblastoma Multiforme Study

Human U251 luciferase labeled cells were grown in Roswell Park Memorial Institute media with 10% fetal bovine serum and then harvested from dishes while in their exponential growth phase in culture with 0.1% trypsin/ethylenediaminetetraacetic acid, and washed twice with serum-free Roswell Park Memorial Institute media. For the intracranial model, tumors were generated in female athymic nu/nu mice by the intracranial injection of $0.3 \times 10^6$ U251 cells in 4 µl of Roswell Park Memorial Institute media. Using this model, you can assess drug efficacy (in vivo imaging) as well as survival in the same group of animals. Survival studies were carried out in accordance with the National Institutes of Health's guidelines involving experimental neoplasia and our approved Institutional Animal Care and Use Committees protocol. Animals in all groups are removed from the study when they demonstrate any single sign indicative of significant tumor burden development, including hunched back, sustained decreased general activity, or a significant decrease in weight. In limited cases where tumors were able to escape the intracranial space, the mice were euthanized when the external tumors measured greater than 5 mm as assessed by calipers. Additionally, mice with tumors measuring $>500 \times 10^6$ radiance where removed from the study even if symptoms were not observed to assure spontaneous deaths related to seizures did not occur due to the existence of the large intracranial tumor. There were 12 mice per group, for a total of 72 mice. The treatment rates were as follows: cannabidiol (15 mg/kg); temozolomide (1.5 mg/kg intraperitoneal injection; and cannabidiol/temozolomide (10:1, together at 16.5 mg/kg.)

For drug treatment studies, cannabinoids were dissolved in a mixture of 2.5% ethanol, 2.5% Tween® 80 and 95% saline, and temozolomide was dissolved in 30% dimethyl sulfoxide and 70% saline. The treatments were initiated 9 days after the injection of the tumor cells. Mice were imaged the morning before the first injection to determine initial tumor size and then groups were organized to have equal distribution of tumor size before the initiation of the first injection. Mice were treated once a day for five days with temozolomide. Mice were treated once a day, 5 days a week (Monday through Friday), with cannabinoids until the completion of the study, except for the first week of the study where mice were inject over the weekend. All mice were injected intraperitoneally.

Significant differences were determined using a one-way ANOVA. Bonferroni-Dunn post-hoc analyses were conducted when appropriate. Survival between groups was compared using a Kaplan-Meier analysis and long-rank Mantel-Cox test or The Gehan-Breslow-Wilcoxon test. P values <0.05 defined statistical significance.

Figure 8:
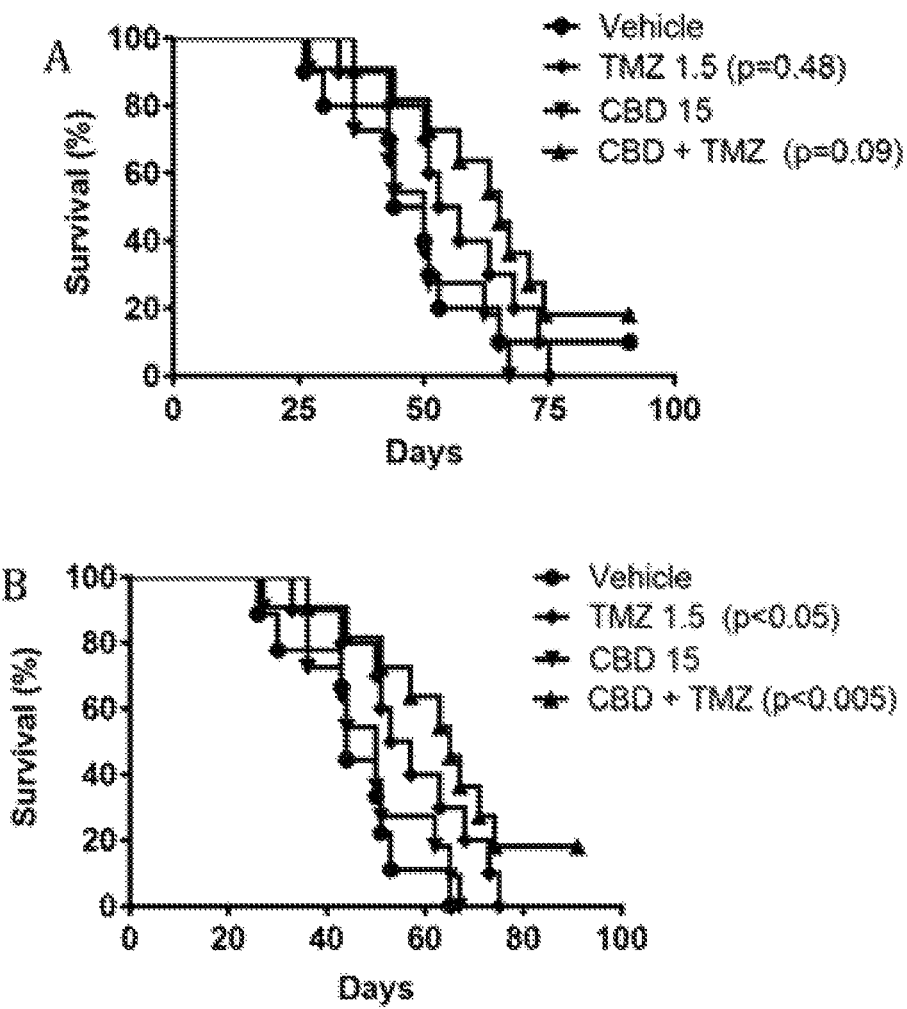
FIG. 8 shows the results from the study detailed in Example 15 and illustrates the advantages of administration of substantially pure, synthetically synthesized, cannabidiol formulations for treatment of glioblastoma multiforme.

A detailed explanation of FIG. 8 is as follows. The X-axis represents the number of days after treatment and the Y-axis represents the survival rates.

One of tumors in the vehicle group fully regressed overtime creating an outlier in the study. Tumor regression in a vehicle treated animal is a rare occurrence but it can occur. Since during the start of the study, the tumor did demonstrate a small increase in growth as assessed by IVIS imaging, it could not be removed from the data set. The data is presented with (FIG. 8A) and without (FIG. 8B) the outlier for comparison. With the vehicle outlier included, temozolomide alone did not increase survival (p=0.48, FIG. 8A, p<0.05 is considered significant). Cannabidiol alone also did not increase survival. However, the combination of temozolomide+15 mg/kg of cannabidiol almost reached significance (p=0.09) for increasing survival using a Log-rank Mantel-Cox test, p<0.05 is considered significant. If this same data set was analyzed with the Gehan-Breslow-Wilcoxon test then the treatment of temozolomide+cannabinoid did produce a significant increase in survival. The Gehan-Breslow-Wilcoxon test however is a less stringent statistical test in comparison to the Log-rank Mantel-Cox test. It should be noted that 2 of the 11 mice are still alive in the temozolomide+cannabinoid group, and in one of the mice the tumor has fully regressed based on in vivo imaging of the tumor.

If the vehicle outlier was removed from the data set, then treatment with temozolomide significantly increased survival (p<0.5, FIG. 8B). The combination of temozolomide+15 mg/kg of cannabidiol, however was highly significant at increasing survival (p=0.005). Thus, cannabidiol enhanced the antitumor activity of temozolomide.

Example 16. Pharmacokinetic Study of Multiple Dose Cannabidol Oral Solution in Pediatric Subjects with Treatment-resistant Seizure Disorders Protocol A Phase 1/2, open label, Multiple Ascending Dose study will be conducted to evaluate the effect of multiple doses of cannabidiol oral solution on pediatric subjects experiencing treatment-resistant seizures. The study will assess pharmacokinetics, safety, tolerability and preliminary efficacy of 3 doses (10, 20, and 40 milligrams per kilogram per day ("mg/kg/day") of cannabidiol oral solution administered in a sequential fashion. Specifically, twenty subjects will be enrolled in each dose cohort that A) fit the following criteria: 1. subject and/or parent(s)/caregiver(s) fully comprehend the informed consent form (ICF) and assent form, understand all study procedures, and can communicate satisfactorily with the Investigator and study coordinator; 2. provide informed consent and/or assent (as applicable) of subjects and/or parent(s)/caregiver(s) in accordance with applicable laws, regulations, and local requirements; 3. male or female between 1 and 17 years of age (inclusive) at the time of consent; 4. diagnosed with a treatment-resistant seizure disorder in the opinion of the Investigator and as defined as continued seizures despite: a. adequate trials of ≥3 antiepileptic drugs ("AEDs"), and b. ≥1 prior adequate treatment course with ≥2 AEDs in combination (i.e., concurrently); 5. willingness to remain on established AEDs (stable dosing for ≥30 days prior to Day 0 and throughout the duration of the study) a. neither a vagus nerve stimulation (VNS) procedure nor ketogenic diet are considered an AED for the purposes of this study; 6. willingness to not start a ketogenic diet during the Treatment Period or, if already on the diet, to make no changes in the diet during the study; 7. a female subject is eligible to participate in the study if she is: a. premenarchal, or b. of childbearing potential with a negative urine pregnancy test at the Screening Visit and at Day 0. If sexually active, she must agree to fulfill one of the following requirements: i. complete abstinence from intercourse ≥4 weeks prior to administration of the first dose of the investigational product, throughout the Treatment Period, and 4 weeks after completion or premature discontinuation from the investigational product, and agreement to use a double-barrier method if she becomes sexually active; ii. use of acceptable methods of contraception throughout the study and 4 weeks after completion or premature discontinuation from investigational product. The acceptable method of contraception is double barrier method (i.e., condom plus spermicide or a condom plus diaphragm); 8. a sexually active male subject must be willing to use acceptable methods of contraception throughout the study and for 4 weeks completion of study participation or premature discontinuation from investigational product. The acceptable methods of birth control are abstinence or double barrier birth control (i.e., condom plus spermicide or a condom plus diaphragm); 9. in the opinion of the Investigator, the parent(s)/caregiver(s) are willing and able to comply with the study procedures and visit schedules, including venipuncture, inpatient stay at the study center, dosing at the study center (twice a day as needed while an outpatient), and the Follow-up Visits (if applicable); 10. general good health (defined as the absence of any clinically relevant abnormalities as determined by the Investigator) based on physical and neurological examinations, medical history, and clinical laboratory values (hematology, chemistry, and urinalysis) completed during the Screening Visit; and 11. body weight of ≥9 kg; and B) do not meet the following criteria: 1. subject or parent(s)/caregiver(s) have daily commitments during the study duration that would interfere with attending all study visits; 2. currently taking concomitant medications that are strong cytochrome P450 3A4 ("CYP3A4") inhibitors or inducers or CYP3A4 sensitive substrates with a narrow therapeutic index; 3. currently taking any other disallowed medications; 4. currently taking felbamate if they had been receiving it for <6 months prior to the Screening Visit; 5. in the opinion of the Investigator, any clinically significant, unstable medical abnormality, chronic disease, or a history of a clinically significant abnormality of the cardiovascular, gastrointestinal, respiratory, hepatic, or renal systems; 6. any disorder or history of a condition (e.g., malabsorption or gastrointestinal surgery) that may interfere with drug absorption, distribution, metabolism, or excretion; 7. history or presence of abnormal electrocardiograms ("ECGs") that are clinically significant in the opinion of the Investigator; 8. for appropriate subjects, an affirmative answer to queries regarding active suicidal ideation with some intent to act but without a specific plan or active suicidal ideation with specific plan and intent on the Columbia Suicide Severity Rating Scale ("C-SSRS") assessment at the Screening Visit, subjects who have significant findings for suicidal ideation as assessed by the C-SSRS must be referred to the Investigator for follow-up evaluation; 9. any history of attempted suicide; 10. history of poor toleration of venipuncture or poor venous access that would cause difficulty in collecting blood samples; 11. participation in any investigational study currently or within 30 days or 5 half-lives (t½) of the investigational product (whichever is longer) prior to the Screening Visit; 12. taken any cannabinoids (cannabidiol, Δ9-tetrahydrocannabinol [Δ9-THC], hemp oil, Realm Oil or marijuana) in the 30 days prior to the Screening Visit; 13. history of an allergic reaction or a known or suspected sensitivity to any substance that is contained in the investigational product formulation; 14. known infection with hepatitis B, hepatitis C, or human immunodeficiency virus (HIV); 15. In the opinion of the Investigator, the subject is unsuitable in any other way to participate in this study; and 16. body weight of >90 kg.

Each subject will be enrolled in only one dose cohort. No fewer than 2 subjects between 2 and 12 years of age must be dosed through Day 10 prior to dosing any subject <2 years of age. Each of the 3 planned dose cohorts will include 20 subjects for a study total of 60 subjects: 1 to <2 years of age: 5 subjects; 2 to <12 years of age: 9 subjects with at least 3 under the age of 6; and 12 to ≤17 years of age: 6 subjects with at least 3 subjects under age 16. Each subject will complete a Screening Period of up to 28 days and a Treatment Period of 10 days. Subjects will have a Follow-up Visit on Day 14 and a Follow-up Phone Call on Day 17. On Day 1, the investigational product will be administered once in the morning according to the subject's assigned dose level cohort. The evening dose of the investigational product will not be administered on Day 1. Thus, the subject will receive a half-daily dose only (5, 10, or 20 millgrams/kilogram "mg/kg" total) of the investigational product on Day 1. Subjects will not receive a dose from Day 2 through Day 3 but they will remain in an inpatient setting and complete planned assessments. Subjects will be dosed twice daily (i.e., full daily dose of 10, 20, or 40 mg/kg/day) from Day 4 through Day 10 according to the subject's assigned cohort. Doses will be administered at approximately 12-hour intervals. Doses will be administered to subjects in a fasting state on days on which the serial PK samples will be collected (i.e., Day 1 and Day 10.) Fasting times include 1 hour for ages 1 to less than 2 years and 2 hours for ages 2 to 17 years.

During the Screening, Treatment, and Follow-up Periods, subjects are not to receive the following: (1) medication(s) that are strong CYP3A4 inhibitors or inducers or CYP3A4-sensitive substrates with a narrow therapeutic index; (2) any cannabinoids (cannabidiol, Δ9-THC, hemp oil, Realm Oil or marijuana); corticotrophins; systemic steroid therapy (excluding inhaled medication for asthma treatment); felbamate (if used for <6 months) or (7) any other investigational drug or investigational device. Subjects will remain on established antiepilepsy therapies (i.e., AEDs for which dosing has been stable ≥30 days prior to Day 0) throughout the duration of the Treatment and Follow-up Periods.

In summary, for subjects ages 1 to <2 years, serial blood sampling for pharmacokinetic ("PK") analysis will occur at 2, 4, 8, and 12 hours post the Day 1 dose. Serial blood sampling for PK analysis will also occur at predose, 2, 4, 8, and 12 hours post the Day 10 morning dose. For subjects ages 2 to <6 years, serial blood sampling will occur at predose and at 1, 2, 3, 4, 8, 12, 16, 24 (Day 2), and 48 (Day 3) hours post the Day 1 morning dose. Blood samples for PK trough values for cannabidiol and its 7-hydroxy ("OH") metabolite will be evaluated on Day 8. Collection will occur prior to the morning dose of the investigational product; no investigational product will be administered on Day 11. Serial blood sampling for PK analysis will also occur at predose, 1, 2, 3, 4, 8, 12, and 24 (Day 11) hours post the Day 10 morning dose. For subjects ages 6 to ≤17 years, serial blood sampling for PK analysis will occur predose and at 1, 2, 3, 4, 6, 8, 12, 16, 24 (Day 2), 36 (Day 2), 48 (Day 3), and 72 (Day 4) hours post the Day 1 morning dose. Blood samples for PK trough values for cannabidiol and its 7-OH metabolite will be evaluated on Day 6 (age ≥12 only), Day 8 and Day 9. Collection will occur prior to the morning dose of the investigational product; no investigational product will be administered on Day 11. Serial blood sampling for PK analysis will also occur at predose and at 1, 2, 3, 4, 6, 8, 12, and 24 (Day 11) hours post the Day 10 morning dose. In addition to the above measurements of cannabidiol and its 7-OH metabolite, levels of clobazam and norclobazam will be measured from the samples taken predose on Day 1 (baseline), Day 8, and Day 10 (predose) for subjects who are aged ≥2 years and are currently taking clobazam.

Endpoints

Endpoints of the study will include the following: (1) Incidence, type, and severity of adverse events ("AEs") and serious adverse events ("SAEs") occurring during the Treatment Period (i.e., treatment-emergent adverse events ["TEAEs"]); (2) Changes from baseline in vital signs; (3) Changes from baseline in ECG findings; (4) Changes from baseline in laboratory values (hematology, chemistry, and urinalysis); (5) Plasma PK variables for cannabidiol (parent compound) and its 7-OH metabolite as appropriate: (a) Maximum plasma concentration ($C_{max}$) and dose normalized Cmax ($C_{max}/D$) (b) time to $C_{max}$ ($t_{max}$); (c) Half-life ($t_{1/2}$); (d) Elimination rate; (e) Oral clearance (cannabidiol only); (f) Volume of distribution (cannabidiol only); (g) Area under the plasma concentration-time curve from 0 to 12 hours [$AUC_{(0-12)}$] and dose normalized $AUC_{(0-12)}$ [$AUC_{(0-12)}/D$] on Day 1; (h) Area under curve from time 0 to the last quantifiable concentration [$AUC_{(0-last)}$] on Day 1: (i) Area under the plasma concentration-time curve from 0 to infinity ($AUC_{[0-inf]}$) and dose normalized $AUC_{(0-inf)}$ [$AUC_{(0-inf)}/D$] on Day 1 for study subjects ≥2 years of age; (j) Metabolite to parent ratios for $C_{max}$, $AUC_{(0-inf)}$, $AUC_{(0-12)}$ on Day 1 and Day 10; (k) $AUC_{(0-12)}$ and $AUC_{(0-12)}/D$ on Day 10; (1) Minimum plasma concentration ($C_{min}$) on Day 10; (m) Average plasma concentration ($C_{avg}$) on Day 10; (n) Accumulation ratios for $C_{max}$ and $AUC_{(0-12)}$ on Day 10; (o) Time linearity; (6) clinical global impressions of improvement ("CGI-I") assessment on Day 11; and (7) Change from baseline in clinical global impressions of severity ("CGI-S") assessment from the Screening Visit to Day 11.

Safety

Subjects will be assessed by measurement of vital signs and neurological examination daily. A Physical Examination will be completed at the Screening Visit, as well as Day 0, Day 11 and Day 14. A 12-lead ECG, will be completed at the Screening Visit, as well as Day 1, Day 4, Day 8, Day 11, and Day 14 (if clinically indicated). Hematology, chemistry, and urine analysis will be performed at the Screening Visit, as well as Day 1, Day 4, Day 8, and Day 11. Hematology, chemistry, and urine analysis will also be performed on Day 14 if clinically indicated.

Methods

The PK concentrations and parameters for cannabidiol and its 7-OH metabolite in plasma will be summarized by study day, sampling time (where appropriate) and dose using descriptive statistics and graphic displays as appropriate. These results will be graphically displayed by age and mg/kg dose, as appropriate. Exposure relationship with age and body weight will be evaluated using regression and/or inferential analyses, as appropriate. Dose proportionality of cannabidiol and its 7-OH metabolite exposure will be investigated using graphical methods and statistically using a power model approach, as appropriate. Accumulation of cannabidiol and its 7-OH metabolite will be assessed using an appropriate analysis of variance model for exposure PK parameters. Time linearity will also be assessed. Trough concentrations samples collected prior to dosing at the scheduled time points will be assessed graphically for attainment of steady state. Also, time to reach steady state will be assessed with a stepwise linear trend analysis. Levels of clobazam and norclobazam will be measured from the samples taken predose on Day 1 (baseline), Day 8, and Day 10 (predose) for subjects who are age ≥2 and currently taking clobazam and summarized by time point and treatment. All safety assessments, including AEs, clinical laboratory evaluations, vital signs, 12-lead ECGs, C-SSRS, and physical and neurological examinations will be listed. When appropriate, they will be summarized with descriptive statistics by age and dose cohort. The results of the CGI-I, CGI-S, and daily seizure diary assessments will be summarized by descriptive statistics as appropriate.

Results

Preliminary results are shown in Table 61 below. Cohort #1 was administered a single dose of 5 mg/kg of an alcohol based formulation and then 5 mg/kg BID (10 mg/kg/day) for 7 days. Cohort #2 was administered a single dose of 10 mg/kg of a lipid based formulation and then 10 mg/kg BID (20 mg/kg/day) for 7 days. For cohort #1 single dosing resulted in a mean $C_{max}$ of 59.029 ng/mL, mean $T_{max}$ of 3.0 hours and an $AUC_{inf}$ of 276.95 h*ng/mL. For cohort #2 single dosing resulted in a mean $C_{max}$ of 110.522 ng/mL, mean $T_{max}$ of 4.45 hours and an $AUC_{inf}$ of 879.273 h*ng/mL. As demonstrated, lipid based formulations at twice the dosage and at a single dosing achieved nearly twice the maximum plasma concentration of the alcohol based formulations in nearly an hour and half longer.

At repeated BID dosing, administration of alcohol based oral cannabinoid formulations resulted in a mean $C_{max}$ of 119.6 ng/mL, mean $T_{max}$ of 2.75 hours and an $AUC_{tau}$ of 581.744 h*ng/mL and the lipid based or al cannabinoid formulations resulted in a $C_{max}$ of 214.28 ng/mL, mean $T_{max}$ of 2.55 hours and an $AUC_{tau}$ of 1135.345 h*ng/mL. As demonstrated, lipid based formulations at twice the dosage and at administered BID for 7 days achieved less than twice the maximum plasma concentration of the alcohol based formulations twelve minutes faster.

wash-out period. For pharmacokinetic analysis, nominal time and default lambda-z selections were used. All below quantifiable limit values were set to zero and all subjects were included in the analysis.

Safety

Safety was assessed using the following parameters: inclusion/exclusion criteria, medical history and demographics, medical history update, continuing eligibility, physical examination, clinical laboratory testing, 12-lead electrocardiogram (ECG), urine drug and alcohol screens, prior medication history, concomitant medication, seated blood pressure, pulse, respiration rate, and oral temperature, and adverse event (AE) assessments.

Statistical Methods

Data from 13 subjects from the fasted treatment and 24 subject from the fed treatment were included in the pharmacokinetic and statistical analyses.

Blood samples (1×6 mL) for cannabidiol and 7-OH-cannabidiol analysis were collected in Vacutainer tubes containing $K_2$-EDTA as a preservative at 0 hour (predose), 0.25, 0.5, 0.75, 1.0, 1.5, 2.0, 2.5, 3.0, 4.0, 6.0, 8.0, 12, 16, 24, 36, 48, 72, 96, and 120 hours postdose (20 time points) in each study period. The following pharmacokinetic parameters were calculated: peak concentration in plasma ($C_{max}$), time to peak concentration ($T_{max}$), last quantifiable concentration determined directly from individual concentration-time data ($C_{last}$), time of last quantifiable concentration ($T_{last}$), elimination rate constant ($\lambda_z$), terminal half-life ($T_{1/2}$), area under the concentration-time curve from time-zero to the time of the last quantifiable concentration ($AUC_{0-t}$), area under the plasma concentration time curve from time-zero extrapolated to infinity ($AUC_{inf}$), percentage of $AUC_{inf}$ obtained by extrapolation ($AUC_{extrap}$), calculated as

TABLE 61

Pharmacokinetic Parameters for Oral Cannabinoid Solutions

| Group | | Single Dosing | | | Twice-a-day Dosing for 7 days | | |
|---|---|---|---|---|---|---|---|
| | | $T_{max}$ (h) | $C_{max}$ (ng/mL) | $AUC_{inf}$ (h * ng/mL) | $T_{max}$ (h) | $C_{max}$ (ng/mL) | $AUC_{tau}$ (h * ng/mL) |
| Cohort #1 | N | 20 | 20 | 15 | N  20 | 20 | 19 |
| | Mean | 3 | 59.029 | 276.95 | Mean  2.75 | 119.6 | 581.774 |
| | SD | 1.62 | 99.98 | 237.749 | SD  0.97 | 105.035 | 282.096 |
| | Min | 1 | 7.03 | 84.84 | Min  1 | 11.1 | 95.71 |
| | Median | 2.5 | 21.1 | 152.1 | Median  3 | 94.35 | 528.35 |
| | Max | 8 | 439 | 839.69 | Max  4 | 508 | 1107.44 |
| | CV % | 54.1 | 169.4 | 85.8 | CV %  35.1 | 87.8 | 48.5 |
| Cohort #2 | N | 20 | 20 | 12 | N  20 | 20 | 18 |
| | Mean | 4.45 | 110.522 | 879.273 | Mean  2.55 | 214.28 | 1135.345 |
| | SD | 2.26 | 142.314 | 955.01 | SD  2.09 | 279.018 | 959.48 |
| | Min | 1 | 6.46 | 139.55 | Min  0 | 16.6 | 281.96 |
| | Median | 4 | 52.85 | 587.86 | Median  2 | 107 | 819.21 |
| | Max | 8 | 462 | 2919.34 | Max  8 | 1090 | 4105.46 |
| | CV % | 50.8 | 128.8 | 108.6 | CV %  81.9 | 130.2 | 84.5 |

Example 17. Pharmacokinetic Food-Effect Study of Single Dose Cannabidol Oral Solution in Healthy Subjects An open label, randomized, single-dose, two-period, two-way crossover food-effect study was conducted on healthy subjects. The study assessed pharmacokinetics and safety of single-dose of 20 mg/kg/day cannabidiol (i.e. formulation #LF10 from Table 25, above) administered under fasted or fed conditions. Twenty-four (24) subjects were enrolled in the study and each were subjected to the fasted and fed treatment arms in separate periods followed by a 7-day $AUC_{extrap}=[(AUC_{inf}-AUC_{0-t})/AUC_{inf}]*100$, apparent oral clearance (CL/F), calculated as: CL/F=Dose/$AUC_{inf}$ for dronabinol only, and volume of distribution in the terminal elimination phase (Vd/F), calculated as Vd/F=(CL/F)/$\lambda Z$ for cannabidiol only.

Results and Conclusions

Results of the pharmacokinetic and statistical analyses for the oral cannabinoid solutions of the present invention are shown in Tables 62-67. Tables 62-64 shows the pharmacokinetic parameters of cannabidiol comparing administration to subjects in a fasted or fed condition.

TABLE 62

Summary of PK parameters for cannabidiol with replicates combined after oral administration of single 20 mg/kg dose of cannabidiol solution under fasted or fed conditions to healthy volunteers.

| Parameter | Fasted | | | | Fed | | | |
|---|---|---|---|---|---|---|---|---|
| | n | Mean | SD | CV % | n | Mean | SD | CV % |
| $T_{max}$ (h) | 13 | 12.00 | (2.50, 36.00) | | 24 | 6.00 | (3.00, 12.00) | |
| $C_{max}$ (ng/mL) | 13 | 27.3 | 37.7 | 138.1 | 24 | 1560 | 865 | 55.3 |
| $AUC_{0-t}$ (h * ng/mL) | 13 | 466.2 | 354.8 | 76.1 | 24 | 9650 | 3435 | 35.6 |
| $AUC_{0-inf}$ (h * ng/mL) | 11 | 360.0 | 187.3 | 52.0 | 21 | 10090 | 3725 | 36.9 |
| $AUC_{extrap}$ (%) | 11 | 3.57 | 1.16 | 32.5 | 21 | 3.84 | 1.26 | 33.0 |
| $\lambda_z$ (h$^{-1}$) | 11 | 0.0257 | 0.0050 | 19.7 | 21 | 0.0165 | 0.0017 | 10.1 |
| $t_{1/2}$ (h) | 11 | 27.89 | 5.18 | 18.6 | 21 | 42.30 | 4.08 | 9.6 |
| $T_{last}$ (h) | 13 | 120.01 | 0.04 | 0.0 | 24 | 120.00 | 0.02 | 0.0 |
| $C_{last}$ (ng/mL) | 13 | 0.867 | 1.34 | 154.1 | 24 | 6.36 | 2.24 | 35.2 |
| CL/F (L/h/kg) | 11 | 68.39 | 29.42 | 43.0 | 21 | 2.173 | 0.6205 | 28.6 |
| Vd/F (L/kg) | 11 | 2680 | 1156 | 43.1 | 21 | 132.7 | 41.40 | 31.2 |

*Arithmetic mean ± standard deviation,
(n) denotes the number of subjects measured.
$T_{max}$ presented as median (min, max).

TABLE 63

Statistical analysis of the log-transformed systemic exposure parameters of cannabidiol comparing 20 mg/kg dose of cannabidiol under fed conditions to the same dose under fasted conditions after oral administration to healthy volunteers.

| Dependent | n | | Geometric Mean[a] | | Ratio (%)[b] | 90% CI[c] | | Power ANOVA |
|---|---|---|---|---|---|---|---|---|
| Variable | Fed | Fasted | Fed | Fasted | (Fed/Fasted) | Lower | Upper | CV % |
| $\ln(C_{max})$ | 24 | 13 | 1393.0405 | 44.4612 | 3133.16 | 1874.38 | 5237.32 | 0.1786 51.41 |
| $\ln(AUC_{0-t})$ | 24 | 13 | 9210.7934 | 668.6687 | 1377.48 | 962.32 | 1971.75 | 0.2628 32.78 |
| $\ln(AUC_{0-inf})$[d] | 21 | 11 | 9584.9742 | 326.2316 | 2938.09 | 2122.35 | 4067.37 | 0.2930 39.63 |

[a]Geometric mean for Fed and Fasted based on least squares mean of log-transformed parameter values
[b]Ratio (%) = geometric mean (fed)/geometric mean (fasted)
[c]90% confidence interval
[d]due to the limited number of subjects with data for cannabidiol oral solution, under fasted conditions during period 2, period was removed from the model in order to analyze $AUC_{0-inf}$ Substantial increases in cannabidiol maximum and total exposure, based on $\ln(C_{max})$, $\ln(AUC_{0-t})$, and $\ln(AUC_{0-inf})$, were observed after administration of 20 mg/kg cannabidiol oral solution with food compared to 20 mg/kg cannabidiol oral solution administered under fasted conditions. Cannabidiol C. was approximately 31-fold higher after administration with food compared to administration under fasted conditions. Cannabidiol $AUC_{0-t}$ and $AUC_{0-inf}$ were approximately 14-fold and 29-fold higher, respectively, after administration with food compared to administration under fasted conditions. Median time to reach maximum concentration of cannabidiol ($T_{max}$) occurred approximately 6 hours earlier with food (6 hours) compared to that under fasted conditions (12 hours). Inter-subject variability was substantially reduced with food: 55.3% CV from 138.1% for $C_{max}$ and 36.9% CV from 52.0% for $AUC_{0-inf}$.

TABLE 64

Summary of AUC for cannabidiol with replicates combined after oral administration of single 20 mg/kg dose of cannabidiol solution under fasted or fed conditions to healthy volunteers.

| Parameter* | Fasted | Fed |
|---|---|---|
| $AUC_0$ (h*ng/mL) | 0.325 ± 1.17 | 0.229 ± 0.636 |
| $AUC_{0-0.25}$ (h*ng/mL) | 0.363 ± 1.31 | 0.498 ± 0.874 |
| $AUC_{0-0.5}$ (h*ng/mL) | 0.584 ± 1.33 | 2.45 ± 3.38 |
| $AUC_{0-0.75}$ (h*ng/mL) | 1.25 ± 1.34 | 7.48 ± 11.2 |
| $AUC_{0-1}$ (h*ng/mL) | 1.93 ± 1.62 | 21.8 ± 40.0 |
| $AUC_{0-1.5}$ (h*ng/mL) | 2.79 ± 2.14 | 128 ± 215 |

TABLE 64-continued

Summary of AUC for cannabidiol with replicates combined after oral administration of single 20 mg/kg dose of cannabidiol solution under fasted or fed conditions to healthy volunteers.

| Parameter* | Fasted | Fed |
|---|---|---|
| $AUC_{0-2}$ (h*ng/mL) | 4.14 ± 2.75 | 269 ± 381 |
| $AUC_{0-2.5}$ (h*ng/mL) | 5.38 ± 4.09 | 424 ± 547 |
| $AUC_{0-3}$ (h*ng/mL) | 5.88 ± 3.99 | 535 ± 675 |
| $AUC_{0-4}$ (h*ng/mL) | 6.62 ± 3.85 | 812 ± 874 |
| $AUC_{0-6}$ (h*ng/mL) | 12.0 ± 9.29 | 1090 ± 886 |
| $AUC_{0-8}$ (h*ng/mL) | 22.9 ± 39.3 | 819 ± 590 |
| $AUC_{0-12}$ (h*ng/mL) | 14.7 ± 10.2 | 372 ± 338 |
| $AUC_{0-16}$ (h*ng/mL) | 9.76 ± 4.79 | 112 ± 133 |
| $AUC_{0-24}$ (h*ng/mL) | 5.45 ± 2.76 | 34.3 ± 11.7 |
| $AUC_{0-36}$ (h*ng/mL) | 5.00 ± 3.78 | 20.7 ± 5.11 |
| $AUC_{0-48}$ (h*ng/mL) | 2.66 ± 2.40 | 15.5 ± 4.31 |
| $AUC_{0-72}$ (h*ng/mL) | 1.73 ± 1.89 | 10.1 ± 3.42 |
| $AUC_{0-96}$ (h*ng/mL) | 1.35 ± 1.73 | 7.86 ± 2.44 |
| $AUC_{0-120}$ (h*ng/mL) | 0.867 ± 1.34 | 6.36 ± 2.24 |

*Arithmetic mean ± standard deviation. Number of subjects tested ("n") under fasted conditions was 13, n for fed is 24.

Figure 9:
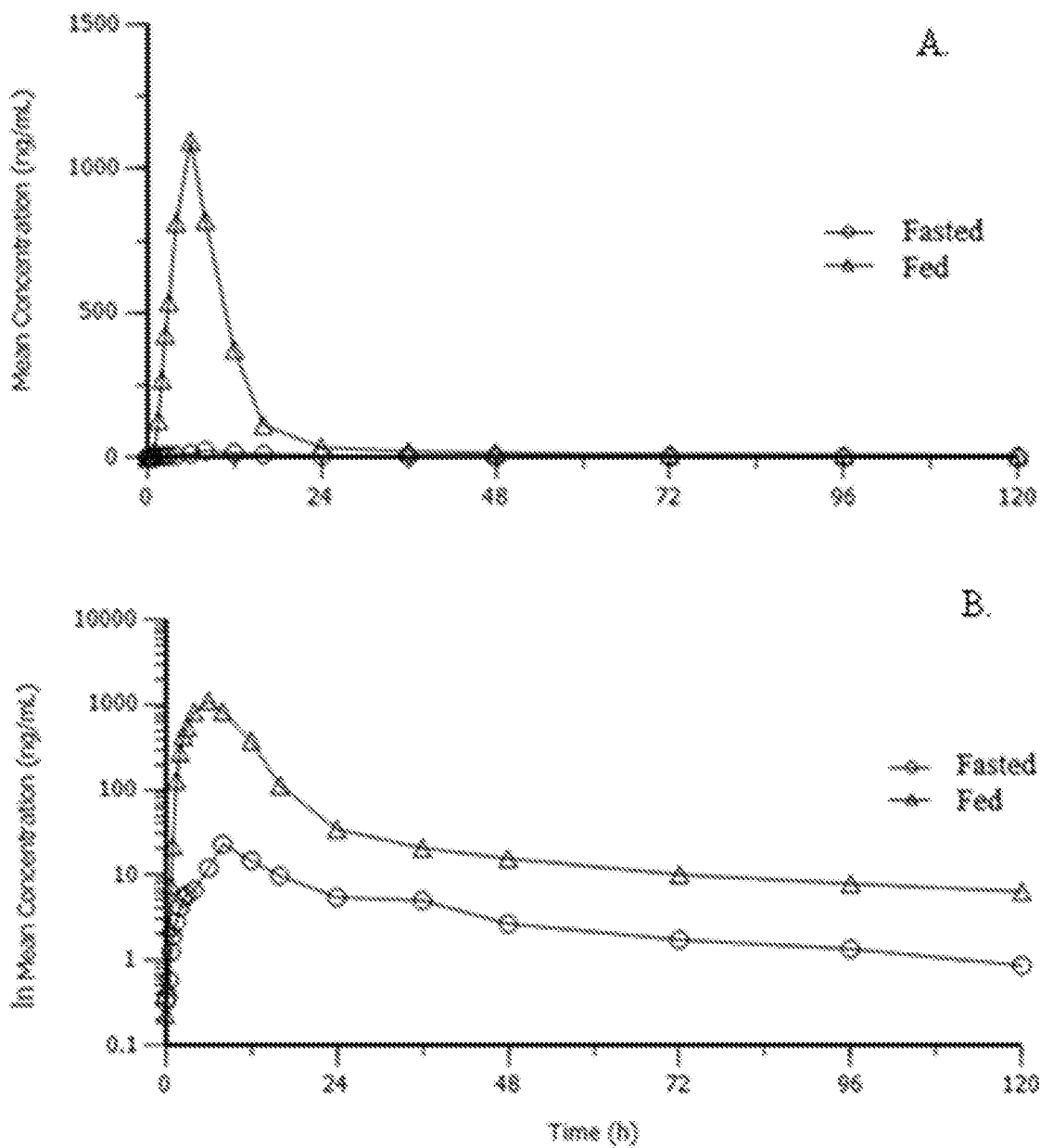
FIG. 9 shows the results from the study detailed in Example 17 and illustrates the advantages of administration of oral cannabidiol solutions to subjects in the fed condition. Panel A. shows mean cannabidiol concentrations versus time. Panel B. shows the natural log of the mean cannabidiol concentrations versus time.

Administration of oral cannabinoid solutions of the present invention under fed conditions resulted in an appreciable AUC difference in cannabidol over administration under fasted conditions within 30 minutes. See FIG. 9. Additionally, administration of oral cannabinoid solutions of the present invention under fed conditions resulted in 90 times greater AUC of cannabidol over administration under fasted conditions at 6 hours.

Tables 65-67 shows the pharmacokinetic parameters of 7-OH-cannabidiol, the primary and active metabolite of cannabidiol, comparing oral cannabinoid solutions of the present invention under fasted and fed conditions.

TABLE 65

Summary of PK parameters for 7-OH-cannabidiol with replicates combined after oral administration of single 20 mg/kg dose of cannabidiol solution under fasted or fed conditions to healthy volunteers.

| Parameter | Fasted | | | | Fed | | | |
| --- | --- | --- | --- | --- | --- | --- | --- | --- |
| | n | Mean | SD | CV % | n | Mean | SD | CV % |
| $T_{max}$ (h) | 13 | 8.00 (2.50, 24.00) | | | 24 | 6.00 (3.00, 12.00) | | |
| $C_{max}$ (ng/mL) | 13 | 22.8 | 33.4 | 146.4 | 24 | 474 | 187 | 39.4 |
| $AUC_{0-t}$ (h * ng/mL) | 13 | 414.7 | 291.0 | 70.2 | 24 | 4811 | 1509 | 31.4 |
| $AUC_{0-inf}$ (h * ng/mL) | 12 | 425.3 | 331.4 | 77.9 | 24 | 4902 | 1520 | 31.0 |
| $AUC_{extrap}$ (%) | 12 | 2.77 | 2.10 | 75.8 | 24 | 1.93 | 1.33 | 68.7 |
| $\lambda_z$ (h$^{-1}$) | 12 | 0.0348 | 0.0090 | 25.8 | 24 | 0.0292 | 0.0056 | 19.3 |
| $t_{1/2}$ (h) | 12 | 21.36 | 6.26 | 29.3 | 24 | 24.69 | 5.36 | 21.7 |
| $T_{last}$ (h) | 13 | 114.47 | 10.53 | 9.2 | 24 | 120.00 | 0.02 | 0.0 |
| $C_{last}$ (ng/mL) | 13 | 0.561 | 0.770 | 137.2 | 24 | 2.41 | 1.26 | 52.3 |

*Arithmetic mean ± standard deviation, (n) denotes the number of subjects measured.
$T_{max}$ presented as median (min, max).

TABLE 66

Statistical analysis of the log-transformed systemic exposure parameters of 7-OH-cannabidiol comparing 20 mg/kg dose of cannabidiol under fed conditions to the same dose under fasted conditions after oral administration to healthy volunteers.

| Dependent Variable | n | | Geometric Mean[a] | | Ratio (%)[b] | 90% CI[c] | | Power ANOVA | |
| --- | --- | --- | --- | --- | --- | --- | --- | --- | --- |
| | Fed | Fasted | Fed | Fasted | (Fed/Fasted) | Lower | Upper | | CV % |
| $\ln(C_{max})$ | 24 | 13 | 442.6751 | 34.8933 | 1268.65 | 792.62 | 2030.58 | 0.1941 | 43.92 |
| $\ln(AUC_{0-t})$ | 24 | 13 | 4610.3024 | 630.3322 | 731.41 | 532.52 | 1004.57 | 0.3077 | 31.14 |
| $\ln(AUC_{0-inf})$ | 24 | 12 | 4701.4345 | 657.5873 | 714.95 | 520.18 | 982.65 | 0.3060 | 31.28 |

[a]Geometric mean for Fed and Fasted based on least squares mean of log-transformed parameter values
[b]Ratio (%) = geometric mean (fed)/geometric mean (fasted)
[c]90% confidence interval Substantial increases in 7-OH-cannabidiol maximum and total exposure, based on $\ln(C_{max})$, $\ln(AUC_{0-t})$, and $\ln(AUC_{0-inf})$, were observed after administration of 20 mg/kg cannabidiol oral solution with food compared to 20 mg/kg cannabidiol oral solution administered under fasted conditions. 7-OH-cannabidiol $C_{max}$ was approximately 13-fold higher after administration with food compared to administration under fasted conditions. 7-OH-cannabidiol $AUC_{0-t}$ and $AUC_{0-inf}$ were both approximately 7-fold higher after administration with food compared to administration under fasted conditions. Additionally, $T_{max}$ occurs 2 hours sooner under fed conditions.

TABLE 67

Summary of AUC for 7-OH-cannabidiol with replicates combined after oral administration of single 20 mg/kg dose of cannabidiol solution under fasted or fed conditions to healthy volunteers.

| Parameter* | Fasted | Fed |
| --- | --- | --- |
| $AUC_0$ (h*ng/mL) | 0.114 ± 0.410 | 0.131 ± 0.537 |
| $AUC_{0-0.25}$ (h*ng/mL) | 0.101 ± 0.363 | 0.221 ± 0.676 |
| $AUC_{0-0.5}$ (h*ng/mL) | 0.217 ± 0.361 | 0.980 ± 1.29 |
| $AUC_{0-0.75}$ (h*ng/mL) | 0.954 ± 0.843 | 2.87 ± 4.21 |
| $AUC_{0-1}$ (h*ng/mL) | 2.29 ± 2.13 | 7.33 ± 11.7 |
| $AUC_{0-1.5}$ (h*ng/mL) | 3.91 ± 3.90 | 47.5 ± 78.5 |
| $AUC_{0-2}$ (h*ng/mL) | 5.46 ± 5.23 | 104 ± 150 |

TABLE 67-continued

Summary of AUC for 7-OH-cannabidiol with replicates combined after oral administration of single 20 mg/kg dose of cannabidiol solution under fasted or fed conditions to healthy volunteers.

| Parameter* | Fasted | Fed |
| --- | --- | --- |
| $AUC_{0-2.5}$ (h*ng/mL) | 6.81 ± 6.85 | 158 ± 202 |
| $AUC_{0-3}$ (h*ng/mL) | 7.83 ± 8.27 | 197 ± 235 |
| $AUC_{0-4}$ (h*ng/mL) | 8.65 ± 8.64 | 289 ± 290 |
| $AUC_{0-6}$ (h*ng/mL) | 9.79 ± 7.71 | 346 ± 188 |
| $AUC_{0-8}$ (h*ng/mL) | 18.5 ± 34.2 | 284 ± 128 |
| $AUC_{0-12}$ (h*ng/mL) | 10.1 ± 8.36 | 187 ± 121 |
| $AUC_{0-16}$ (h*ng/mL) | 7.23 ± 4.28 | 85.7 ± 36.9 |
| $AUC_{0-24}$ (h*ng/mL) | 6.09 ± 2.70 | 47.5 ± 23.0 |
| $AUC_{0-36}$ (h*ng/mL) | 4.39 ± 2.45 | 26.7 ± 13.1 |
| $AUC_{0-48}$ (h*ng/mL) | 3.00 ± 1.91 | 16.9 ± 7.73 |
| $AUC_{0-72}$ (h*ng/mL) | 1.65 ± 1.38 | 7.36 ± 3.10 |
| $AUC_{0-96}$ (h*ng/mL) | 1.04 ± 1.11 | 4.03 ± 1.94 |
| $AUC_{0-120}$ (h*ng/mL) | 0.511 ± 0.799 | 2.41 ± 1.26 |

*Arithmetic mean ± standard deviation. Number of subjects tested ("n") under fasted conditions was 13, n for fed is 24.

Figure 10:
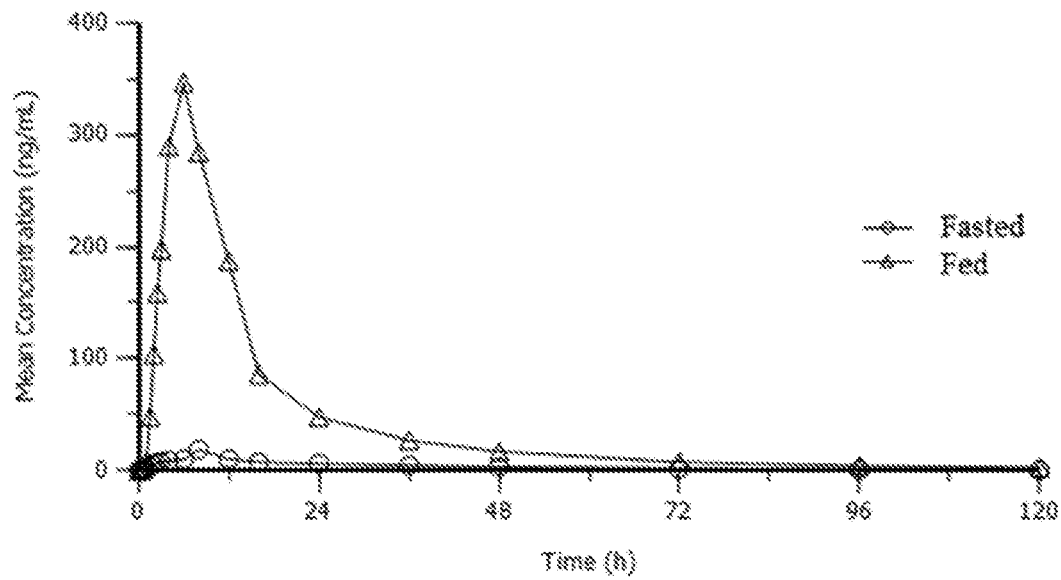
FIG. 10 shows the results from the study detailed in Example 17 and illustrates the advantages of administration of oral cannabidiol solutions to subjects in the fed condition. Panel A. shows mean 7-OH-cannabidiol concentrations versus time. Panel B. shows the natural log of the mean 7-OH-cannabidiol concentrations versus time.
Figure 10:
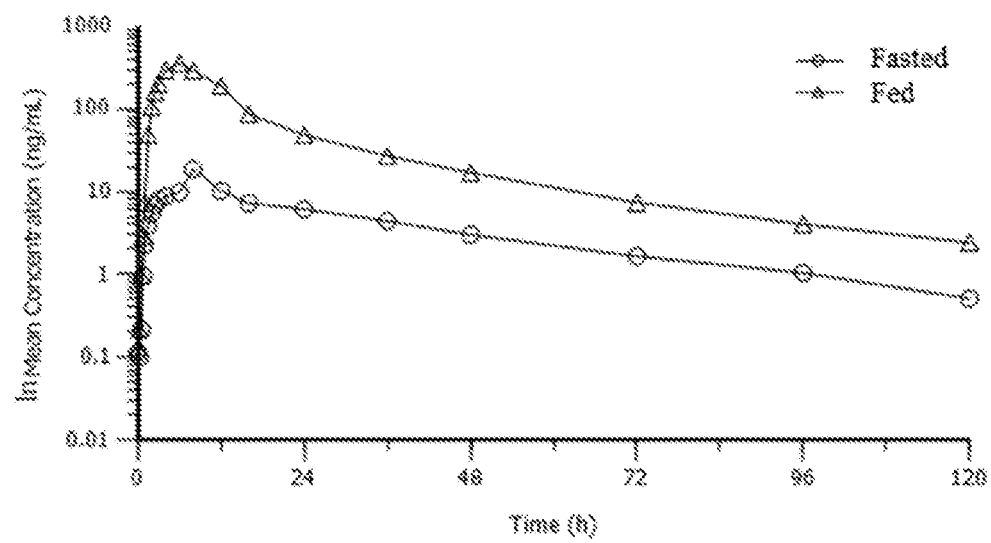

Administration of oral cannabinoid solutions of the present invention under fed conditions resulted in an appreciable AUC difference in 7-OH-cannabidiol over administration under fasted conditions within 45 minutes. See FIG. 10. Additionally, administration of oral cannabinoid solutions of the present invention under fed conditions resulted in 35 times greater AUC of 7-OH-cannabidiol over administration under fasted conditions at 6 hours.

In conclusion, oral cannabinoid solutions of the present invention have a substantial food effect resulting in higher peak plasma concentrations in a shorter period of time and also higher overall plasma concentrations after oral administration following food intake as compared to oral administration following fasting.

Example 18. Pharmacokinetic Food-Effect Study of Single Dose Cannabidiol Oral Solution in Healthy Subjects Method An open label, randomized, single-dose, four-treatment four-period, four-way crossover food-effect study of multiple formulations was conducted on healthy subjects. The study assessed pharmacokinetics of a single-dose of 10 mg/kg of 3 separate cannabidiol formulations (#LF41 and #LF42 from Table 26 above and #A11 from Table 15 above) administered under fed conditions and 1 cannabidiol formulation (#LF42 above) under fasted conditions. Subjects were enrolled in the study and each was subjected to the fasted and fed treatment arms in separate periods followed by a 7-day wash-out period. For pharmacokinetic analysis, nominal time and default lambda-z selections were used. All below quantifiable limit values were set to zero and all subjects were included in the analysis.

Results i. Cannabidiol Oral Solution Sesame Oil Formulation #LF42, Fed vs. Fasted Substantial increases in both cannabidiol and 7-OH-cannabidiol maximum and total exposure, based on $\ln(C_{max})$, $\ln(AUC_{0-t})$, and $\ln(AUC_{0-inf})$, were observed after administration of formulation #LF42 at 10 mg/kg with food compared to formulation #LF42 at 10 mg/kg administered under fasted conditions. Cannabidiol $C_{max}$ was approximately 10.5-fold higher after administration with food compared to administration under fasted conditions. Cannabidiol $AUC_{0-t}$ and $AUC_{0-inf}$ were approximately 7.5-fold and 3.3-fold higher, respectively, after administration with food compared to administration under fasted conditions. 7-OH-cannabidiol $C_{max}$ was approximately 4.5-fold higher after administration with food compared to administration under fasted conditions. 7-OH-cannabidiol $AUC_{0-t}$ and $AUC_{0-inf}$ were approximately 4.3-fold and 3.7-fold higher, respectively, after administration with food compared to administration under fasted conditions. Thus, there is a substantial food effect when administering lipid formulations of the present invention.

ii. Cannabidiol Oral Solution Medium Chain Triglyceride (MCT) Formulation #LF41 Fed vs. #LF42 Fasted Substantial increases in both cannabidiol and 7-OH-cannabidiol maximum and total exposure, based on $\ln(C_{max})$, $\ln(AUC_{0-t})$, and $\ln(AUC_{0-inf})$, were observed after administration of formulation #LF41 at 10 mg/kg with food compared to formulation #LF42 at 10 mg/kg administered under fasted conditions. Cannabidiol $C_{max}$ was approximately 10.8-fold higher after administration with food compared to administration under fasted conditions. Cannabidiol $AUC_{0-t}$ and $AUC_{0-inf}$ were approximately 6.8-fold and 3.3-fold higher, respectively, after administration with food compared to administration under fasted conditions. 7-OH-cannabidiol $C_{max}$ was approximately 4.1-fold higher after administration with food compared to administration under fasted conditions. 7-OH-cannabidiol $AUC_{0-t}$ and $AUC_{0-inf}$ were approximately 4.0-fold and 3.5-fold higher, respectively, after administration with food compared to administration under fasted conditions. Thus, there is a substantial food effect when administering medium chain glyceride formulations of the present invention.

iii. Cannabidiol Oral Solution Ethanol Formulation #A11 Fed vs. #LF42 Fasted

Substantial increases in both cannabidiol and 7-OH-cannabidiol maximum and total exposure, based on $\ln(C_{max})$, $\ln(AUC_{0-t})$, and $\ln(AUC_{0-inf})$, were observed after administration of formulation #A11 at 10 mg/kg with food compared to formulation #LF42 at 10 mg/kg administered under fasted conditions. Cannabidiol $C_{max}$ was approximately 9.5-fold higher after administration with food compared to administration under fasted conditions. Cannabidiol $AUC_{0-t}$ and $AUC_{0-inf}$ were approximately 6.9-fold and 4.0-fold higher, respectively, after administration with food compared to administration under fasted conditions. 7-OH-cannabidiol $C_{max}$ was approximately 3.8-fold higher after administration with food compared to administration under fasted conditions. 7-OH-cannabidiol $AUC_{0-t}$ and $AUC_{0-inf}$ were approximately 4.6-fold and 4.0-fold higher, respectively, after administration with food compared to administration under fasted conditions. Thus, there is a substantial food effect when administering hydro-alcohol formulations of the present invention.

Example 19. Safety Study of CBD in Pediatric Patients with Refractory Epilepsy A long-term safety study was conducted in pediatric patients with refractory epilepsy who had previously participated in a Phase 1/2 pharmacokinetic study to assess the pharmacokinetics and safety of multiple doses of pharmaceutical cannabidiol oral solution (MCT formulation, 300 mg/mL, administered BID) in pediatric subjects with treatment-resistant seizure disorder. This was a long-term, open-label, 48-week study for pediatric subjects aged 1 year to 17 years with refractory epilepsy. This study is detailed in Example 16, above.

52 subjects (9 infants, 26 children, and 17 adolescents) were enrolled and had received at least one dose of cannabidiol oral solution in the study. Seven subjects prematurely discontinued treatment and study participation. Eleven subjects completed treatment in the study, and thirty-four (34) subjects remained on treatment after the study. The study included 5 subjects aged 1 to <2 years (infants); 9 subjects aged 2 to <12 years (children), with ≥3 subjects under the age of 6 years; 6 subjects aged 12 to ≤17 years (adolescents), with ≥3 subjects under the age of 16 years.

Results and Discussion

A preliminary review of the data from the long-term safety study showed weight loss. Analysis of the median percent change in weight showed a dose-dependent decrease in weight change at week 24. The dose-dependency became less prominent over the course of the study (up to week 48). This may be due to a fewer number of patients being included in the analysis and frequent shifting of dosing during the later time periods.

The mean modal dose (i.e., the dose with the longest duration) was 23.47 mg/kg/day, and the mean number of days on-study for all subjects was 220.6. Overall, 7 subjects (13.5%) had dose reductions resulting from an Adverse Event ("AE"), and 3 subjects (5.8%) had dose reductions due to other reasons. The frequency of dose reductions was greater in the subjects receiving 40 mg/kg/day compared with subjects receiving 10 mg/kg/day (7 subjects [35.0%] and 2 subjects [14.3%], respectively). Dose reductions resulting from an AE were more frequent among subjects receiving 40 mg/kg/day compared with subjects receiving 10 mg/kg/day (6 subjects [30.0%] and 1 subject [7.1%], respectively). No subjects receiving 20 mg/kg/day and no infants had dose reductions.

Among children, 6 subjects (11.5%) had dose reductions resulting from an AE, and 2 subjects (3.8%) had dose reductions due to other reasons. The frequency of dose reductions was greater in the subjects receiving 40 mg/kg/day compared with subjects receiving 10 mg/kg/day (5 subjects [25.0%] and 2 subjects [14.3%], respectively).

Among infants, 3 subjects (33.3%) were taking 20 to <40 mg/kg/day, and 6 subjects (66.7%) were taking 40 mg/kg/day. Among children, 7 subjects (26.9%) were taking 10 to <20 mg/kg/day, 10 subjects (38.5%) were taking 20 to <40 mg/kg/day, and 8 subjects (30.8%) were taking 40 mg/kg/day. Among adolescents, 3 subjects (17.6%) were taking 10 to <20 mg/kg/day, 8 subjects (47.1%) were taking 20 to <40 mg/kg/day, and 6 subjects (35.3%) were taking 40 mg/kg/day.

Among adolescents, 1 subject (1.9%) had a dose reduction resulting from an AE, and 1 subject (1.9%) had a dose reduction due to other reasons. Both dose reductions occurred in subjects receiving 40 mg/kg/day.

Overall, 1 subject (1.9%) was taking <10 mg/kg/day, 10 subjects (19.2%) were taking between 10 and <20 mg/kg/day, 20 subjects (38.5%) were taking between 20 and <40 mg/kg/day, and 20 subjects (38.5%) were taking ≥40 mg/kg/day as of the data cut-off.

A total of 233 AEs were reported in 44 subjects; the most frequently reported AEs were anemia, diarrhea, constipation, pyrexia, upper respiratory tract infection, seizure, somnolence, and aggression. Overall, 30.0% of subjects on the 40 mg/kg/day dose required dose reductions due to adverse events (AEs). However, many patients increased their dose over the duration of the study, with 21 subjects (40.4%) taking 20 to <40 mg/kg/day and 20 subjects (38.5%) taking 40 mg/kg/day as of the data cut-off. Cannabidiol oral solution was safe and well-tolerated even at doses as high as 40 mg/kg/day.

TABLE 68

Distribution of Subjects by Dose

| | Infants (N = 9) | Children (N = 26) | Adolescents (N = 17) | All Subjects (N = 52) |
|---|---|---|---|---|
| Number of subjects taking dose as of cut-off | | | | |
| 0.5 mg/kg/day | 0 | 1 (3.8%) | 0 | 1 (1.9%) |
| 10 mg/kg/day | 0 | 6 (23.1%) | 3 (17.6%) | 9 (17.3%) |
| 10.5 mg/kg/day | 0 | 1 (3.8%) | 0 | 1 (1.9%) |
| 20 mg/kg/day | 2 (22.2%) | 7 (26.9%) | 3 (17.6%) | 12 (23.1%) |
| 22 mg/kg/day | 0 | 0 | 1 (5.9%) | 1 (1.9%) |
| 30 mg/kg/day | 1 (11.1%) | 2 (7.7%) | 3 (17.6%) | 6 (11.5%) |
| 39.4 mg/kg/day | 0 | 0 | 1 (5.9%) | 1 (1.9%) |
| 40 mg/kg/day | 6 (66.7%) | 8 (30.8%) | 6 (35.3%) | 20 (38.5%) |
| Number of subjects taking dose (as categorized) as of cut-off | | | | |
| <10 mg/kg/day | 0 | 1 (3.8%) | 0 | 1 (1.9%) |
| 10-<20 mg/kg/day | 0 | 7 (26.9%) | 3 (17.6%) | 10 (19.2%) |
| 20-<40 mg/kg/day | 3 (33.3%) | 9 (34.6%) | 8 (47.1%) | 20 (38.5%) |
| ≥40 mg/kg/day | 6 (66.7%) | 8 (30.8%) | 6 (35.3%) | 20 (38.5%) |

BID = twice daily;
N = total number;
n = sample size.
Age Category:
Infants = 1 to <2 years of age,
Children = 2 to <12 years of age,
Adolescents = 12 to ≤17 years of age.
Percentages are calculated as n/N.

Weight increase and somnolence that were related to the CBD were each reported in 4 subjects (7.7%). Compared with the mean weight of all subjects at baseline (27.88 kg), mean weight increased at Week 24 (+1.15 kg). Mean weight continued to increase during the study (+1.74 kg at week 36, +1.94 kg at Final Visit/Discontinuation Visit, and +2.14 kg at Follow-Up Visit).

TABLE 69

Subject Weights-Change from Baseline (Safety Analysis Population)

| Parameter Visit (Unit) | Statistic | Infants (N = 9) | Children (N = 26) | Adolescents (N = 17) | All Subjects (N = 52) |
|---|---|---|---|---|---|
| Weight (kg) Baseline* | n | 9 | 26 | 17 | 52 |
| | Mean (SD) | 10.86 (1.256) | 23.32 (10.583) | 43.85 (16.480) | 27.88 (16.945) |
| | Median | 11.10 | 21.90 | 39.20 | 25.35 |
| | Min, Max | 9.1, 12.9 | 12.5, 55.0 | 20.4, 82.9 | 9.1, 82.9 |
| Week 24 | n | 8 | 22 | 14 | 44 |
| | Mean (SD) | 1.10 (0.796) | 1.26 (1.424) | 1.01 (2.903) | 1.15 (1.912) |
| | Median | 0.95 | 1.65 | 1.02 1.00 | 1.10 |
| | Min, Max | −0.1, 2.3 | −1.4, 3.8 | 1.03 −4.0, 5.0 | −4.0, 5.0 |
| Week 36 | n | 8 | 18 | 13 | 39 |
| | Mean (SD) | 1.27 (0.994) | 1.93 (1.996) | 1.77 (3.457) | 1.74 (2.409) |
| | Median | 1.30 | 1.70 | 1.40 | 1.50 |
| | Min, Max | 0.0, 2.7 | −1.2, 6.0 | −6.1, 7.0 | −6.1, 7.0 |
| Final Visit/Discontinuation Visit | n | 7 | 12 | 5 | 18 |
| | Mean (SD) | 1.80 (—) | 1.81 (1.377) | 2.28 (2.093) | 1.94 (1.519) |
| | Median | 1.80 | 1.45 | 1.10 | 1.45 |
| | Min, Max | 1.8, 1.8 | −0.3, 4.3 | 0.3, 5.1 | −0.3, 5.1 |
| Follow-Up Visit | n | 1 | 8 | 2 | 11 |
| | Mean (SD) | 1.50 (—) | 2.13 (1.729) | 2.50 (3.394) | 2.14 (1.819) |
| | Median | 1.50 | 1.50 | 2.50 | 1.50 |
| | Min, Max | 1.5, 1.5 | −0.1, 5.2 | 0.1, 4.9 | −0.1, 5.2 |

Max = maximum;
Min = minimum;
N = total number;
n = sample size;
SD = standard deviation.
Age Category:
Infants = 1 to <2 years of age,
Children = 2 to <12 years of age,
Adolescents = 12 to ≤17 years of age.

There was a dose-response decrease in weight gain with the maximum effect seen at the 40 mg/kg/day dose. These data indicate that cannabidiol oral solution at 300 mg/mL up to doses of 40 mg/kg/day are safe and generally well-tolerated, and data from the long-term safety study indicate that the 40 mg/kg/day may be the most efficacious for both seizure control as well as the effect on weight gain.

Prader-Willi Syndrome ("PWS"), is a multifaceted developmental disorder and the most common genetic syndrome associated with obesity (McAllister and Whittington, 2011; Gunay-Aygun et al., 1997). It is caused by the absent expression of paternally-inherited genes in the PWS region on 15q11-q13 (Ledbetter et al., 1981). While it presents with generalized hypotonia and developmental delay in infancy, PWS then manifests with uncontrollable appetite, hyperphagia, and excessive weight gain leading to severe obesity (Grechi et al., 2012).

Clinically, PWS patients suffer a complex pattern of physical, behavioral, endocrine, and intellectual deficiencies. Endocrine abnormalities lead to hypogonadism and short stature. In particular, growth hormone deficiency is reported to occur in 40% to 100% of the population (Griggs et al., 2015) and is commonly treated with growth hormone (Butler et al., 2015). Behavioral disorders include obsessive compulsive behaviors such as skin picking, hoarding, re-doing and repetitive speech (Griggs et al, 2015).

The greatest unmet medical need in Prader-Willi Syndrome is the hyperphagia and related behaviors leading to morbid obesity and diabetes and their resulting cardiovascular complications. Cannabidiol (CBD) is a low-affinity antagonist of CB1, but it may also modulate CB1 receptor signaling through its inhibition of the metabolism of the endogenous cannabinoid, anandamide (Ibeas Bih et al., 2015). As for appetite, CBD has been shown to decrease food intake in rats under stressful conditions and reduce ad lib intake of high-sugar feed when compared to vehicle-treated controls (Silveira Filho and Tufik, 1981). In addition, CBD has been shown to diminish daily food consumption without affecting daily water intake (Wierbucka-Ryback and Bojanowska, 2014) as well as inhibited hyperphagia induced by cannabinoid (CB1) or 5-hydroxytryptamine (5-HT1A) serotonin receptor agonists suggesting a role for CBD as a regulator of food intake (Scopinho et al., 2011). Thus, cannabidiol (CBD) may have the potential to address the hyperphagia associated with Prader-Willi Syndrome patients.

Example 20. Study of Efficacy of Cannabidiol on Infantile Spasms with Vigabatrin or ACTH as Initial Therapy The following study is ongoing and no results yet been recorded.

Protocol

A Phase 2, multi-center, randomized, placebo-controlled, parallel-group study will be conducted to assess the efficacy, safety of cannabidiol oral solution as an adjunctive therapy in infantile spasm patients with either vigabatrin or adrenocorticotropic hormone ("ACTH") as the initial therapy.

The study will be comprised of Part A and Part B. Part A includes 5 periods: a Screening Period (14 to 28 days), a Titration period (5 or more days), a Treatment Period (14 days), a Taper Period (approximately 14±3 days) for patients who elect not to enroll in the open-label long-term safety study, and a Follow-up Period (30±7 days). The overall maximum study duration is expected to be approximately 101 days. Part B will consist of a Safety Treatment Period (48 weeks), Tapering (2 weeks), and a follow up period (30 days). The overall study duration is expected to be 64 weeks for those patients who complete the Safety period.

120 Eligible subjects will be selected from children aged 6 months through 36 months with a diagnosis of infantile spasms and will be randomized equally into one of six treatment groups:
1) vigabatrin, 2) vigabatrin plus 20 milligrams per kilogram per day ("mg/kg/day") cannabidiol oral solution 3) vigabatrin plus 40 mg/kg/day cannabidiol oral solution vigabatrin, 4) ACTH, 5) ACTH plus 20 milligrams per kilogram per day ("mg/kg/day") cannabidiol oral solution and 6) ACTH plus 40 mg/kg/day cannabidiol oral solution.

Specifically, twenty subjects will be enrolled in each dose cohort that A) fit the following criteria: 1. parent(s)/caregiver(s) fully comprehends and signs the informed consent form, understands all study procedures, and can communicate satisfactorily with the Investigator and study coordinator; 2. provide informed consent of patients and/or parent(s)/caregiver(s) in accordance with applicable laws, regulations, and local requirements; 3. male or female between 6 month to 36 months of age (inclusive) at time of consent; 4. clinical diagnosis of infantile spasms, confirmed by video-EEG analysis (including at least one cluster of electroclinical spasms [≥3 in any 10-minute epoch]) obtained during the Screening Period and read by the Investigator. 5. general good health (defined as the absence of any clinically relevant abnormalities as determined by the Investigator) based on physical and neurological examinations, medical history, and clinical laboratory values completed during the Screening Visit (Visit 1); and 6. in the opinion of the Investigator, the parent(s)/caregiver(s) are willing and able to comply with the study procedures and visit schedules, and B) do not meet the following criteria: 1) is considered by the Investigator, for any reason (including, but not limited to, the risks described as precautions, warnings, and contraindications in the current version of the Investigator's Brochure for Cannabidiol Oral Solution) to be an unsuitable candidate to receive the study drug; 2) known or suspected allergy to Cannabidiol Oral Solution; 3) use of any Cannabidiol/cannabis product within 30 days of study entry; 4) patient is diagnosed or suspected of having Tuberous Sclerosis; 5) patient has received treatment with either Vigabatrin, ACTH, or high-dose steroids previously; 6) previous therapy with felbamate, clobazam, or the ketogenic diet; 7) positive drug screen for THC; or 8) patient currently on any disallowed medication listed in Appendix 2 (e.g., phenytoin, fluvoxamine, carbamazepine, and St. Johns Wort).

The study will be conducted in the following parts. Part A: video-electroencephalography ("EEG") will be conducted during the screening period and repeated at Day 0 and overnight at Day 14 for each treatment group. Response to treatment will be scored using the following methodology: 1) complete response-complete resolution of spasms and hypsarrythmia (if present at baseline) confirmed by video-EEG at Day 14; 2) partial response-substantive change in background EEG or reduction in spasms on video-EEG obtained at Day 14; and 3) no response—no improvement or worsening of spasms/hypsarrythmia burden at Day 14.

Part B: After Day 14, patients who volunteer may participate in the long-term safety phase. Treatment visits will be scheduled monthly for 3 months, and then quarterly thereafter.

Endpoints

The primary efficacy endpoint will be the percent of subjects who are considered complete responders at Day 14, defined as complete resolution of spasms and hypsarrhythmia, confirmed by video-EEG as determined by the Independent Central Reader.

The secondary efficacy endpoints will be: 1) percent of subjects with absence of infantile spasms at Day 14; 2) percent of subjects with absence of hypsarrhythmia at Day 14; 3) median reduction in seizure-burden comparing video-EEG at Screening to repeat video-EEG at Day 14; and 4) parent impression of efficacy and tolerability of study drug (CGIC) at Study Completion/Early Discontinuation (Visit 3).

The exploratory efficacy endpoints will be 1) percent of spasm-free days at Day 14 comparing either vigabatrin or ACTH with CBD versus vigabatrin or ACTH alone and 2) correlation between plasma drug levels and response.

The safety endpoints will be: 1) the incidence of treatment-emergent adverse events ("AE"); 2) clinical laboratory assessments; 3) vital signs (blood pressure, pulse rate, respiration rate, and temperature); 4) physical and neurological examination assessments; 5) urine; 6) THC screen; 7) medical history and 8) prior and concomitant medications.

The pharmacokinetic endpoints will be trough concentrations (Ctrough) of cannabidiol and metabolite 7-hydoxy-cannabidiol ("7 OH-CBD") drawn prior to dosing and at hours 2,4, and 6 after dose at Visits 2 and 3 to assess exposure-response relationships. A food diary will be used to record the type of meals consumed in relation to the pharmacokinetic blood draws.

Methods

Titration Period

Once the patient has been approved for the study, they will return to the study clinic where the physician will prescribe either vigabatrin or ACTH and the patient will be randomized to the appropriate study arm. The following activities will be completed: 1. review of inclusion and exclusion criteria; 2) obtain a urine sample for urinalysis; 3. record concomitant medications and concomitant procedures; 4. record vital signs (blood pressure, pulse rate, respiratory rate, and temperature measurements); 5. perform a complete physical examination including height and weight. The weight obtained on during this visit will be used to calculate the dose volume. The dosing volume will remain constant throughout the Titration and Treatment Periods.; 6. Draw blood samples for hematology and chemistry; 7. perform a brief neurology examination and 8. record AEs and serious AEs ("SAE").

Screening Period

Once the prescribed ACTH or vigabatrin is ready to be dispensed, the subject will be admitted to the study center as an inpatient on Day 0. The following procedures and assessments must be performed on Day 0 for all subjects prior to IP administration on Day 1; 1. record concomitant medications and concomitant procedures; 2. Perform a brief neurology examination; 3. record vital signs (blood pressure, pulse rate, respiratory rate, and temperature measurements), 4. record and Review Daily Seizure Diary; 5. record AEs and SAEs and 6. perform a 24-hour video-EEG.

Treatment Period

Patients will be dosed twice daily (i.e., full daily dose of 0, 20, or 40 mg/kg/day) from Day 1 through Day 14 according to the subject's assigned cohort. Doses will be administered at approximately 12-hour intervals. Patients will be released from the study center after assessments and the 6-hour pharmacokinetic blood draw are complete. The final dose of the investigational product will be administered in the evening on Day 14. Patients will be admitted for an End of Therapy visit on Day 14, which will include a 24-hour video EEG.

Part B Visits

The following activities will be completed during each Part B Visit, which will occur at 1, 2, 3, 6, and 9 months after the Treatment Period ends: 1. record concomitant medications and concomitant procedures; 2. record vital signs (blood pressure, pulse rate, respiratory rate, and temperature measurements); 4. record and review daily seizure and food diary; 5. perform a physical examination including height and weight; 6. perform a brief neurology examination and 7. record AEs and SAEs.

We claim:

1. A method of treating Prader-Willi syndrome in a subject in need of such treatment, comprising administering to the subject an effective amount of an oral pharmaceutical formulation consisting of:
   from about 8% to about 32% w/w cannabidiol;
   caprylic/capric triglyceride at a concentration of 58 to 90% w/w;
   alpha tocopherol at a concentration of from 0.01 to 1% w/w;
   a sweetener at a concentration of 0.01 to 2% w/w; and
   a flavoring agent at a concentration of 0.01 to about 1% w/w,
wherein w/w denotes weight by weight of the formulation, and wherein the effective amount results in administration of from about 20 to about 40 milligrams of cannabidiol per kilogram body weight of the subject per day, and wherein the subject is a human subject.

2. The method of claim 1, wherein the method involves treating one or more symptoms of Prader-Willi syndrome.

3. The method of claim 2, wherein the one or more symptoms of Prader-Willi syndrome is hyperphagia.

4. The method of claim 1, wherein the human subject is a pediatric subject.

5. The method of claim 1, wherein the dose of the cannabidiol is about 40 milligrams of cannabidiol per kilogram body weight of the subject per day.

6. The method of claim 1, wherein the cannabidiol is greater than 98% pure.

7. The method of claim 1, wherein the cannabidiol is synthetic cannabidiol.

8. The method of claim 1, wherein the oral pharmaceutical formulation consists of:
   10.53% w/w of cannabidiol;
   88.945% w/w of caprylic/capric triglyceride;
   0.2% w/w of alpha tocopherol;
   0.025% w/w of sweetener; and
   0.3% w/w of flavoring agent.

9. The method of claim 1, wherein the oral pharmaceutical formulation consists of:
   31.09% w/w of cannabidiol;
   68.385% w/w of caprylic/capric triglyceride;
   0.2% w/w of alpha tocopherol;
   0.025% w/w of sweetener; and
   0.3% w/w of flavoring agent.

* * * * *